United States Patent
Hilvo et al.

(10) Patent No.: US 12,399,188 B2
(45) Date of Patent: Aug. 26, 2025

(54) BIOMARKERS FOR CARDIOVASCULAR EVENTS

(71) Applicant: Zora Biosciences OY, Espoo (FI)

(72) Inventors: Mika Hilvo, Helsinki (FI); Reijo Laaksonen, Lempaeaelae (FI)

(73) Assignee: ZORA BIOSCIENCES OY, Espoo (FI)

( * ) Notice: Subject to any disclaimer, the term of this patent is extended or adjusted under 35 U.S.C. 154(b) by 1049 days.

(21) Appl. No.: 17/295,139

(22) PCT Filed: Dec. 6, 2019

(86) PCT No.: PCT/EP2019/084008
§ 371 (c)(1),
(2) Date: May 19, 2021

(87) PCT Pub. No.: WO2020/115288
PCT Pub. Date: Jun. 11, 2020

(65) Prior Publication Data
US 2022/0003791 A1    Jan. 6, 2022

Related U.S. Application Data

(60) Provisional application No. 62/776,272, filed on Dec. 6, 2018.

(51) Int. Cl.
*G01N 33/92* (2006.01)

(52) U.S. Cl.
CPC ......... *G01N 33/92* (2013.01); *G01N 2405/04* (2013.01); *G01N 2405/08* (2013.01); *G01N 2570/00* (2013.01); *G01N 2800/32* (2013.01); *G01N 2800/50* (2013.01); *G01N 2800/52* (2013.01)

(58) Field of Classification Search
CPC ......... G01N 2405/04; G01N 2405/08; G01N 2570/00; G01N 2800/32; G01N 2800/50; G01N 2800/52; G01N 33/92
See application file for complete search history.

(56) References Cited

U.S. PATENT DOCUMENTS

| | | | |
|---|---|---|---|
| 10,551,394 B2* | 2/2020 | Laaksonen | A61K 31/397 |
| 12,025,623 B2* | 7/2024 | Laaksonen | G01N 33/92 |
| 2013/0045217 A1 | 2/2013 | Laaksonen et al. | |
| 2014/0295467 A1 | 10/2014 | Laaksonen et al. | |
| 2015/0362513 A1 | 12/2015 | Laaksonen | |
| 2016/0018423 A1 | 1/2016 | Laaksonen | |

FOREIGN PATENT DOCUMENTS

| | | |
|---|---|---|
| JP | 2013527449 A | 6/2013 |
| JP | 2014532885 A | 12/2014 |
| JP | 2016511407 A | 4/2016 |
| JP | 2017519989 A | 7/2017 |
| KR | 10-1598597 B1 | 3/2016 |
| WO | 2011/138419 A1 | 11/2011 |
| WO | 2011/161062 A2 | 12/2011 |
| WO | 2013/068373 A2 | 5/2013 |
| WO | 2013/068374 A2 | 5/2013 |
| WO | 2017134264 A1 | 8/2017 |

OTHER PUBLICATIONS

International Search Report and Written Opinion dated Mar. 31, 2020 for International Application No. PCT/EP2019/084008 (Authorized officer, Lopez Garcia, F.), 22 pages.

Mundra et al., "Large-scale plasma lipidomic profiling identifies lipids that predict cardiovascular events in secondary prevention", JCI Insight, 2018, vol. 3, No. 17, 15 pages.

Kauhanen et al., "Development and validation of a high-throughput LC-MS/MS assay for routine measurement of molecular ceramides", Analytical and Bioanalytical Chemistry, 2016, vol. 408, No. 13, pp. 3475-3483.

Hilvo et al., "Development and validation of a ceramide- and phospholipid-based cardiovascular risk estimation score for coronary artery disease patients", European Heart Journal, 2020, vol. 41, pp. 371-380.

* cited by examiner

*Primary Examiner* — Galina M. Yakovleva
(74) *Attorney, Agent, or Firm* — MH2 Technology Law Group, LLP

(57) ABSTRACT

The present disclosure relates to methods and uses involving the determination of lipid concentrations in order to diagnose, predict, prevent and/or treat one or more cardiovascular events in a subject. The methods include analyzing lipid concentrations of a sample from the subject and comparing them to a control.

17 Claims, No Drawings

BIOMARKERS FOR CARDIOVASCULAR EVENTS

CROSS-REFERENCE TO RELATED APPLICATIONS

This application is a U.S. National Stage application of PCT/EP2019/084008 filed 6 Dec. 2019, which claims priority to U.S. Provisional Application No. 62/776,272 filed 6 Dec. 2018, the entire disclosures of which are herein incorporated by reference.

FIELD OF THE INVENTION

The present disclosure is related to the field of prognostic biomarkers for cardiovascular (CV) outcomes.

In particular, it provides a novel in vitro method for assessing the risk of a subject to develop cardiovascular events. In addition, the present biomarkers can be used in methods to evaluate the effectiveness of a cardiovascular disease (CVD) treatment, treating cardiovascular disease and preventing cardiovascular events.

BACKGROUND

Worldwide, cardiovascular diseases are among the leading causes of mortality and morbidity with ever-increasing prevalence. CVD is used to classify numerous conditions that affect the heart, heart valves, blood, and vasculature of the body.

Over decades, plasma or serum total cholesterol, low density lipoprotein (LDL) or high density lipoprotein (HDL) concentrations have been used as gold standard biomarkers for CVD risk prediction and treatment targets. Recent studies have, however, showed that these widely used biomarkers do not reliably associate with CV outcomes, such as myocardial infarction (MI) or cardiovascular death. For example, it has been observed that one half of acute myocardial infarction (AMI) patients have LDL-cholesterol (LDL-C) levels which are within the recommended normal range. Regardless of this, lowering LDL-C concentration is currently used as a main target of CVD treatments, such as widely used statin treatments. In addition, it has been noticed that there is still a substantial residual risk of developing CVD events in statin treated patients, despite the lowering of LDL-C. Accordingly, there is a need for additional prognostic and therapeutic targets beyond LDL-C.

In addition to total cholesterol, LDL-C, and HDL-C, several non-lipid risk factors (including age, blood pressure, diabetes, smoking, and body-mass-index) are used in risk assessment to evaluate an individual's risk for cardiovascular events.

Statins are a family of lipid lowering drugs for people at high risk of cardiovascular events. Statins are widely used. For example, in the USA alone there are almost 20 million statin treated patients. Moreover, it has been calculated that some 50 million patients would benefit from statin treatment in the USA alone. However, despite statin treatment, the CVD patients have a substantial risk of developing severe CVD-related events. An early targeted initiation of preventive measures for CVD-related severe events, such as AMI and cardiovascular death, would be of great benefit and would provide a major opportunity in reducing mortality and morbidity in patients suffering from CVD. Accurate identification of individuals who are at risk of developing CVD and cardiovascular events is essential. Traditional risk assessment fails to recognize a large proportion of patients at high risk, while a large proportion of individuals are classified as having intermediate risk, leaving patient management uncertain. Additional strategies to further refine risk assessment of the CVD patients are therefore highly needed.

A large group of lipid molecules have been identified for predicting cardiovascular events in certain subject populations, for example, in Zora Biosciences patent applications WO 2011138419, WO 2011161062, WO 2013068373 and WO 2013068374. However, there remains a need for improved methods for identification of individuals having a risk to develop cardiovascular events.

The biomarker combination of the present disclosure offers superior performance for risk stratification compared to any other currently used lipid based cardiovascular biomarker. In addition, the level of the present biomarker combination can be affected with specific lipid modifying treatments, such as statins.

Therefore, the biomarker combination of the present disclosure offers precise and actionable risk stratification of cardiovascular events.

SUMMARY

The present disclosure provides novel biomarker combination and associated diagnostic methods and uses for the identification of subjects having a risk of developing cardiovascular events. Such methods and uses comprise monitoring a combination of specific lipid concentrations in a sample from a subject and comparing such concentrations to those in a control.

The novel biomarker combination consist of at least one ceramide (Cer) molecule and at least one phosphatidylcholine (PC) molecule. The at least one ceramide is selected from ceramides of Formula I and the at least one phosphatidylcholine is selected from phosphatidylcholines of Formula II.

Ceramides of Formula I have the following structure:

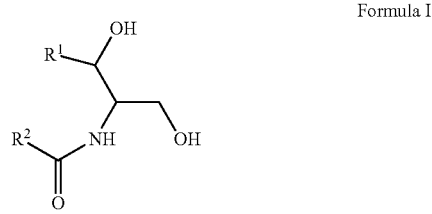

Formula I wherein $R^1$ is a saturated, mono-unsaturated or di-unsaturated alkyl chain having 11-17 carbon atoms, and wherein $R^2$ is a saturated, mono-unsaturated or di-unsaturated alkyl chain having 13-25 carbon atoms.

Phosphatidylcholines of Formula II have the following structure:

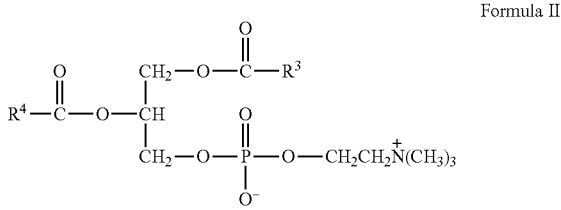

Formula II wherein $R^3$ and $R^4$ are saturated, mono-unsaturated or poly-unsaturated alkyl chains.

In a first aspect of the present disclosure, a method is provided for determining the risk of a subject to develop one or more cardiovascular events, the method comprising assaying a sample from said subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the method of determining the risk of a subject to develop one or more cardiovascular events the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events.

TABLE 1

Additional ceramides (Cer, Table 1a) and phosphatidylcholines (PC, Table 1b). According to all aspects of the present disclosure, the PC can be a brutto PC or a molecular PC. According to the present disclosure, molecular PCs are not limited to the examples presented in Table 1. Direction of change refers to a change in a quantity, amount, abundance, level or concentration of the biomarker in a sample from a subject when the subject is having a risk of developing one or more cardiovascular events, when compared to a control. When evaluating the effectiveness of a CVD treatment in a subject, according to some aspects of the precent disclosure, directions of change are opposite of which are presented in Table 1.

Table 1a.

| Ceramides | Direction of change |
|---|---|
| Cer(d16:1/16:0) | increase |
| Cer(d16:1/18:0) | increase |
| Cer(d16:1/20:0) | increase |
| Cer(d16:1/22:0) | increase |
| Cer(d16:1/23:0) | decrease |
| Cer(d16:1/24:0) | decrease |
| Cer(d16:1/24:1) | increase |
| Cer(d16:1/26:0) | decrease |
| Cer(d18:1/14:0) | increase |
| Cer(d18:1/16:0) | increase |
| Cer(d18:1/18:0) | increase |
| Cer(d18:1/20:0) | increase |
| Cer(d18:1/22:0) | increase |
| Cer(d18:1/23:0) | decrease |
| Cer(d18:1/24:0) | decrease |
| Cer(d18:1/24:1) | increase |
| Cer(d18:1/26:0) | decrease |
| Cer(d18:1/26:1) | increase |
| Cer(d18:2/16:0) | increase |
| Cer(d18:2/18:0) | increase |
| Cer(d18:2/20:0) | increase |
| Cer(d18:2/22:0) | increase |
| Cer(d18:2/23:0) | decrease |
| Cer(d18:2/24:0) | decrease |
| Cer(d18:2/24:1) | increase |
| Cer(d18:2/26:0) | decrease |
| Cer(d18:2/26:1) | increase |
| Cer(d20:1/22:0) | increase |
| Cer(d20:1/23:0) | decrease |
| Cer(d20:1/24:0) | decrease |
| Cer(d20:1/24:1) | increase |

Table 1b.

| Phosphatidylcholines | Direction of change | Examples of phosphatidylcholine molecular species |
|---|---|---|
| PC 28:0 | increase | PC 14:0/14:0 |
| PC 28:1 | decrease | PC 14:0/14:1 |
| PC 30:0 | increase | PC 14:0/16:0 |
| PC 30:1 | increase | PC 14:0/16:1, PC 14:1/16:0 |
| PC 30:2 | decrease | PC 14:0/16:2, PC 14:1/16:1, PC 14:2/16:0 |
| PC 31:0 | decrease | PC 14:0/17:0 |
| PC 31:1 | decrease | PC 14:0/17:1, PC 14:1/17:0 |
| PC 32:0 | increase | PC 16:0/16:0, PC 14:0/18:0 |
| PC 32:1 | decrease | PC 14:0/18:1, PC 16:0/16:1, PC 14:1/18:0 |
| PC 32:2 | decrease | PC 14:0/18:2, PC 14:2/18:0, PC 14:1/18:1, PC 16:1/16:1, PC 16:0/16:2 |

TABLE 1-continued

Additional ceramides (Cer, Table 1a) and phosphatidylcholines (PC, Table 1b). According to all aspects of the present disclosure, the PC can be a brutto PC or a molecular PC. According to the present disclosure, molecular PCs are not limited to the examples presented in Table 1. Direction of change refers to a change in a quantity, amount, abundance, level or concentration of the biomarker in a sample from a subject when the subject is having a risk of developing one or more cardiovascular events, when compared to a control. When evaluating the effectiveness of a CVD treatment in a subject, according to some aspects of the precent disclosure, directions of change are opposite of which are presented in Table 1.

| | | |
|---|---|---|
| PC 32:3 | decrease | PC 14:3/18:0, PC 14:2/18:1, PC 14:1/18:2, PC 14:0/18:3, PC 16:0/16:3, PC 16:1/16:2, PC 16:2/16:1 |
| PC 33:1 | decrease | PC 16:0/17:1, PC 16:1/17:0 |
| PC 33:2 | decrease | PC 16:0/17:2, PC 16:1/17:1, PC 16:2/17:0 |
| PC 33:3 | increase | PC 16:0/17:3, PC 16:1/17:2, PC 16:2/17:1, PC 16:3/17:0 |
| PC 34:0 | increase | PC 16:0/18:0, PC 14:0/20:0 |
| PC 34:1 | decrease | PC 16:0/18:1, PC 16:1/18:0, PC 14:0/20:1, PC 14:1/20:0 |
| PC 34:2 | decrease | PC 16:0/18:2, PC 16:1/18:1, PC 16:2/18:0, PC 14:0/20:2, PC 14:1/20:1, PC 14:2/20:0 |
| PC 34:3 | decrease | PC 16:0/18:3, PC 16:1/18:2, PC 16:2/18:1, PC 16:3/18:0, PC 14:0/20:3, PC 14:1/20:2, PC 14:2/20:1, PC 14:3/20:0 |
| PC 34:4 | decrease | PC 16:0/18:4, PC 16:1/18:3, PC 16:2/18:2, PC 16:3/18:1, PC 16:4/18:0, PC 14:0/20:4, PC 14:1/20:3, PC 14:2/20:2, PC 14:3/20:1 |
| PC 34:5 | decrease | PC 16:1/18:4, PC 16:2/18:3, PC 16:3/18:2, PC 16:4/18:1, PC 14:0/20:5, PC 14:1/20:4, PC 14:2/20:3, PC 14:3/20:2 |
| PC 35:0 | decrease | PC 16:0/19:0, PC 17:0/18:0 |
| PC 35:1 | decrease | PC 17:0/18:1, PC 17:1/18:0, PC 16:1/19:0 |
| PC 35:2 | decrease | PC 17:0/18:2, PC 17:1/18:1, PC 17:2/18:0 |
| PC 35:3 | increase | PC 17:0/18:3, PC 17:1/18:2, PC 17:2/18:1, PC 17:3/18:0 |
| PC 35:4 | decrease | PC 17:0/18:4, PC 17:1/18:3, PC 17:2/18:2, PC 17:3/18:1, PC 17:4/18:0 |
| PC 35:5 | decrease | PC 17:1/18:4, PC 17:2/18:3, PC 17:3/18:2, PC 17:4/18:1 |
| PC 36:0 | decrease | PC 18:0/18:0, PC 16:0/20:0, PC 14:0/22:0 |
| PC 36:1 | decrease | PC 18:0/18:1, PC 16:0/20:1, PC 16:1/20:0, PC 14:0/22:1, PC 14:1/22:0 |
| PC 36:2 | decrease | PC 18:0/18:2, PC 18:1/18:1, PC 16:0/20:2, PC 16:1/20:1, PC 16:2/20:0, PC 14:0/22:2, PC 14:1/22:1, PC 14:2/22:0 |
| PC 36:3 | decrease | PC 16:0/20:3, PC 18:1/18:2, PC 18:0/18:3, PC 16:1/20:2, PC 16:2/20:1, PC 16:3/20:0, PC 14:0/22:3, PC 14:1/22:2, PC 14:2/22:1, PC 14:3/22:0 |
| PC 36:4 | decrease | PC 16:0/20:4, PC 18:2/18:2, PC 18:1/18:3, PC 18:0/18:4, PC 16:1/20:3, PC 16:2/20:2, PC 16:3/20:1, PC 16:4/20:0, PC 14:0/22:4, PC 14:1/22:3, PC 14:2/22:2, PC 14:3/22:1 |
| PC 36:5 | decrease | PC 16:0/20:5, PC 18:1/18:4, PC 18:2/18:3, PC 16:1/20:4, PC 16:2/20:3, PC 16:3/20:2, PC 16:4/20:1, PC 14:0/22:4, PC 14:1/22:3, PC 14:2/22:2, PC 14:3/22:1 |
| PC 36:6 | decrease | PC 14:0/22:6, PC 14:1/22:5, PC 14:2/22:4, PC 14:3/22:3, PC 16:1/20:5, PC 16:2/20:4, PC 16:3/20:3, PC 16:4/20:2, PC 18:2/18:4, PC 18:3/18:3 |
| PC 36:7 | increase | PC 14:1/22:6, PC 14:2/22:5, PC 14:3/22:4, PC 16:2/20:5, PC 16:3/20:4, PC 16:4/20:3, PC 18:3/18:4 |
| PC 37:1 | increase | PC 14:1/23:0, PC 16:1/21:0, PC 18:1/19:0, PC 17:0/20:1, PC 17:1/20:0 |
| PC 37:2 | decrease | PC 14:2/23:0, PC 16:2/21:0, PC 18:2/19:0, PC 17:0/20:2, PC 17:1/20:1, PC 17:2/20:0 |
| PC 37:3 | decrease | PC 17:0/20:3, PC 14:3/23:0, PC 16:3/21:0, PC 18:3/19:0, PC 17:1/20:2, PC 17:2/20:1 |
| PC 37:4 | decrease | PC 17:0/20:4, PC 16:4/21:0, PC 18:4/19:0, PC 17:1/20:3, PC 17:2/20:2, PC 17:3/20:1, PC 17:4/20:0 |
| PC 37:6 | decrease | PC 17:1/20:5, PC 17:2/20:4, PC 17:3/20:3, PC 17:4/20:2 |
| PC 38:0 | decrease | PC 14:0/24:0, PC 16:0/22:0, PC 17:0/21:0, PC 18:0/20:0, PC 19:0/19:0 |
| PC 38:1 | decrease | PC 14:1/24:0, PC 16:0/22:1, PC 16:1/22:0, PC 17:1/21:0, PC 18:0/20:1, PC 18:1/20:0 |
| PC 38:2 | decrease | PC 14:2/24:0, PC 16:0/22:1, PC 16:1/22:0, PC 17:1/21:0, PC 18:0/20:2, PC 18:1/20:1, PC 18:2/20:0 |
| PC 38:3 | decrease | PC 18:0/20:3, PC 14:3/24:0, PC 16:3/22:0, PC 16:2/22:1, PC 17:3/21:0, PC 18:1/20:2, PC 18:2/20:1, PC 18:3/20:0 |
| PC 38:4 | decrease | PC 18:0/20:4, PC 16:4/22:0, PC 16:3/22:1, PC 17:4/21:0, PC 18:1/20:3, PC 18:2/20:2, PC 18:3/20:1, PC 18:4/20:0 |
| PC 38:5 | decrease | PC 16:0/22:5, PC 18:0/20:5, PC 16:1/22:4, PC 16:4/22:1, PC 18:1/20:4, PC 18:2/20:3, PC 18:3/20:2, PC 18:4/20:1 |
| PC 38:6 | decrease | PC 16:0/22:6, PC 16:1/22:5, PC 18:1/20:5, PC 18:2/20:4, PC 18:3/20:3, PC 18:4/20:2 |
| PC 38:7 | decrease | PC 16:1/22:6, PC 16:2/22:5, PC 16:3/22:4, PC 18:2/20:5, PC 18:3/20:4 |
| PC 39:0 | decrease | PC 16:0/23:0, PC 17:0/22:0, PC 18:0/21:0, PC 19:0/20:0 |
| PC 39:2 | decrease | PC 16:2/23:0, PC 17:2/22:0, PC 18:2/21:0, PC 19:0/20:2 |
| PC 39:4 | decrease | PC 16:4/23:0, PC 17:4/22:0, PC 18:4/21:0, PC 19:0/20:4 |
| PC 39:6 | decrease | PC 19:0/20:6 |
| PC 40:1 | decrease | PC 14:1/26:0, PC 16:0/24:1, PC 16:1/24:0, PC 18:0/22:1, PC 18:1/22:0, PC 20:0/20:1 |
| PC 40:2 | increase | PC 14:2/26:0, PC 16:1/24:1, PC 16:2/24:0, PC 18:1/22:1, PC 18:2/22:0, PC 20:0/20:2, PC 20:1/20:1 |
| PC 40:3 | decrease | PC 14:3/26:0, PC 16:2/24:1, PC 16:3/24:0, PC 18:2/22:1, PC 18:3/22:0, PC 20:0/20:3, PC 20:1/20:2 |
| PC 40:4 | increase | PC 16:3/24:1, PC 16:4/24:0, PC 18:0/22:4, PC 18:3/22:1, PC 18:4/22:0, PC 20:0/20:4, PC 20:1/20:3, PC 20:2/20:2 |
| PC 40:5 | decrease | PC 16:4/24:1, PC 16:0/24:5, PC 18:0/22:5, PC 18:1/22:4, PC 18:4/22:1, PC 20:0/20:5, PC 20:1/20:4, PC 20:2/20:3 |
| PC 40:6 | decrease | PC 16:0/24:6, PC 16:1/24:5, PC 18:0/22:6, PC 18:1/22:5, PC 18:2/22:4, PC 20:1/20:5, PC 20:2/20:4, PC 20:3/20:3 |
| PC 40:8 | decrease | PC 16:2/24:6, PC 16:3/24:5, PC 18:2/22:6, PC 18:3/22:5, PC 18:4/22:4, PC 20:3/20:5, PC 20:4/20:4 |

In certain embodiments, the method of determining the risk of a subject to develop one or more cardiovascular events, further comprises after the determining step and/or after the step of assaying the at least one additional Cer and/or the at least one additional PC, diagnosing the subject, such as a human subject, as having a risk of developing one or more cardiovascular events, and administering a treatment to the subject diagnosed in the previous step.

In certain embodiments, the method of determining the risk of a subject to develop one or more cardiovascular events, further comprises after the determining step and/or after the step of assaying the at least one additional Cer and/or the at least one additional PC, diagnosing the subject, such as a human subject, as having a risk of developing one or more cardiovascular events, and administering a drug and/or providing therapeutic, behavioral and/or lifestyle modification to the subject diagnosed in the previous step.

In one aspect, the present disclosure is directed to a method of treating cardiovascular disease (CVD) or preventing one or more cardiovascular (CV) events in a subject, identified as having a risk of developing one or more CV events, the method comprising administering to the subject a treatment as described herein, wherein prior to administering the treatment, the subject has been identified as having a risk of developing one or more CV events by a method of determining the risk as described herein.

In another aspect, the present disclosure is directed to a method of treating CVD or preventing one or more CV events in a subject, the method comprising determining the risk of the subject to develop one or more CV events according to a method of determining the risk as described herein, and administering to the subject a treatment, if the subject has been identified as having a risk of developing one or more CV events.

According to the present disclosure, a treatment may comprise, for example, administering a drug and/or providing therapeutic, behavioural and/or lifestyle modification to the subject. The drug may be, for example, a statin, another lipid lowering drug, and/or a modulator of lipid concentrations as described elsewhere in the present disclosure. Behavioural and/or lifestyle modification may comprise, for example, lifestyle counselling, including, but not limited to, instructions and/or encouragement regarding a healthy diet, physical activity/exercise and/or smoking cessation. A treatment may also be a surgical operation as described herein.

In certain embodiments, the method of treating CVD or preventing one or more CV events in a subject further comprises identifying the subject as in need of the treatment or prevention, for example, by requesting a test or receiving the test results, for example, from a commercial laboratory, which provides the results of an assay useful for determining the concentration of the at least one Cer of Formula I and the concentration of the at least one PC of Formula II, and administering to the subject a treatment, for example, a therapeutically effective dose of a drug, if the subject has (an) increased concentration(s) of the at least one Cer of Formula I and/or (a) decreased concentration(s) of the at least one PC of Formula II in the sample, as compared to the control.

In another aspect of the disclosure, a method is provided for detecting at least two lipids in a sample from a subject comprising detecting a concentration of at least one ceramide (Cer) of Formula I and a concentration of at least one phosphatidylcholine (PC) of Formula II.

In certain embodiments of the method comprising the detecting as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises detecting in the sample a concentration of at least one additional Cer and/or at least one additional PC biomarker, selected from any of the Cer and PC species referred to in Table 1.

In certain embodiments, the method further comprises comparing the concentration(s) of the at least one, at least 2, at least 3, at least 4, at least 5, at least 6, at least 7, at least 8, at least 9 or at least 10 Cers of Formula I, the concentration(s) of the at least one, at least 2, at least 3, at least 4, at least 5, at least 6, at least 7, at least 8, at least 9 or at least 10 PCs of Formula II and/or the concentration(s) of the at least one additional Cer and/or the at least one additional PC, selected from any of the Cer and PC species referred to in Table 1, to a control.

In certain embodiments, the method comprises detecting in a sample from a subject a changed concentration of the at least one Cer of Formula I and/or a changed concentration of the at least one PC of Formula II, e.g. in comparison to the control.

In certain embodiments, the method comprises detecting in a sample from a subject an increased concentration of at least one Cer of Formula I and/or a decreased concentration of at least one PC of Formula II, e.g., in comparison to the control.

In certain embodiments, the method of detecting in a sample from a subject a concentration of at least one Cer of Formula I and a concentration of at least one PC of Formula II comprises using a standard combination comprising at least one Cer of Formula I and/or at least one PC of Formula II.

In certain embodiments, the standard combination comprises at least one isotope-labelled Cer of Formula I and/or at least one isotope-labelled PC of Formula II.

In certain embodiments, the isotope of the at least one isotope-labelled Cer of Formula I and/or the at least one isotope-labelled PC of Formula II is deuterium, $^{13}C$ or $^{15}N$.

In certain embodiments, the standard combination further comprises at least one additional Cer and/or at least one additional PC, selected from any of the Cer and PC species referred to in Table 1.

In certain embodiments, the at least one additional Cer and/or the at least one additional PC, selected from any of the Cer and PC species referred to in Table 1, is isotope-labelled.

In certain embodiments, the isotope of the at least one additional isotope-labelled Cer and/or the at least one additional isotope-labelled PC, selected from any of the Cer and PC species referred to in Table 1, is deuterium, $^{13}C$ or $^{15}N$.

In certain embodiments, the method further comprises comparing the concentration of the at least one Cer of Formula I and the concentration of the at least one PC of Formula II to a control, and determining the subject as having a risk of developing one or more CV events if the concentration of the at least one Cer of Formula I is increased and/or the concentration of the at least one PC of Formula II is decreased, when compared to a control.

In another aspect of the disclosure, a method is provided for obtaining data for determining the risk of a subject to develop one or more CV events, the method comprising assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the method of obtaining data as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events.

In another aspect of the disclosure, a method is provided for generating quantitative data for a subject comprising assaying a sample from the subject to determine a concentration of at least one ceramide (Cer) of Formula I and a concentration of at least one phosphatidylcholine (PC) of Formula II.

In certain embodiments of the method of generating quantitative data as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC biomarker, selected from any of the Cer and PC species referred to in Table 1.

In another aspect of the disclosure, a method is provided for evaluating the effectiveness of a CVD treatment in a subject, the method comprising assaying a sample from the subject to determine a concentration of at least one ceramide (Cer) of Formula I and a concentration of at least one phosphatidylcholine (PC) of Formula II, wherein (a) decreased concentration(s) of the at least one Cer of Formula I and/or (an) increased concentration(s) of the at least one PC of Formula II in the sample, when compared to a control, is (are) indicative of the effectiveness of said treatment.

In certain embodiments of the method of evaluating the effectiveness of a CVD treatment as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC, when compared to a control, is (are) indicative of the effectiveness of said treatment.

In certain embodiments, the method for evaluating the effectiveness of a CVD treatment in a subject according to the disclosure may further comprise after the determining step and/or the step of assaying the at least one additional Cer and/or the at least one additional PC biomarker, changing, supplementing, or keeping the same an already administered treatment in the subject based on the Cer concentration(s) and/or PC concentration(s) obtained in the determining step and/or the step of assaying the at least one additional Cer and/or at least one additional PC biomarker.

In certain embodiments, the method of evaluating the effectiveness of a CVD treatment in a subject, further comprises determining that the treatment is not effective in the subject and escalating the treatment of the subject or changing to a different treatment.

In certain embodiments, the escalation of the treatment regimen is as prescribed in relevant guidelines such that a subject will be moved to the next recommended tier based on an unfavorable change in concentration of the at least one Cer of Formula I and/or the at least one PC of Formula II obtained in the determining step.

In certain embodiments, the treatment regimen determined to be ineffective comprises the administration of a drug, such as a lipid lowering drug, as described herein (e.g. a statin). In certain embodiments, the relevant guidelines comprise increasing the dosage or the type of drug administered to the subject in comparison to the dosage or the type of drug administered before the determining step.

In another aspect, the present disclosure is directed to a method of treating CVD or preventing one or more CV events in a subject undergoing treatment for CVD, such as coronary artery disease or atherosclerosis, the method comprising administering to the subject a drug, such as a lipid lowering drug, as described herein, and/or providing therapeutic, behavioral and/or lifestyle modification, wherein, prior to administering the drug, the subject has been identified as being ineffectively treated for CVD by a method for evaluating the effectiveness of a treatment as described herein.

In another aspect, the present disclosure is directed to a method of treating CVD or preventing one or more CV events in a subject undergoing treatment for CVD, such as coronary artery disease or atherosclerosis, the method comprising determining whether the subject is being ineffectively treated for CVD according to a method for evaluating the effectiveness of a treatment as described herein, and administering to the subject a drug, such as a lipid lowering drug, and/or providing therapeutic, behavioral and/or lifestyle modification, if the subject has been identified as being ineffectively treated for CVD.

In another aspect of the disclosure, a method is provided for choosing an appropriate CVD treatment for a subject, the method comprising assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject being in need of a treatment or a change in, or supplementation of, an already administered treatment.

In certain embodiments of the method of choosing an appropriate CVD treatment for a subject as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject being in need of a treatment or a change in, or supplementation of, an already administered treatment.

In certain embodiments, the method provided for choosing an appropriate CVD treatment for a subject further comprises after the determining step and/or after the step of assaying the at least one additional Cer and/or the at least one additional PC biomarker, treating the subject and/or providing therapeutic, behavioral and/or lifestyle modification to the subject based on the Cer concentration(s) and/or PC concentration(s) obtained in the determining step.

In certain embodiments, the method of choosing an appropriate CVD treatment for a subject, further comprises after the determining step and/or after the step of assaying the at least one additional Cer and/or the at least one additional PC biomarker, determining that the subject is in need of a treatment or a change in, or a supplementation of, an already administered treatment, and administering to the subject the treatment that the subject is determined to be in need of and/or providing therapeutic, behavioral and/or lifestyle modification to the subject.

In certain embodiments, the CVD treatment, the effectiveness of which is to be evaluated or which is to be chosen as appropriate in accordance with the methods described and claimed herein, is a lipid modifying treatment (e.g., statin or other lipid lowering drug as described elsewhere in this application).

In another aspect, the present disclosure is directed to a method of treating CVD or preventing one or more CV events in a subject comprising administering to the subject a drug, such as a lipid lowering drug, as described herein, and/or providing therapeutic, behavioral and/or lifestyle modification, wherein, prior to administering the drug and/or providing therapeutic, behavioral and/or lifestyle modification, the subject has been identified as being in need of a change in, or supplementation of an already administered treatment by a method of choosing an appropriate CVD treatment as described herein.

In another aspect, the present disclosure is directed to a method of treating CVD or preventing one or more CV events in a subject comprising determining whether the subject needs a change in, or supplementation of an already administered treatment according to a method of choosing an appropriate treatment as described herein, and administering to the subject a drug, such as a lipid lowering drug, as described herein, if the subject has been identified as needing a change in, or supplementation of the already administered treatment.

Another aspect of the disclosure relates to a method of treating CVD or preventing one or more CV events in a subject comprising administering to the subject a therapeutically effective dose of a drug, wherein the drug is a statin; a lipid lowering drug selected from an HMG-CoA reductase inhibitor other than a statin, niacin (nicotinic acid), a cholesterol absorption inhibitor (e.g. ezetimibe), a cholesteryl ester transfer protein (CETP), a bile acid sequestrant, a fibrate, a phytosterol, an anti-inflammatory drug (e.g. methotrexate, IL-1 mAb, TNF-alpha mAb), acetylsalicylic acid (aspirin), and a PCSK9 inhibitor; or a modulator of lipid concentrations selected from a small molecule, an antibody, an antisense RNA, a small interfering RNA (siRNA), and a natural or modified lipid, and wherein before administering the drug the subject has been identified as having a risk of developing one or more CV events based on a method disclosed herein.

According to any of the aspects and embodiments of the present disclosure, the subject may be treated or has been treated with a statin, another lipid lowering drug, and/or a modulator of lipid concentrations. Alternatively, the subject may also be one that has not yet undergone statin therapy, therapy with another lipid lowering drug, and/or therapy with a modulator of lipid concentrations.

In some embodiments, the treatment or prevention method further comprises identifying the subject as in need of the treatment or prevention, for example, by requesting a test, for example, from a commercial laboratory, which provides the results of an assay useful for determining the concentration(s) of the at least one Cer of Formula I and/or the at least one PC of Formula II and administering to the subject a treatment, for example, a therapeutically effective dose of a drug and/or therapeutic, behavioral and/or lifestyle modification, if the subject has an increased concentration of the at least one Cer of Formula I and/or a decreased concentration of the at least one PC of Formula II, as compared to a control sample.

In yet another aspect of the present disclosure, a method is provided for collecting data for determining the risk of a subject to develop one or more cardiovascular events, the method comprising assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the method of collecting data as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 phosphatidylcholines of Formula II.

In certain embodiments, the method further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events.

In another aspect of the disclosure, a method is provided for collecting data for detecting in a sample from a subject a concentration of at least one ceramide (Cer) of Formula I and a concentration of at least one phosphatidylcholine (PC) of Formula II.

In certain embodiments of the method of collecting data for detecting as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises detecting in the sample a concentration of at least one additional Cer and/or at least one additional PC biomarker selected from any of the Cer and PC species referred to in Table 1.

In another aspect of the disclosure, a method is provided for collecting data for evaluating the effectiveness of a CVD treatment in a subject, the method comprising assaying a sample from the subject to determine a concentration of at least one ceramide (Cer) of Formula I and a concentration of at least one phosphatidylcholine (PC) of Formula II, wherein (a) decreased concentration(s) of the at least one Cer of Formula I and/or (an) increased concentration(s) of the at least one PC of Formula II in the sample, when compared to a control, is (are) indicative of the effectiveness of said treatment.

In certain embodiments of the method of collecting data for evaluating the effectiveness of a CVD treatment as described herein the at least one Cer of Formula I is at least 2, at least 3, at least 4, at least 5, at least 6, at least 7, at least 8, at least 9 or at least 10 ceramides of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC, when compared to a control, is (are) indicative of the effectiveness of said treatment.

In another aspect of the disclosure, a method is provided for collecting data for choosing an appropriate CVD treatment for a subject, the method comprising assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject being in need of a treatment or a change in, or supplementation of, an already administered treatment.

In certain embodiments of the method of collecting data for choosing an appropriate CVD treatment as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject being in need of a treatment or a change in, or supplementation of, an already administered treatment.

In another aspect of the disclosure, a cardiovascular disease (CVD) marker combination is provided for determining the risk of a subject to develop one or more cardiovascular events, the CVD marker combination comprising at least one ceramide (Cer) of Formula I and at least one phosphatidylcholine (PC) of Formula II.

In certain embodiments of the CVD marker combination as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the CVD marker combination further comprises at least one additional Cer and/or at least one additional PC biomarker, selected from any of the Cer and PC species referred to in Table 1.

In another aspect of the disclosure, a use of a CVD marker combination is provided for determining the risk of a subject to develop one or more cardiovascular events, wherein the CVD marker combination comprises at least one ceramide (Cer) of Formula I and at least one phosphatidylcholine (PC) of Formula II, and wherein the use comprises assaying a sample from the subject to determine a concentration of at least one Cer of Formula I and a concentration of at least one PC of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the use of the CVD marker combination for determining the risk of a subject to develop one or more cardiovascular events as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II wherein the CVD marker combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use of the CVD marker combination further comprises assaying a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events, and wherein the CVD marker combination further comprises at least one additional Cer and/or at least one additional PC biomarker, selected from any of the Cer and PC species referred to in Table 1.

In another aspect of the disclosure, a use of a CVD marker combination is provided for detecting in a sample from a subject a concentration of at least one ceramide (Cer) of Formula I and a concentration of at least one phosphatidylcholine (PC) of Formula II.

In certain embodiments of the use of the CVD marker combination for detecting as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the use further comprises detecting in the sample a concentration of at least one additional Cer and/or at least one additional PC biomarker, selected from any of the Cer and PC species referred to in Table 1.

In certain embodiments, the use comprises detecting in a sample from a subject a changed concentration of at least one Cer of Formula I and/or a changed concentration of at least one PC of Formula II, e.g., as compared to a control.

In certain embodiments, the use comprises detecting in a sample from a subject an increased concentration of at least one Cer of Formula I and/or a decreased concentration of at least one PC of Formula II.

In another aspect of the disclosure, a use of a CVD marker combination is provided for obtaining data for determining the risk of a subject to develop one or more CV events, wherein the CVD marker combination comprises at least one ceramide (Cer) of Formula I and at least one phosphatidylcholine (PC) of Formula II, and wherein the use comprises assaying a sample from the subject to determine a concentration of at least one Cer of Formula I and a concentration of at least one PC of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the use of the CVD marker combination for obtaining data as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II and wherein the CVD marker combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events, and wherein the CVD marker combination further comprises at least one additional Cer and/or at least one additional PC biomarker, selected from any of the Cer and PC species referred to in Table 1.

In another aspect of the disclosure, a use of a CVD marker combination is provided for evaluating the effectiveness of a CVD treatment in a subject, wherein the CVD marker combination comprises at least one ceramide (Cer) of Formula I and at least one phosphatidylcholine (PC) of Formula II, and wherein the use comprises assaying a sample from the subject to determine a concentration of at least one ceramide (Cer) of Formula I and a concentration of at least one phosphatidylcholine (PC) of Formula II, wherein (a) decreased concentration(s) of the at least one Cer of Formula I and/or (an) increased concentration(s) of the at least one PC of Formula II in the sample, when compared to a control, is (are) indicative of the effectiveness of said treatment.

In certain embodiments of the use of the CVD marker combination for evaluating the effectiveness of a CVD treatment as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II and wherein the CVD marker combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC, when compared to a control, is (are) indicative of the effectiveness of said treatment, and wherein the CVD marker combination further comprises at least one additional Cer and/or at least one additional PC biomarker, selected from any of the Cer and PC species referred to in Table 1.

In another aspect of the disclosure, a use of a CVD marker combination is provided for choosing an appropriate CVD treatment for a subject, wherein the CVD marker combination comprises at least one ceramide (Cer) of Formula I and at least one phosphatidylcholine (PC) of Formula II, and wherein the use comprises assaying a sample from the subject to determine a concentration of at least one Cer of Formula I and a concentration of at least one PC of Formula II, wherein (an) increased concentration(s) of the at least one Cer of Formula I and/or (a) decreased concentration(s) of the at least one PC of Formula II in the sample, when compared to a control, is (are) indicative of the subject being in need of a treatment or a change in, or supplementation of, an already administered treatment.

In certain embodiments of the use of the CVD marker combination for choosing an appropriate CVD treatment as described herein the at least one Cer of Formula I is at least 2, at least 3, at least 4, at least 5, at least 6, at least 7, at least 8, at least 9 or at least 10 Cers of Formula I and/or the at least one PCs of Formula II is at least 2, at least 3, at least 4, at least 5, at least 6, at least 7, at least 8, at least 9 or at least 10 PCs of Formula II and wherein the CVD marker combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker selected from any of the Cer and PC species referred to in Table 1, wherein (an) increased or decreased concentration(s) of the at least one additional Cer and/or the at least one additional PC as indicated in Table 1, when compared to a control, is (are) indicative of the subject being in need of a treatment or a change in, or supplementation of, an already administered treatment, and wherein the CVD marker combination further comprises at least one additional Cer and/or a least one additional PC biomarker selected from any of the Cer and PC species referred to in Table 1.

In another aspect of the disclosure, a standard combination is provided for determining the risk of a subject to develop one or more cardiovascular events, the standard combination comprising at least one ceramide (Cer) of Formula I and at least one phosphatidylcholine (PC) of Formula II.

In certain embodiments, the standard combination comprises at least one isotope-labelled Cer of Formula I and/or at least one isotope-labelled PC of Formula II.

In certain embodiments, the isotope of the at least one isotope-labelled Cer of Formula I and/or the at least one isotope-labelled PC of Formula II is deuterium, $^{13}C$ or $^{15}N$.

In certain embodiments of the standard combination as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments of the standard combination as described herein the at least one, at least 2, at least 3, at least 4, at least 5, at least 6, at least 7, at least 8, at least 9 or the at least 10 Cers of Formula I is/are isotope-labelled Cers of Formula I and/or the at least one, at least 2, at least 3, at least 4, at least 5, at least 6, at least 7, at least 8, at least 9 or at least 10 PCs of Formula II is/are isotope-labelled PCs of Formula II.

In certain embodiments, the isotope of the at least one, at least 2, at least 3, at least 4, at least 5, at least 6, at least 7, at least 8, at least 9 or at least 10 isotope-labelled Cers of Formula I and/or the isotope of the at least one, at least 2, at least 3, at least 4, at least 5, at least 6, at least 7, at least 8, at least 9 or at least 10 isotope-labelled PCs of Formula II is deuterium, $^{13}C$ or $^{15}N$.

In certain embodiments, the standard combination further comprises at least one additional Cer and/or at least one additional PC, selected from any of the Cer and PC species referred to in Table 1.

In certain embodiments, the at least one additional Cer and/or the at least one additional PC selected from any of the Cer and PC species referred to in Table 1, is isotope-labelled.

In certain embodiments, the isotope of the at least one additional isotope-labelled Cer and/or the at least one additional isotope-labelled PC selected from any of the Cer and PC species referred to in Table 1, is deuterium, $^{13}C$ or $^{15}N$.

In another aspect of the disclosure, a standard combination is provided for assaying a concentration of at least one ceramide (Cer) of Formula I and a concentration of at least one phosphatidylcholine (PC) of Formula II in a sample from a subject in a preparation of a reagent, kit or composition for determining the risk of the subject to develop one or more cardiovascular events, wherein the standard combination comprises at least one Cer of Formula I and at least one PC of Formula II.

In certain embodiments of the standard combination for assaying as described herein, the at least one Cer of Formula I and/or the at least one PC of Formula II is isotope-labelled.

In certain embodiments, the isotope of the at least one isotope-labelled Cer of Formula I and/or the at least one isotope-labelled PC of Formula II is deuterium, $^{13}C$ or $^{15}N$.

In certain embodiments of the standard combination for assaying as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments of the standard combination for assaying as described herein the at least 2, at least 3, at least 4, at least 5, at least 6, at least 7, at least 8, at least 9 or at least 10 Cers of Formula I is/are isotope-labelled and/or the at least 2, at least 3, at least 4, at least 5, at least 6, at least 7, at least 8, at least 9 or at least 10 PCs of Formula II is/are isotope-labelled.

In certain embodiments, the isotope of the at least 2, at least 3, at least 4, at least 5, at least 6, at least 7, at least 8, at least 9 or at least 10 isotope-labelled Cers of Formula I and/or the isotope of the at least 2, at least 3, at least 4, at least 5, at least 6, at least 7, at least 8, at least 9 or at least 10 isotope-labelled PCs of Formula II is/are deuterium, $^{13}C$ or $^{15}N$.

In certain embodiments, the standard combination further comprises at least one additional Cer and/or at least one additional PC selected from any of the Cer and PC species referred to in Table 1.

In certain embodiments, the at least one additional Cer and/or the at least one additional PC selected from any of the Cer and PC species referred to in Table 1, is/are isotope-labelled.

In certain embodiments, the isotope of the at least one additional isotope-labelled Cer and/or the isotope of the at least one additional isotope-labelled PC selected from any of the Cer and PC species referred to in Table 1, is/are deuterium, $^{13}C$ or $^{15}N$.

In another aspect of the disclosure, a standard combination is provided for assaying a concentration of at least one ceramide (Cer) of Formula I and a concentration of at least one phosphatidylcholine (PC) of Formula II in a sample from a subject in a preparation of a reagent, kit or composition for evaluating the effectiveness of a CVD treatment in the subject, wherein the standard combination comprises at least one Cer of Formula I and at least one PC of Formula II.

In certain embodiments of the standard combination for assaying and evaluating effectiveness as described herein, the at least one Cer of Formula I and/or the at least one PC of Formula II is isotope-labelled.

In certain embodiments, the isotope of the at least one isotope-labelled Cer of Formula I and/or the at least one isotope-labelled PC of Formula II is deuterium, $^{13}C$ or $^{15}N$.

In certain embodiments of the standard combination for assaying and evaluating effectiveness as described herein, the at least one Cer of Formula I is at least 2, at least 3, at least 4, at least 5, at least 6, at least 7, at least 8, at least 9 or at least 10 Cers of Formula I and/or the at least one PC of Formula I is at least 2, at least 3, at least 4, at least 5, at least 6, at least 7, at least 8, at least 9 or at least 10 PCs of Formula II.

In certain embodiments of the standard combination for assaying and evaluating effectiveness as described herein, the at least 2, at least 3, at least 4, at least 5, at least 6, at least 7, at least 8, at least 9 or at least 10 Cers of Formula I is/are isotope-labelled and/or the at least 2, at least 3, at least 4, at least 5, at least 6, at least 7, at least 8, at least 9 or at least 10 PCs of Formula II is/are isotope-labelled.

In certain embodiments, the isotope of the at least 2, at least 3, at least 4, at least 5, at least 6, at least 7, at least 8, at least 9 or at least 10 isotope-labelled Cers of Formula I and/or the isotope of the at least 2, at least 3, at least 4, at least 5, at least 6, at least 7, at least 8, at least 9 or at least 10 isotope-labelled PCs of Formula II is/are deuterium, $^{13}C$ or $^{15}N$.

In certain embodiments, the standard combination further comprises at least one additional Cer and/or at least one additional PC, selected from any of the Cer and PC species referred to in Table 1.

In certain embodiments, the at least one additional Cer and/or the at least one additional PC, selected from any of the Cer and PC species referred to in Table 1, is isotope-labelled.

In certain embodiments, the isotope of the at least one additional isotope-labelled Cer and/or the at least one additional isotope-labelled PC, selected from any of the Cer and PC species referred to in Table 1, is deuterium, $^{13}C$ or $^{15}N$.

In another aspect of the disclosure, a standard combination is provided for assaying a concentration of at least one ceramide (Cer) of Formula I and a concentration of at least one phosphatidylcholine (PC) of Formula II in a sample from a subject in a preparation of a reagent, kit or composition for choosing an appropriate CVD treatment for the subject, wherein the standard combination comprises at least one Cer of Formula I and at least one PC of Formula II.

In certain embodiments of the standard combination for assaying and choosing an appropriate CVD treatment as described herein, the at least one Cer of Formula I and/or the at least one PC of Formula II is isotope-labelled.

In certain embodiments, the isotope of the at least one isotope-labelled Cer of Formula I and/or the isotope of the at least one isotope-labelled PC of Formula II is deuterium, $^{13}C$ or $^{15}N$.

In certain embodiments of the standard combination for assaying and choosing an appropriate CVD treatment as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments of the standard combination for assaying and choosing an appropriate CVD treatment as described herein, the at least 2, at least 3, at least 4, at least 5, at least 6, at least 7, at least 8, at least 9 or at least 10 Cers of Formula I is/are isotope-labelled and/or the at least 2, at least 3, at least 4, at least 5, at least 6, at least 7, at least 8, at least 9 or at least 10 PCs of Formula II is/are isotope-labelled.

In certain embodiments, the isotope of the at least 2, at least 3, at least 4, at least 5, at least 6, at least 7, at least 8, at least 9 or at least 10 isotope-labelled Cers of Formula I and/or the isotope of the at least 2, at least 3, at least 4, at least 5, at least 6, at least 7, at least 8, at least 9 or at least 10 isotope-labelled PCs of Formula II is/are deuterium, $^{13}C$ or $^{15}N$.

In certain embodiments, the standard combination further comprises at least one additional Cer and/or at least one additional PC, selected from any of the Cer and PC species referred to in Table 1.

In certain embodiments, the at least one additional Cer and/or the at least one additional PC, selected from any of the Cer and PC species referred to in Table 1, is isotope-labelled.

In certain embodiments, the isotope of the at least one additional isotope-labelled Cer and/or the at least one additional isotope-labelled PC, selected from any of the Cer and PC species referred to in Table 1, is deuterium, $^{13}C$ or $^{15}N$.

In another aspect of the disclosure, a use of a standard combination is provided for determining the risk of a subject to develop one or more cardiovascular events, wherein the standard combination comprises at least one ceramide (Cer) of Formula I and at least one phosphatidylcholine (PC) of Formula II, and wherein the use comprises assaying a sample from the subject to determine a concentration of at least one Cer of Formula I and a concentration of at least one PC of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the use of the standard combination for determining the risk as described herein, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II, and wherein the standard combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use of the standard combination further comprises assaying a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events, and wherein the standard combination further comprises at least one additional Cer and/or at least one additional PC, selected from any of the Cer and PC species referred to in Table 1.

In another aspect of the disclosure, a use of a standard combination is provided for detecting in a sample from a subject a concentration of at least one ceramide (Cer) of Formula I and a concentration of at least one phosphatidylcholine (PC) of Formula II, wherein the standard combination comprises at least one Cer of Formula I and at least one PC of Formula II.

In certain embodiments, of the use of the standard combination for detecting as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II, wherein the standard combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use further comprises detecting in the sample a concentration of at least one additional Cer and/or at least one additional PC selected from any of the Cer and PC species referred to in Table 1, wherein the standard combination further comprises at least one additional Cer and/or at least one additional PC selected from any of the Cer and PC species referred to in Table 1.

In certain embodiments, the use comprises detecting in a sample from a subject a changed concentration of the at least one Cer of Formula I and/or a changed concentration of the at least one PC of Formula II.

In certain embodiments, the use comprises detecting in a sample from a subject an increased concentration of the at least one Cer of Formula I and/or a decreased concentration of the at least one PC of Formula II.

In another aspect of the disclosure, a use of a standard combination is provided for obtaining data for determining the risk of a subject to develop one or more CV events, wherein the standard combination comprises at least one ceramide (Cer) of Formula I and at least one phosphatidylcholine (PC) of Formula II, and wherein the use comprises assaying a sample from the subject to determine a concentration of at least one Cer of Formula I and a concentration of at least one PC of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the use of the standard combination for obtaining data as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II, and wherein the standard combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events, and wherein the standard combination further comprises at least one additional Cer and/or least one additional PC selected from any of the Cer and PC species referred to in Table 1.

In another aspect of the disclosure, a use of a standard combination is provided for evaluating the effectiveness of a CVD treatment in a subject, wherein the standard combination comprises at least one ceramide (Cer) of Formula I and at least one phosphatidylcholine (PC) of Formula II, and wherein the use comprises assaying a sample from the subject to determine a concentration of at least one Cer of Formula I and a concentration of at least one PC of Formula II, wherein (a) decreased concentration(s) of the at least one Cer of Formula I and/or (an) increased concentration(s) of the at least one PC of Formula II in the sample, when compared to a control, is (are) indicative of the effectiveness of said treatment.

In certain embodiments of the use of the standard combination for evaluating the effectiveness of the CVD treatment as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II, and wherein the standard combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC, when compared to a control, is (are) indicative of the effectiveness of said treatment, and wherein the standard combination further comprises at least one additional Cer and/or at least one additional PC, selected from any of the Cer and PC species referred to in Table 1.

In another aspect of the disclosure, a use of a standard combination is provided for choosing an appropriate CVD treatment for a subject, wherein the standard combination comprises at least one ceramide (Cer) of Formula I and at least one phosphatidylcholine (PC) of Formula II, and wherein the use comprises assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject being in need of a treatment or a change in, or supplementation of, an already administered treatment.

In certain embodiments of the use of the standard combination for choosing the appropriate CVD treatment as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II, and wherein the standard combination comprises at least one, at least 2, at least 3, at least 4, at least 5, at least 6, at least 7, at least 8, at least 9 or at least 10 Cers of Formula I and/or at least one, at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject being in need of a treatment or a change in, or supplementation of, an already administered treatment, and wherein the standard combination further comprises at least one additional Cer and/or at least one additional PC selected from any of the Cer and PC species referred to in Table 1.

In certain embodiments of all aspects of the disclosure, the standard combination comprises at least one isotope-labelled Cer of Formula I and/or at least one isotope-labelled PC of Formula II.

In certain embodiments of all aspects of the disclosure, the isotope of the at least one isotope-labelled Cer of Formula I and/or the at least one isotope-labelled PC of Formula II is deuterium, $^{13}C$ or $^{15}N$.

In certain embodiments of all aspects of the disclosure, the standard combination comprises at least one, at least 2, at least 3, at least 4, at least 5, at least 6, at least 7, at least 8, at least 9 or at least 10 isotope-labelled Cers of Formula I and/or at least one, at least 2, at least 3, at least 4, at least 5, at least 6, at least 7, at least 8, at least 9 or at least 10 isotope-labelled PCs of Formula II.

In certain embodiments of all aspects of the disclosure, the isotope of the at least one, at least 2, at least 3, at least 4, at least 5, at least 6, at least 7, at least 8, at least 9 or at least 10 isotope-labelled Cers of Formula I and/or the isotope of the at least one, at least 2, at least 3, at least 4, at least 5, at least 6, at least 7, at least 8, at least 9 or at least 10 isotope-labelled PCs of Formula II is/are deuterium, $^{13}$C or $^{15}$N.

In certain embodiments of all aspects of the disclosure, the at least one additional Cer and/or the at least one additional PC, selected from any of the Cer and PC species referred to in Table 1, is isotope-labelled.

In certain embodiments of all aspects of the disclosure, the isotope of the at least one additional isotope-labelled Cer and/or the at least one additional isotope-labelled PC, selected from any of the Cer and PC species referred to in Table 1, is/are deuterium, $^{13}$C or $^{15}$N.

In certain embodiments of all aspects of the disclosure, the standard combination comprises at least one, at least 2, at least 3, at least 4, at least 5, at least 6, at least 7, at least 8, at least 9 or at least 10 isotope-labelled Cers and/or at least one, at least 2, at least 3, at least 4, at least 5, at least 6, at least 7, at least 8, at least 9 or at least 10 isotope-labelled PCs selected from the following isotope-labelled lipids: Cer(d18:1/16:0), Cer(d18:1/18:0), Cer(d18:1/22:0), Cer(d18:1/24:0), Cer(d18:1/24:1), Cer(d18:1/26:0), Cer(d18:1/26:1), Cer(d16:1/16:0), Cer(d16:1/18:0), Cer(d16:1/24:0), Cer(d16:1/24:1), Cer(d18:2/16:0), Cer(d18:2/18:0), Cer(d18:2/24:1), Cer(d18:2/24:0), Cer(d20:1/24:1), PC 16:0/22:5, PC 14:0/22:6, PC 16:0/16:0, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8.

In certain embodiments of all aspects of the present disclosure, the at least one, at least 2, at least 3, at least 4, at least 5, at least 6 or at least 7 isotope-labelled lipid(s) of the standard combination is (are) selected from the following isotope-labelled lipids: Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled lipids of the standard combination are Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled lipids Cer(d18:1/16:0), Cer(d18:1/18:0), Cer(d18:1/24:0), Cer(d18:1/24:1), PC 16:0/22:5, PC 14:0/22:6 and/or PC 16:0/16:0 of the standard combination are deuterium-labelled.

In certain embodiments of all aspects of the present disclosure, the isotope-labelled lipid(s) of the standard combination is (are) d7-Cer(d18:1/16:0), d7-Cer(d18:1/18:0), d7-Cer(d18:1/24:0), d7-Cer(d18:1/24:1), d9-PC 16:0/22:5, d9-PC 14:0/22:6 and/or d9-PC 16:0/16:0.

In another aspect of the disclosure, a use of one or more reagent(s) in a preparation of a reagent, kit or composition is provided for determining the risk of a subject to develop one or more cardiovascular events, comprising assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the use of the one or more reagent(s) for determining the risk as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject having a risk of developing one or more cardiovascular events.

In another aspect of the disclosure, a use of one or more reagent(s) in a preparation of a reagent, kit or composition is provided for detecting in a sample from a subject a concentration of at least one ceramide (Cer) of Formula I and a concentration of at least one phosphatidylcholine (PC) of Formula II.

In certain embodiments of the use of the one or more reagent(s) for detecting as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the use further comprises detecting in the sample a concentration of at least one additional Cer and/or at least one additional PC biomarker, selected from any of the Cer and PC species referred to in Table 1.

In certain embodiments, the use of the one or more reagent(s) for detecting as described herein comprises detecting in a sample from a subject a changed concentration of at least one Cer of Formula I and/or a changed concentration of at least one PC of Formula II.

In certain embodiments, the use comprises detecting in a sample from a subject an increased concentration of at least one Cer of Formula I and/or a decreased concentration of at least one PC of Formula II.

In certain embodiments, the use of one or more reagent(s) in a preparation of a reagent, kit or composition for detecting in a sample from a subject a concentration of at least one ceramide of Formula I and a concentration of at least one phosphatidylcholine of Formula II comprises using a standard combination comprising at least one Cer of Formula I and/or at least one PC of Formula II.

In another aspect of the disclosure, a use of one or more reagent(s) in a preparation of a reagent, kit or composition is provided for obtaining data for determining the risk of a subject to develop one or more CV events, the use comprising assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject having a risk of developing one or more cardiovascular events.

In certain embodiments of the use of the one or more reagents for obtaining data as described herein, the at least one Cer of Formula I is at least 2, at least 3, at least 4, at least 5, at least 6, at least 7, at least 8, at least 9 or at least 10 Cers of Formula I and/or the at least one PC of Formula I is at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or at least one additional PC as indicated in Table 1, when compared to a control, is (are) indicative of the subject having a risk of developing one or more cardiovascular events.

In another aspect of the disclosure, a use of one or more reagent(s) in a preparation of a reagent, kit or composition is provided for evaluating the effectiveness of a CVD treatment in a subject, the use comprising assaying a sample from the subject to determine a concentration of at least one ceramide (Cer) of Formula I and a concentration of at least one phosphatidylcholine (PC) of Formula II, wherein (a) decreased concentration(s) of the at least one Cer of Formula I and/or (an) increased concentration(s) of the at least one PC of Formula II in the sample, when compared to a control, is (are) indicative of the effectiveness of said treatment.

In certain embodiments of the use of the one or more reagent(s) for evaluating the effectiveness of a CVD treatment as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC, when compared to a control, is (are) indicative of the effectiveness of said treatment.

In another aspect of the disclosure, a use of one or more reagent(s) in a preparation of a reagent, kit or composition is provided for choosing an appropriate CVD treatment for a subject, the method comprising assaying a sample from the subject to determine a concentration of at least one ceramide (Cer) of Formula I and a concentration of at least one phosphatidylcholine (PC) of Formula II, wherein (an) increased concentration(s) of the at least one Cer of Formula I and/or (a) decreased concentration(s) of the at least one PC of Formula II in the sample, when compared to a control, is (are) indicative of the subject being in need of a treatment or a change in, or supplementation of, an already administered treatment.

In certain embodiments of the use of the one or more reagent(s) for choosing an appropriate CVD treatment as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the use further comprises assaying the sample to determine a concentration of at least one additional Cer and/or at least one additional PC biomarker, selected from any of the Cer and PC species referred to in Table 1, wherein (an) increased or decreased concentration(s) of the at least one additional Cer and/or the at least one additional PC as indicated in Table 1, when compared to a control, is (are) indicative of the subject being in need of a treatment or a change in, or supplementation of, an already administered treatment.

In certain embodiments, the reagent comprises any standard(s), control(s), substance(s), compound(s), solution(s), solvent(s), agent(s), ingredient(s), preparation(s), or any combination thereof used for the methods and uses of the present disclosure. In certain embodiments, the reagent is a combination or mixture of any standard(s), control(s), substance(s), compound(s), solution(s), solvent(s), agent(s), ingredient(s) and preparation(s) used in the methods and uses of the present disclosure.

In some embodiments, one or more of any components of a reagent is isotope-labelled. In some embodiments, the isotope of the isotope-labelled component is deuterium, $^{13}C$ or $^{15}N$.

In certain embodiments of all aspects of the disclosure, the reagent comprises at least one, at least 2, at least 3, at least 4, at least 5, at least 6, at least 7, at least 8, at least 9 or at least 10 isotope-labelled Cers and/or at least one, at least 2, at least 3, at least 4, at least 5, at least 6, at least 7, at least 8, at least 9 or at least 10 isotope-labelled PCs selected from the following isotope-labelled lipids: Cer(d18:1/16:0), Cer(d18:1/18:0), Cer(d18:1/22:0), Cer(d18:1/24:0), Cer(d18:1/24:1), Cer(d18:1/26:0), Cer(d18:1/26:1), Cer(d16:1/16:0), Cer(d16:1/18:0), Cer(d16:1/24:0), Cer(d16:1/24:1), Cer(d18:2/16:0), Cer(d18:2/18:0), Cer(d18:2/24:1), Cer(d18:2/24:0), Cer(d20:1/24:1), PC 16:0/22:5, PC 14:0/22:6, PC 16:0/16:0, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8.

In certain embodiments of all aspects of the present disclosure, the at least one, at least 2, at least 3, at least 4, at least 5, at least 6 or at least 7 isotope-labelled lipid(s) of the reagent is (are) selected from the following isotope-labelled lipids: Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled lipids of the reagent are Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled lipids Cer(d18:1/16:0), Cer(d18:1/18:0), Cer(d18:1/24:0), Cer(d18:1/24:1), PC 16:0/22:5, PC 14:0/22:6 and/or PC 16:0/16:0 of the reagent are deuterium-labelled.

In certain embodiments of all aspects of the present disclosure, the isotope-labelled lipid(s) of the reagent is (are) d7-Cer(d18:1/16:0), d7-Cer(d18:1/18:0), d7-Cer(d18:1/24:0), d7-Cer(d18:1/24:1), d9-PC 16:0/22:5, d9-PC 14:0/22:6 and/or d9-PC 16:0/16:0.

In certain embodiments, the reagent is used for assaying a sample to determine a concentration of at least one ceramide (Cer) of Formula I and a concentration of at least one phosphatidylcholine (PC) of Formula II. In some embodiments, a reagent is further used for assaying a sample to determine a concentration of at least one additional Cer and/or PC, selected from any of the Cer and PC species referred to in Table 1 of the present disclosure.

In certain embodiments, the reagent is used in a preparation of a reagent, kit or composition which are used for performing the methods and uses of the present disclosure.

In another aspect of the disclosure, a composition or kit is provided for diagnosing, predicting or detecting one or more cardiovascular events in a subject or for performing any of the methods or uses according to the present disclosure, the composition or kit comprising at least one ceramide (Cer) of Formula I and at least one phosphatidylcholine (PC) of Formula II.

In certain embodiments of the composition or kit, the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the composition or kit further comprises at least one additional Cer and/or at least one additional PC, selected from any of the Cer and PC species referred to in Table 1.

In certain embodiments, the composition or kit comprises at least one isotope-labelled Cer of Formula I and/or at least one isotope-labelled PC of Formula II.

In certain embodiments, the isotope of the at least one isotope-labelled Cer of Formula I and/or the at least one isotope-labelled PC of Formula II is deuterium, $^{13}C$ or $^{15}N$.

In certain embodiments of the composition or kit, the at least one isotope-labelled Cer of Formula I is at least 2, at least 3, at least 4, at least 5, at least 6, at least 7, at least 8, at least 9 or at least 10 isotope-labelled Cers of Formula I and/or the at least one isotope-labelled PC of Formula II is at least 2, at least 3, at least 4, at least 5, at least 6, at least 7, at least 8, at least 9 or at least 10 isotope-labelled PCs of Formula II.

In certain embodiments, the isotope of the at least one, at least 2, at least 3, at least 4, at least 5, at least 6, at least 7, at least 8, at least 9 or at least 10 isotope-labelled Cers of Formula I and/or the at least one, at least 2, at least 3, at least 4, at least 5, at least 6, at least 7, at least 8, at least 9 or at least 10 isotope-labelled PCs of Formula II is/are deuterium, $^{13}C$ or $^{15}N$.

In certain embodiments, the composition or kit comprises at least one additional isotope-labelled Cer and/or at least one additional isotope-labelled PC, selected from any of the Cer and PC species referred to in Table 1.

In certain embodiments, the isotope of the at least one additional isotope-labelled Cer and/or the at least one additional isotope-labelled PC, selected from any of the Cer and PC species referred to in Table 1, is/are deuterium, $^{13}C$ or $^{15}N$.

In certain embodiments of all aspects of the disclosure, the composition or kit comprises at least one, at least 2, at least 3, at least 4, at least 5, at least 6, at least 7, at least 8, at least 9 or at least 10 isotope-labelled Cers and/or at least one, at least 2, at least 3, at least 4, at least 5, at least 6, at least 7, at least 8, at least 9 or at least 10 isotope-labelled PCs selected from the following isotope-labelled lipids: Cer(d18:1/16:0), Cer(d18:1/18:0), Cer(d18:1/22:0), Cer(d18:1/24:0), Cer(d18:1/24:1), Cer(d18:1/26:0), Cer(d18:1/26:1), Cer(d16:1/16:0), Cer(d16:1/18:0), Cer(d16:1/24:0), Cer(d16:1/24:1), Cer(d18:2/16:0), Cer(d18:2/18:0), Cer(d18:2/24:1), Cer(d18:2/24:0), Cer(d20:1/24:1), PC 16:0/22:5, PC 14:0/22:6, PC 16:0/16:0, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8.

In certain embodiments of all aspects of the present disclosure, the at least one, at least 2, at least 3, at least 4, at least 5, at least 6 or at least 7 isotope-labelled lipid(s) of the composition or kit is (are) selected from the following isotope-labelled lipids: Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled lipids of the composition or kit are Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled lipids Cer(d18:1/16:0), Cer(d18:1/18:0), Cer(d18:1/24:0), Cer(d18:1/24:1), PC 16:0/22:5, PC 14:0/22:6 and/or PC 16:0/16:0 of the composition or kit are deuterium-labelled.

In certain embodiments of all aspects of the present disclosure, the isotope-labelled lipid(s) of the composition or kit is (are) d7-Cer(d18:1/16:0), d7-Cer(d18:1/18:0), d7-Cer(d18:1/24:0), d7-Cer(d18:1/24:1), d9-PC 16:0/22:5, d9-PC 14:0/22:6 and/or d9-PC 16:0/16:0. The composition or kit may further include standard(s), control(s), reagent(s), solution(s), solvent(s), container(s), use instruction(s) for the methods or uses disclosed herein, and/or other element(s) for performing the methods or uses disclosed herein.

In some embodiments, the composition or kit includes element(s) for collecting a blood sample, for example, a dried blood spot on a filter.

The composition or kit may be a test kit for use in a laboratory or a home use test kit (over-the-counter test). The composition or kit may be a combination of any standard(s), control(s), reagent(s), solution(s) or solvent(s), either purchased from a commercial manufacturer or prepared in-house in a laboratory, used for diagnosing, predicting or detecting one or more cardiovascular events in a subject or for performing any of the methods or uses according to the present disclosure.

In certain embodiments, the composition or kit is a combination of any standard(s), control(s), reagent(s), solution(s) or solvent(s), either purchased from a commercial manufacturer or prepared in-house in a laboratory, used for assaying a concentration of at least one Cer of Formula I and a concentration of at least one PC of Formula II.

In certain embodiments of the composition or kit having the combination of any standard(s), control(s), reagent(s), solution(s) or solvent(s), either purchased from a commercial manufacturer or prepared in-house in a laboratory, the at least one Cer of Formula I is at least 2, at least 3, at least 4, at least 5, at least 6, at least 7, at least 8, at least 9 or at least 10 Cers of Formula I and the at least one PC of Formula II is at least 2, at least 3, at least 4, at least 5, at least 6, at least 7, at least 8, at least 9 or at least 10 PCs of Formula II.

In certain embodiments, the composition or kit is a combination of any standard(s), control(s), reagent(s), solution(s) or solvent(s), either purchased from a commercial manufacturer or prepared in-house in a laboratory, used for assaying a concentration of at least one Cer and/or at least one PC, selected from any of the Cer and PC species referred to in Table 1.

The composition or kit may be used in assays performed with various chemical and high-resolution analytical techniques, as appropriate. Suitable analytical techniques according to the present methods and uses include, but are not limited to, mass spectrometry (MS) and nuclear magnetic resonance (NMR). Any high-resolution technique capable of resolving individual biomarkers can be used to collect the information on the biomarker in question, such as the concentration of a biomarker profile from the biological sample. Typically, the information is collected using mass spectrometry. The MS analysis can be coupled to another high performance separation method, such as gas chromatography (GC), two-dimensional gas chromatography (GC×GC), liquid chromatography (LC), two-dimensional liquid chromatography (LC×LC), high performance liquid chromatography (HPLC) or ultra-high performance liquid chromatography (UHPLC).

In another aspect of the disclosure, a method is provided for monitoring the progress of CVD and/or CV event risk of a subject, wherein the method comprises assaying a sample from the subject to determine a concentration of at least one ceramide (Cer) of Formula I and a concentration of at least one phosphatidylcholine (PC) of Formula II and comparing the concentrations to those in a previously obtained sample from the same subject.

In certain embodiments of the method for monitoring the progress of CVD and/or CV event risk of a subject as described herein the at least one Cer of Formula I is at least 2, at least 3, at least 4, at least 5, at least 6, at least 7, at least 8, at least 9 or at least 10 Cers of Formula I and/or the at least one PC of Formula II is at least 2, at least 3, at least 4, at least 5, at least 6, at least 7, at least 8, at least 9 or at least 10 PCs of Formula II.

In certain embodiments, the method further comprises assaying the sample to determine a concentration of at least one additional Cer and/or at least one additional PC, selected from any of the Cer and PC species referred to in Table 1.

In certain embodiments of all aspects of the present disclosure, the methods and uses further comprise a step of adding at least one isotope-labelled Cer of Formula I and/or at least one isotope-labelled PC of Formula II to the sample prior to assaying the concentration of the at least one Cer of Formula I and/or the at least one PC of Formula II. The at least one isotope-labelled Cer of Formula I and/or the at least one isotope-labelled PC of Formula II may be, but is not limited to, deuterium-labelled Cer of Formula I and/or deuterium-labelled PC of Formula II. The at least one isotope-labelled Cer of Formula I and/or the at least one isotope-labelled PC of Formula II may also be $^{13}$C-labelled or $^{15}$N-labelled. In certain embodiments of all aspects of the present disclosure, the methods and uses further comprise a step of adding at least one, at least 2, at least 3, at least 4, at least 5, at least 6, at least 7, at least 8, at least 9 or at least 10 isotope-labelled Cers of Formula I and/or at least one, at least 2, at least 3, at least 4, at least 5, at least 6, at least 7, at least 8, at least 9 or at least 10 isotope-labelled PCs of Formula II to the sample. The at least one, at least 2, at least 3, at least 4, at least 5, at least 6, at least 7, at least 8, at least 9 or at least 10 isotope-labelled Cers of Formula I and/or the at least one, at least 2, at least 3, at least 4, at least 5, at least 6, at least 7, at least 8, at least 9 or at least 10 isotope-labelled PCs of Formula II may be, but are not limited to, deuterium-labelled, $^{13}$C-labelled or $^{15}$N-labelled Cers of Formula I and/or deuterium-labelled PCs of Formula II.

In certain embodiments of all aspects of the present disclosure, the methods and uses further comprise a step of adding at least one additional isotope-labelled Cer and/or at least one additional isotope-labelled PC, selected from any of the Cer and PC species referred to in Table 1, to the sample. The at least one additional isotope-labelled Cer and/or the at least one additional isotope-labelled PC, selected from any of the Cer and PC species referred to in Table 1, may be, but is not limited to, deuterium-labelled, $^{13}$C-labelled or $^{15}$N-labelled Cer and/or deuterium-labelled, $^{13}$C-labelled or $^{15}$N-labelled PC, selected from any of the Cer and PC species referred to in Table 1.

In certain embodiments of all aspects of the present disclosure, the isotope-labelled Cer and/or PC is selected from the following isotope-labelled lipids: Cer(d18:1/16:0), Cer(d18:1/18:0), Cer(d18:1/22:0), Cer(d18:1/24:0), Cer (d18:1/24:1), Cer(d18:1/26:0), Cer(d18:1/26:1), Cer(d16:1/16:0), Cer(d16:1/18:0), Cer(d16:1/24:0), Cer(d16:1/24:1), Cer(d18:2/16:0), Cer(d18:2/18:0), Cer(d18:2/24:1), Cer (d18:2/24:0), Cer(d20:1/24:1), PC 16:0/22:5, PC 14:0/22:6, PC 16:0/16:0, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8.

In certain embodiments of all aspects of the present disclosure, the isotope-labelled Cer and/or PC is selected from the following isotope-labelled lipids: Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled Cers and PCs are Cer(d18:1/16:0), Cer(d18:1/18:0), Cer(d18:1/24:0), Cer(d18:1/24:1), PC 16:0/22:5, PC 14:0/22:6 and PC 16:0/16:0.

In certain embodiments of all aspects of the present disclosure, the isotope-labelled Cer(d18:1/16:0), Cer(d18:1/18:0), Cer(d18:1/24:0), Cer(d18:1/24:1), PC 16:0/22:5, PC 14:0/22:6 and/or PC 16:0/16:0 is (are) deuterium-labelled.

In certain embodiments of all aspects of the present disclosure, the isotope-labelled lipid(s) is (are) d7-Cer(d18:1/16:0), d7-Cer(d18:1/18:0), d7-Cer(d18:1/24:0), d7-Cer(d18:1/24:1), d9-PC 16:0/22:5, d9-PC 14:0/22:6 and/or d9-PC 16:0/16:0.

In certain embodiments of all aspects of the present disclosure, the concentration of the at least one Cer of Formula I and the concentration of the at least one PC of Formula II are determined in one assay. In some embodiments, the concentrations of the at least one, at least 2, at least 3, at least 4, at least 5, at least 6, at least 7, at least 8, at least 9 or at least 10 Cers of Formula I and/or the at least one, at least 2, at least 3, at least 4, at least 5, at least 6, at least 7, at least 8, at least 9 or at least 10 PCs of Formula II are determined in the same assay. In some embodiments, a concentration of the at least one additional Cer and/or the at least one additional PC, selected from any of the Cer and PC species referred to in Table 1, are determined in the same assay. In some embodiments, the one assay is performed with mass spectrometry (MS).

In certain embodiments of all aspects of the present disclosure, the at least one additional Cer is at least 2, at least 3, at least 4, at least 5, at least 6, at least 7, at least 8, at least 9 or at least 10 additional Cers, selected from any of the Cer species referred to in Table 1. In some embodiments, the at least one additional Cer is a combination, including, but not limited to, a Cer/Cer ratio, of at least 2, at least 3, at least 4, at least 5, at least 6, at least 7, at least 8, at least 9 or at least 10 additional Cers. The combination may also be another combination as described herein.

In certain embodiments of all aspects of the present disclosure, the at least one additional PC is at least 2, at least 3, at least 4, at least 5, at least 6, at least 7, at least 8, at least 9 or at least 10 additional PCs, selected from any of the PC species referred to in Table 1. In some embodiments, the at least one additional PC is a combination, including, but not limited to, a PC/PC ratio, of at least 2, at least 3, at least 4, at least 5, at least 6, at least 7, at least 8, at least 9 or at least 10 additional PCs. The combination may also be another combination as described herein.

In certain embodiments of all aspects of the present disclosure, the method or use further comprises determining the level of total cholesterol (TC), low-density lipoprotein (LDL), low-density lipoprotein cholesterol (LDL-C), high-density lipoprotein (HDL), high-density lipoprotein cholesterol (HDL-C), low-density lipoprotein particle (LDL-P), high-density lipoprotein particle (HDL-P), Apolipoprotein B (ApoB), Apolipoprotein AI (ApoAI), Apolipoprotein AII (ApoAII), and/or Apolipoprotein C (ApoC) in a sample from the subject. In certain embodiments, the subject does not have elevated levels of one or more of total cholesterol, low-density lipoprotein cholesterol (LDL-C), Apolipoprotein C (ApoC) or Apolipoprotein B (ApoB), or a decreased level of HDL-cholesterol (HDL-C).

In certain embodiments of all aspects of the present disclosure, the method or use further comprises determining other cardiovascular biomarkers, including, but not limited to, triglyseride (TG), C-reactive protein (CRP), troponin T (TNT orTnT), troponin I (TNI or TnI), B-type natriuretic peptide (BNP), N-terminal pro B-type natriuretic peptide (NT-proBNP), Cystatin C, glycated haemoglobin A1c (HbA1c), glucose, suppression of tumorigenicity 2 (St2), Galectin, trimethylamine-N-oxide (TMAO), lipoprotein-associated phospholipase A2 (Lp-PLA2), growth differentiation factor 15 (GDF15), lipoprotein (a) (Lp(a)), any other lipoprotein subgroup composition or particle number, or any combination thereof.

In certain embodiments of all aspects of the present disclosure, the method or use may further comprise determining any other cardiovascular or metabolic biomarker, including, but not limited to creatine kinase (CK).

In certain embodiments of all aspects of the present disclosure, the method or use further comprises using other personal information or health data, such as sex, age, blood pressure, BMI, smoking status, diabetes, lipid lowering treatment or other medication, history of cardiovascular events, ethnic background, geographical location, medical imaging data, e.g. from angiography or computed tomography (CT), or any combination thereof.

In certain embodiments of all aspects of the present disclosure, the method or use may further comprise using any personal information or health data, including, but not limited to history of CVD and/or CV events, family history of CVD and/or CV events, family history of diabetes, family history of other diseases.

In certain embodiments of all aspects of the present disclosure, the cardiovascular (CV) event comprises stable angina pectoris, unstable angina pectoris, myocardial infarction (MI), acute myocardial infarction (AMI), acute coronary syndrome (ACS), stroke, transient ischemic attacks, deep vein thrombosis, heart failure, hospitalization for heart failure and cardiovascular death.

In certain embodiments of all aspects of the present disclosure, the cardiovascular (CV) event comprises peripheral artery disease (also called peripheral arterial disease) and/or arrhythmia, such as atrial fibrillation.

In certain embodiments of all aspects of the present disclosure, the subject is any mammalian subject for whom prediction, diagnosis or therapy is desired. In certain embodiments, the subject is human. In some embodiments, the subject is a healthy individual with no previous signs or symptoms of CVD. In other embodiments, the subject has previously suffered or is suffering from CVD or CAD. The subject may also have previously suffered from a cardiovascular event, such as angina pectoris, myocardial infarction or stroke. In some embodiments, the subject is suffering from a metabolic disease, such as diabetes. In some embodiments, the subject is suspected of suffering CVD and/or being at high risk of developing CV events.

In some embodiments, the subject has normal levels of traditional risk markers, such as total cholesterol, LDL or HDL and/or has no traditional risk factors, such as diabetes, high blood pressure or smoking. In certain embodiments, the subject is under a treatment, such as, a statin treatment.

In certain embodiments of all aspects of the present disclosure, the sample is a biological sample obtained from a subject or a group or population of subjects. In certain embodiments, the sample is a blood sample, a serum sample, a plasma sample, a saliva sample, a urine sample, a tissue sample or a fraction thereof, such as a lipoprotein fraction. In certain embodiments, the sample is a serum or plasma sample. The sample can be prepared with techniques well known in the art. In certain embodiments, the blood sample is a dried blood spot. In certain embodiments, the blood sample is dried on a filter.

In certain embodiments of all aspects of the present disclosure, the control is a control sample or a control value obtained from a single healthy individual or a generalized population of healthy individuals. In some embodiments, the control is a control value or a set of data concerning the biomarker in a sample previously determined. In some embodiments, the control sample is previously obtained from the same subject or the control value is obtained from a previously taken sample from the same subject, to be used for example for controlling the progress of CVD.

In certain embodiments, the control is obtained from a CVD patient that has remained free of any major CV events, or a group of CVD patients that have remained free of any major CV events.

In certain embodiments, a control is a control value, e.g., a score or a combination value of the concentrations of the at least one Cer of Formula I and the at least one PC of Formula II or a combination value of the at least one Cer of Formula I and the at least one PC of Formula II and the at least one additional Cer or PC, selected from any of the Cer and PC species referred to in Table 1.

In certain embodiments of all aspects of the present disclosure, the treatment comprises any therapeutic treatment typically given to a subject at risk of developing CVD or a subject suffering from CVD, such as, but not limited to, administering a drug and/or providing therapeutic, behavioural and/or lifestyle modification to the subject. In some embodiments, the behavioural and/or lifestyle modification comprises, for example, lifestyle interventions and/or counselling, including instructions, encouragement and/or follow-up regarding a healthy diet, weight management, physical activity/exercise and/or smoking cessation. In certain embodiments, the treatment comprises a surgical operation, such as angioplasty, stent placement or bypass surgery. In certain embodiments, the treatment comprises controlling of progression of CVD and/or its complications.

In certain embodiments of all aspects of the present disclosure, the drug comprises any pharmaceutical typically given to a subject having CVD, such as a statin, another lipid lowering/modifying drug, and/or a modulator of lipid concentrations. In some embodiments, the drug is an HMG-CoA reductase inhibitor (a statin or other HMG-CoA reductase inhibitor), niacin (nicotinic acid), a cholesterol absorption inhibitor (ezetimibe), a cholesteryl ester transfer protein (CETP) inhibitor, a bile acid sequestrant, a fibrate, a phytosterol, an anti-inflammatory drug (e.g. methotrexate, IL-1 mAb, TNF-alpha mAb), acetylsalicylic acid (aspirin) or a PCSK9 inhibitor, or a modulator of lipid concentrations selected from a small molecule, an antibody, an antisense RNA, a small interfering RNA (siRNA), and a natural or modified lipid, or any combination thereof.

In certain embodiments, the statin comprises atorvastatin, cerivastatin, fluvastatin, fluvastatin XL, lovastatin, pitavastatin, pravastatin, rosuvastatin, simvastatin, or any combination thereof.

In some embodiments, the cholesterol absorption inhibitor is ezetimibe or SCH-48461, the cholesteryl ester transfer protein (CETP) inhibitor is evacetrapib, anacetrapib or dalcetrapib, the bile acid sequestrant is colesevelam, cholestyramine or colestipol, the fibrate is fenofibrate, gemfibrozil, clofibrate, or bezafibrate, and the PCSK9 inhibitor is a PCSK9 specific antibody, an siRNA, and a peptidomimetic.

In certain embodiments of all aspects of the present disclosure, the determination of Cer and PC concentrations is typically performed using an assay. In certain embodiments, such assay is, or involves, mass spectrometry, nuclear magnetic resonance spectroscopy, fluorescence spectroscopy or dual polarisation interferometry, a high performance separation method such as liquid chromatography (LC), gas chromatography (GC), two-dimensional liquid chromatography (LC×LC), two-dimensional gas chromatography (GC×GC), high performance liquid chromatography (HPLC), ultra high performance liquid chromatography (UHPLC) or ultra performance liquid chromatography (UPLC), an immunoassay such as an ELISA and/or an assay with a binding moiety capable of specifically binding the analyte. In certain embodiments, the assay is mass spectrometry (MS). The MS instrument can be coupled to a direct sample infusion method, such as a robotic nanoflow ion source device, or to a high performance separation method such as HPLC, UHPLC, or UPLC.

In certain embodiments of all aspects of the present disclosure, the concentrations of at least one, at least 2, at least 3, at least 4, at least 5, at least 6, at least 7, at least 8, at least 9 or at least 10 Cers of Formula I are assayed. In another embodiment, the concentrations of at least one, at least 2, at least 3, at least 4, at least 5, at least 6, at least 7, at least 8, at least 9 or at least 10 PCs of Formula II are assayed. In yet another embodiment, the concentrations of at least one, at least 2, at least 3, at least 4, at least 5, at least 6, at least 7, or at least 8, at least 9 or at least 10 Cers of Formula I and/or at least one, at least 2, at least 3, at least 4, at least 5, at least 6, at least 7, at least 8, at least 9 or at least 10 PCs of Formula II are assayed.

In certain embodiments of all aspects of the disclosure, the concentration of at least one, at least 2, at least 3, at least 4, at least 5, at least 6, at least 7, at least 8, at least 9 or at least 10 additional Cers, selected from any of the Cer species referred to in Table 1, are assayed. In another embodiment, the concentrations of at least one, at least 2, at least 3, at least 4, at least 5, at least 6, at least 7, at least 8, at least 9 or at least 10 additional PCs, selected from any of the PC species referred to in Table 1, are assayed.

In yet another embodiment, the concentrations of at least one, at least 2, at least 3, at least 4, at least 5, at least 6, at least 7, or at least 8, at least 9 or at least 10 additional Cers of Formula I, selected from any of the Cer species referred to in Table 1, and/or at least one, at least 2, at least 3, at least 4, at least 5, at least 6, at least 7, at least 8, at least 9 or at least 10 additional PCs of Formula II, selected from any of the PC species referred to in Table 1, are assayed.

In certain embodiments of all aspects of the disclosure, $R^1$ of Formula I is a saturated, mono-unsaturated or di-unsaturated alkyl chain having 11-17 carbon atoms, and $R^2$ is a saturated alkyl chain having 13-21 carbon atoms, a mono-unsaturated or di-unsaturated alkyl chain having 13-25 carbon atoms.

In certain embodiments of all aspects of the disclosure, $R^1$ of Formula I is a mono-unsaturated or di-unsaturated alkyl chain having 13-15 carbon atoms, and $R^2$ is a saturated, mono-unsaturated or di-unsaturated alkyl chain having 15-25 carbon atoms.

In certain embodiments of all aspects of the disclosure, $R^1$ of Formula I is a mono-unsaturated or di-unsaturated alkyl chain having 13-15 carbon atoms, and $R^2$ is a saturated alkyl chain having 15-21 carbon atoms, a mono-unsaturated or di-unsaturated alkyl chain having 15-25 carbon atoms.

In all aspects of the present disclosure, the PC may be a brutto PC or a molecular PC.

In certain embodiments of all aspects of the disclosure, $R^3$ and $R^4$ of Formula II are saturated, mono-unsaturated or polyunsaturated alkyl chains having 11-26 carbon atoms. In certain embodiments of all aspects of the disclosure, $R^3$ and $R^4$ of Formula II are saturated, mono-unsaturated or polyunsaturated alkyl chains having up to 6 double bonds.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0), Cer(d18:1/22:0), Cer(d18:1/24:1), Cer(d18:1/26:1), Cer(d16:1/16:0), Cer (d16:1/18:0), Cer(d16:1/24:1), Cer(d18:2/16:0), Cer(d18:2/18:0), Cer(d18:2/24:1) and/or Cer(d20:1/24:1). In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/22:5, PC 14:0/22:6, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8. In other embodiments, at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0), Cer(d18:1/22:0), Cer(d18:1/24:1), Cer(d18:1/26:1), Cer (d16:1/16:0), Cer(d16:1/18:0), Cer(d16:1/24:1), Cer(d18:2/16:0), Cer(d18:2/18:0), Cer(d18:2/24:1) and/or Cer(d20:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/22:5, PC 14:0/22:6, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer (d18:1/24:1). In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/22:5, PC 14:0/22:6, PC 16:0/22:6, PC 16:0/20:4, PC 18:0/20:4, PC 17:0/20:3, PC 36:8, PC 36:6, PC 36:4, PC 38:4, PC 38:7, PC 34:4 and/or PC 40:8. In other embodiments, at least one, at least 2, at least 3, at least 4, at least 5, at least 6, at least 7, at least 8, at least 9 or at least 10 Cers of Formula I are assayed, including but not limited to: Cer(d18:1/16:0), Cer (d18:1/18:0) and/or Cer(d18:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/22:5, PC 14:0/22:6, PC 16:0/22:6, PC 16:0/20:4, PC 18:0/20:4, PC 17:0/20:3, PC 36:8, PC 36:6, PC 36:4, PC 38:4, PC 38:7, PC 34:4 and/or PC 40:8.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer (d18:1/24:1). In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 14:0/22:6. In other embodiments, at least one, at least 2, at least 3, at least 4, at least 5, at least 6, at least 7, at least 8, at least 9 or at least 10 Cers of Formula I are assayed, including but not limited to: Cer(d18:1/16:0), Cer (d18:1/18:0) and/or Cer(d18:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 14:0/22:6. In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer(d18:1/24:1), and a concentration of at least one additional Cer and/or at least one additional PC, selected from any of the Cer and PC species referred to in Table 1, are assayed.

In certain embodiments of all aspects of the disclosure, the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 14:0/22:6, and a concentration of at least one additional Cer and/or at least one additional PC, selected from any of the Cer and PC species referred to in Table 1, are assayed.

In certain embodiments of all aspects of the disclosure, at least one, at least 2, at least 3, at least 4, at least 5, at least 6, at least 7, at least 8, at least 9 or at least 10 Cers of Formula I are assayed, including but not limited to: Cer (d18:1/16:0), Cer(d18:1/18:0) and/or Cer(d18:1/24:1), the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 14:0/22:6, and a concentration of at least one additional Cer and/or at least one additional PC, selected from any of the Cer and PC species referred to in Table 1, are assayed.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer (d18:1/24:1), and the concentration of at least one additional Cer is assayed, including but not limited to: Cer(d18:1/24:1), Cer(d18:1/24:0), Cer(d18:1/16:0), Cer(d18:1/18:0), Cer (d18:1/26:0), Cer(d18:1/26:1), Cer(d16:1/16:0), Cer(d16:1/ 18:0), Cer(d16:1/24:0), Cer(d16:1/24:1), Cer(d18:2/16:0), Cer(d18:2/18:0), Cer(18:2/24:0), Cer(d18:2/24:1), Cer(d20: 1/24:0) and/or Cer(d20:1/24:1. In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 14:0/22:6, and the concentration of at least one additional PC is assayed, including but not limited to: PC 16:0/16:0, 16:0/22:5, PC 14:0/22:6, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8. In other embodiments, at least one, at least 2, at least 3, at least 4, at least 5, at least 6, at least 7, at least 8, at least 9 or at least 10 Cers of Formula I are assayed, including but not limited to: Cer (d18:1/16:0), Cer(d18:1/18:0) and/or Cer(d18:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 14:0/22:6, and the concentration of at least one additional Cer is assayed, including but not limited to: Cer(d18:1/24:1), Cer(d18:1/24: 0), Cer(d18:1/16:0), Cer(d18:1/18:0), Cer(d18:1/26:0), Cer (d18:1/26:1), Cer(d16:1/16:0), Cer(d16:1/18:0), Cer(d16:1/ 24:0), Cer(d16:1/24:1), Cer(d18:2/16:0), Cer(d18:2/18:0), Cer(18:2/24:0), Cer(d18:2/24:1), Cer(d20:1/24:0) and/or Cer(d20:1/24:1), and the concentration of at least one additional PC is assayed, including but not limited to: PC 16:0/16:0, 16:0/22:5, PC 14:0/22:6, PC 18:0/20:5, PC 16:0/ 20:4, PC 18:0/20:4, PC 18:0/20:3, PC 16:0/22:6, PC 16:1/ 18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8.

In certain embodiments of all aspects of the disclosure, the concentrations of Cer(d18:1/16:0), Cer(d18:1/18:0), Cer (d18:1/24:1) and/or Cer(d18:1/24:0) are assayed. In some embodiments, the concentrations of PC 16:0/22:5 and/or PC 14:0/22:6 are assayed.

In certain embodiments of all aspects of the disclosure, the concentrations of at least 2, at least 3, at least 4, at least 5 or at least 6 of the following lipids are assayed: Cer(d18: 1/16:0), Cer(d18:1/18:0), Cer(d18:1/24:1), Cer(d18:1/24:0), PC 16:0/22:5 and PC 14:0/22:6.

In other embodiments, Cer(d18:1/16:0), Cer(d18:1/18:0), Cer(d18:1/24:1), Cer(d18:1/24:0), PC 16:0/22:5 and PC 14:0/22:6 are assayed.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer (d18:1/24:1), and the concentration of at least one additional Cer is assayed, including but not limited to: Cer(d18:1/24:0). In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 16:0/22:6. In other embodiments, at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18: 0) and/or Cer(d18:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 16:0/22:6, and the concentration of at least one additional Cer is assayed, including but not limited to: Cer(d18:1/24:0).

In certain embodiments of all aspects of the disclosure, the concentrations of Cer(d18:1/16:0), Cer(d18:1/18:0), Cer (d18:1/24:1) and/or Cer(d18:1/24:0) are assayed. In some embodiments, the concentrations of PC 16:0/22:5, PC 14:0/22:6 and/or PC 16:0/16:0 are assayed.

In certain embodiments of all aspects of the disclosure, the concentrations of at least 2, at least 3, at least 4, at least 5, at least 6 or at least 7 of the following lipids are assayed: Cer(d18:1/16:0), Cer(d18:1/18:0), Cer(d18:1/24:1), Cer(d18:1/24:0), PC 16:0/22:5, PC 14:0/22:6 and PC 16:0/16:0.

In other embodiments, Cer(d18:1/16:0), Cer(d18:1/18:0), Cer(d18:1/24:1), Cer(d18:1/24:0), PC 16:0/22:5, PC 14:0/22:6 and PC 16:0/16:0 are assayed.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer(d18:1/24:1), and the concentration of at least one additional Cer is assayed, including but not limited to: Cer(d18:1/24:0). In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 16:0/22:6, and the concentration of at least one additional PC is assayed, including but not limited to: PC 16:0/16:0. In other embodiments, at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer(d18:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 16:0/22:6, and the concentration of at least one additional Cer is assayed, including but not limited to: Cer(d18:1/24:0), and the concentration of at least one additional PC is assayed, including but not limited to: PC 16:0/16:0.

In certain embodiments of all aspects of the disclosure, the concentrations of Cer(d18:1/16:0), Cer(d18:1/18:0), Cer(d18:1/24:1) and/or Cer(d18:1/24:0) are assayed. In some embodiments, the concentrations of PC 16:0/22:5, PC 16:0/22:6 and/or PC 16:0/16:0 are assayed.

In certain embodiments of all aspects of the disclosure, the concentrations of at least 2, at least 3, at least 4, at least 5, at least 6 or at least 7 of the following lipids are assayed: Cer(d18:1/16:0), Cer(d18:1/18:0), Cer(d18:1/24:1), Cer(d18:1/24:0), PC 16:0/22:5, PC 16:0/22:6 and PC 16:0/16:0.

In other embodiments, Cer(d18:1/16:0), Cer(d18:1/18:0), Cer(d18:1/24:1), Cer(d18:1/24:0), PC 16:0/22:5, PC 16:0/22:6 and PC 16:0/16:0 are assayed.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer(d18:1/24:1), and the concentration of at least one additional Cer is assayed, including but not limited to: Cer(d18:1/24:0). In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 40:8, and the concentration of at least one additional PC is assayed, including but not limited to: PC 16:0/18:3. In other embodiments, at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer(d18:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/22:5 and/or PC 40:8, and the concentration of at least one additional Cer is assayed, including but not limited to: Cer(d18:1/24:0), and the concentration of at least one additional PC is assayed, including but not limited to: PC 16:0/18:3.

In certain embodiments of all aspects of the disclosure, the concentrations of at least Cer(d18:1/16:0), Cer(d18:1/18:0), Cer(d18:1/24:1) and Cer(d18:1/24:0) are assayed. In some embodiments, the concentrations of at least PC 16:0/22:5, PC 40:8 and PC 16:0/18:3 are assayed.

In certain embodiments of all aspects of the disclosure, the concentrations of at least 2, at least 3, at least 4, at least 5, at least 6 or at least 7 of the following lipids are assayed: Cer(d18:1/16:0), Cer(d18:1/18:0), Cer(d18:1/24:1), Cer(d18:1/24:0), PC 16:0/22:5, PC 16:0/22:6 and PC 16:0/18:3.

In other embodiments, Cer(d18:1/16:0), Cer(d18:1/18:0), Cer(d18:1/24:1), Cer(d18:1/24:0), PC 16:0/22:5, PC 16:0/22:6 and PC 16:0/18:3 are assayed.

In certain embodiments of all aspects of the disclosure, the concentrations of at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer(d18:1/24:1). In some embodiments, the concentrations of at least one, at least 2, at least 3, at least 4, at least 5, at least 6, at least 7, at least 8, at least 9 or at least 10 PCs of Formula II are assayed, including but not limited to: PC 16:0/20:4, PC 18:0/20:4 and/or PC 38:7. In other embodiments, at least one, at least 2, at least 3, at least 4, at least 5, at least 6, at least 7, at least 8, at least 9 or at least 10 Cers of Formula I are assayed, including but not limited to: Cer(d18:1/16:0), Cer(d18:1/18:0) and/or Cer(d18:1/24:1), and the concentrations of at least one, at least 2, at least 3, at least 4, at least 5, at least 6, at least 7, at least 8, at least 9 or at least 10 PCs of Formula II are assayed, including but not limited to: PC 16:0/20:4, PC 18:0/20:4 and/or PC 38:7.

In certain embodiments of all aspects of the disclosure, the concentrations of at least Cer(d18:1/16:0), Cer(d18:1/18:0), Cer(d18:1/24:1) are assayed. In some embodiments, the concentrations of at least PC 16:0/20:4, PC 18:0/20:4 and/or PC 38:7 are assayed.

In certain embodiments of all aspects of the disclosure, the concentrations of at least 2, at least 3, at least 4, at least 5 or at least 6 of the following lipids are assayed: Cer(d18:1/16:0), Cer(d18:1/18:0), Cer(d18:1/24:1), PC 16:0/20:4, PC 18:0/20:4 and PC 38:7.

In other embodiments, Cer(d18:1/16:0), Cer(d18:1/18:0), Cer(d18:1/24:1), PC 16:0/20:4, PC 18:0/20:4 and PC 38:7 are assayed.

In certain embodiments of all aspects of the disclosure, a concentration ratio is calculated from the concentrations of the at least one, at least 2, at least 3, at least 4, at least 5, at least 6, at least 7, at least 8, at least 9 or at least 10 Cers of Formula I and/or the concentrations of the at least one, at least 2, at least 3, at least 4, at least 5, at least 6, at least 7, at least 8, at least 9 or at least 10 PCs of Formula II.

In certain embodiments of all aspects of the disclosure, a concentration ratio is calculated from the concentrations of the at least one Cer of Formula I and/or the concentrations of the at least one PC of Formula II. In some embodiments, the concentration ratio is calculated from the concentration of a Cer of Formula I and the concentrations of a PC of Formula II. In certain embodiments, the concentration ratio is a Cer/Cer, Cer/PC, PC/Cer and/or PC/PC ratio, e.g., Cer(d18:1/16:0)/PC 16:0/22:5, Cer(d18:1/18:0)/PC 14:0/22: 6, PC 16:0/22:5/Cer(d18:1/16:0) and/or PC 14:0/22:6/Cer (d18:1/18:0).

In certain embodiments of all aspects of the disclosure, a concentration ratio is calculated from the concentrations of the at least one additional Cer and/or the at least one additional PC selected from any of the Cer and PC species referred to in Table 1. In certain embodiments, the concentration ratio is a Cer/Cer, Cer/PC, PC/Cer and/or PC/PC ratio, e.g., Cer(d18:1/24:1)/Cer(d18:1/24:0) and/or Cer(d18:1/24:0)/Cer(d18:1/24:1).

In certain embodiments of all aspects of the disclosure, (an) increased concentration ratio(s) of the at least one Cer of Formula I and the at least one PC of Formula II in the sample from the subject, when compared to a control, is (are) indicative of the subject having a risk of developing one or more cardiovascular events.

In certain embodiments of all aspects of the disclosure, (an) increased or decreased concentration ratio(s) of the at least one additional Cer of Formula I and/or the at least one additional PC of Formula II, selected from any of the Cer and PC species referred to in Table 1, in the sample from the subject, when compared to a control, is (are) indicative of the subject having a risk of developing one or more cardiovascular events.

In certain embodiments of all aspects of the disclosure, the concentration ratio is a Cer/Cer, Cer/PC, PC/Cer and/or PC/PC ratio, and (an) increased or decreased concentration ratio(s) in the sample from the subject, when compared to a control, is (are) indicative of the subject having a risk of developing one or more cardiovascular events.

In a typical embodiment of all aspects of the present disclosure, the following concentration ratios are determined from the Formula I Cers and the Formula II PCs: Cer(d18:1/16:0)/PC 16:0/22:5 and/or Cer(d18:1/18:0)/PC 14:0/22:6. In this typical embodiment, the following concentration ratio from the Table 1 additional Cer species is also determined: Cer(d18:1/24:1)/Cer(d18:1/24:0). In this typical embodiment of all aspects of the present disclosure, the following concentration from an additional PC species from Table 1 is also determined: PC 16:0/16:0.

In another typical embodiment of all aspects of the present disclosure, the following concentration ratios are determined from the Formula I Cers and the Formula II PCs: Cer(d18:1/16:0)/PC 16:0/22:5 and/or Cer(d18:1/18:0)/PC 14:0/22:6. In this typical embodiment, the following concentration ratio from the Table 1 additional Cer species is also determined: Cer(d18:1/24:1)/Cer(d18:1/24:0).

In certain embodiments of all aspects of the disclosure, a concentration ratio is calculated from the concentrations of the at least one, at least 2, at least 3, at least 4, at least 5, at least 6, at least 7, at least 8, at least 9 or at least 10 additional Cer and/or the at least one, at least 2, at least 3, at least 4, at least 5, at least 6, at least 7, at least 8, at least 9 or at least 10 additional PC selected from any of the Cer and PC species referred to in Table 1. In some embodiments, the concentration ratio comprises at least one, at least 2, at least 3, at least 4, at least 5, at least 6, at least 7, at least 8, at least 9 or at least 10 additional Cers selected from any of the Cer species referred to in Table 1. In some embodiments, the concentration ratio comprises at least one, at least 2, at least 3, at least 4, at least 5, at least 6, at least 7, at least 8, at least 9 or at least 10 additional PCs selected from any of the PC species referred to in Table 1. In some embodiments, the concentration ratio comprises at least one, at least 2, at least 3, at least 4, at least 5, at least 6, at least 7, at least 8, at least 9 or at least 10 additional Cers selected from any of the Cer species referred to in Table 1 and at least one, at least 2, at least 3, at least 4, at least 5, at least 6, at least 7, at least 8, at least 9 or at least 10 additional PCs selected from any of the PC species referred to in Table 1.

In certain embodiments of all aspects of the disclosure, a concentration ratio is calculated from the concentrations of the at least one, at least 2, at least 3, at least 4, at least 5, at least 6, at least 7, at least 8, at least 9 or at least 10 Cers of Formula I, the concentrations of the at least one, at least 2, at least 3, at least 4, at least 5, at least 6, at least 7, at least 8, at least 9 or at least 10 PCs of Formula II, the at least one, at least 2, at least 3, at least 4, at least 5, at least 6, at least 7, at least 8, at least 9 or at least 10 additional Cers, selected from any of the Cer species referred to in Table 1, and/or at least one, at least 2, at least 3, at least 4, at least 5, at least 6, at least 7, at least 8, at least 9 or at least 10 additional PCs, selected from any of the PC species referred to in Table 1.

In certain embodiments of all aspects of the disclosure, a concentration ratio is selected from any of the lipid ratios referred to in Table 2, 3, 4, 6, 7, 8, 9, 10, 11 or 12.

In certain embodiments of all aspects of the disclosure, a concentration ratio is calculated from at least 2 of the following lipids: Cer(d18:1/16:0), Cer(d18:1/18:0), Cer(d18:1/22:0), Cer(d18:1/24:0), Cer(d18:1/24:1), Cer(d18:1/26:0), Cer(d18:1/26:1), Cer(d16:1/16:0), Cer(d16:1/18:0), Cer(d16:1/24:0), Cer(d16:1/24:1), Cer(d18:2/16:0), Cer(d18:2/18:0), Cer(d18:2/24:1), Cer(d18:2/24:0), Cer(d20:1/24:1), PC 16:0/22:5, PC 14:0/22:6, PC 16:0/16:0, PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and/or PC 40:8.

In certain embodiments of all aspects of the disclosure, a concentration ratio is calculated from 2 of the following lipids: Cer(d18:1/16:0), Cer(d18:1/18:0), Cer(d18:1/24:0), Cer(d18:1/24:1), PC 16:0/22:5, PC 14:0/22:6 and/or PC 16:0/16:0.

In certain embodiments of all aspects of the disclosure, a concentration ratio is calculated from 2 of the following lipids: Cer(d18:1/16:0), Cer(d18:1/18:0), Cer(d18:1/24:1), PC 16:0/22:5 and/or PC 14:0/22:6.

In certain embodiments of all aspects of the disclosure, the concentration ratio may be, but is not limited to, Cer(d18:1/16:0)/PC 16:0/22:5, Cer(d18:1/18:0)/PC 14:0/22:6 and/or Cer(d18:1/24:1)/Cer(d18:1/24:0).

In certain embodiments of all aspects of the disclosure, the concentration ratios Cer(d18:1/16:0)/PC 16:0/22:5, Cer(d18:1/18:0)/PC 14:0/22:6 and Cer(d18:1/24:1)/Cer(d18:1/24:0) are assayed.

In certain embodiments of all aspects of the disclosure, the concentration ratios Cer(d18:1/16:0)/PC 16:0/22:5, Cer(d18:1/18:0)/PC 14:0/22:6 and Cer(d18:1/24:1)/Cer(d18:1/24:0) are assayed and the concentration of PC 16:0/16:0 is assayed.

In certain embodiments of all aspects of the disclosure, the lipid combination is selected from any of the lipid combinations referred to in Tables 2-18.

In certain embodiments of all aspects of the disclosure, the concentrations of at least 2, at least 3, at least 4, at least 5 or at least 6 of the following lipids are assayed: Cer(d18:1/16:0), Cer(d18:1/18:0), Cer(d18:1/24:1), Cer(d18:1/24:0), PC 36:6 and PC 38:5.

In certain embodiments of all aspects of the disclosure, the concentrations of Cer(d18:1/16:0), Cer(d18:1/18:0), Cer(d18:1/24:1), Cer(d18:1/24:0), PC 36:6 and 38:5 are assayed.

In certain embodiments of all aspects of the disclosure, the concentration ratios Cer(d18:1/24:1)/Cer(d18:1/24:0), Cer(d18:1/16:0)/PC 38:5 and Cer(d18:1/18:0)/PC 36:6 are assayed and the concentration of PC 32:0 is assayed.

In certain embodiments of all aspects of the disclosure, the marker combination may be constructed by linear combinations, regression models, other unsupervised or supervised frequentist or Bayesian statistical classification or machine learning methods, such as support vector machines, kernel estimations, decision trees or, neural networks.

In certain embodiments of all aspects of the disclosure, the marker combination is a continuous or discrete scoring systems based on the Cer, PC, Cer/PC, Cer/Cer, PC/Cer, PC/PC or other cardiovascular biomarkers. For discrete scoring, the points may be given based on intervals with non-equal probabilities, quantiles or other cut-off values, determined from the same or other populations, of the individual score components.

In certain embodiments of all aspects of the disclosure, the marker combination is a scoring system (for example, but not limited to, points 0-12, 0-15 or 0-9), where the points are given based on the quartiles (Q1-Q4) of the whole study population. For example, if a lipid biomarker of a person belongs to the highest quartile, the person will receive 3 points. The same evaluation will be performed for the other lipid biomarkers, and summed up.

In certain embodiments of all aspects of the disclosure, the score is based on at least 2, at least 3, at least 4, at least 5, at least 6, at least 7, at least 8, at least 9 or at least 10 lipids selected from: Cer(d18:1/16:0), Cer(d18:1/18:0), PC 16:0/22:5, PC 14:0/22:6, Cer(d18:1/24:1), Cer(d18:1/24:0), PC 16:0/16:0, Cer(d18:1/22:0), Cer(d18:1/26:0), Cer(d18:1/26:1), Cer(d16:1/16:0), Cer(d16:1/18:0), Cer(d16:1/24:0), Cer (d16:1/24:1), Cer(d18:2/16:0), Cer(d18:2/18:0), Cer(d18:2/24:1), Cer(d18:2/24:0), Cer(d20:1/24:1), PC 18:0/20:5, PC 16:0/20:4, PC 18:0/20:4, PC 18:0/20:3, PC 16:0/22:6, PC 16:1/18:2, PC 16:0/18:3, PC 17:0/20:3, PC 17:0/20:4, PC 38:5, PC 36:6, PC 38:5, PC 36:4, PC 38:4, PC 38:3, PC 38:6, PC 38:7, PC 34:3, PC 37:3, PC 37:4, PC 34:4 and PC 40:8.

In certain embodiments of all aspects of the disclosure, the score is based on at least 2, at least 3, at least 4, at least 5 or at least 6 of the following lipids: Cer(d18:1/16:0), Cer(d18:1/18:0), Cer(d18:1/24:0), Cer(d18:1/24:1), PC 16:0/22:5 and/or PC 14:0/22:6.

In certain embodiments of all aspects of the disclosure, the score is based on the following lipids: Cer(d18:1/16:0), Cer(d18:1/18:0), Cer(d18:1/24:0), Cer(d18:1/24:1), PC 16:0/22:5 and/or PC 14:0/22:6.

In certain embodiments of all aspects of the disclosure, the score is based on the following lipid ratios: Cer(d18:1/16:0)/PC 16:0/22:5, Cer(d18:1/18:0)/PC 14:0/22:6 and/or Cer(d18:1/24:1)/Cer(d18:1/24:0).

In certain embodiments of all aspects of the disclosure, the score is based on at least 2, at least 3, at least 4, at least 5, at least 6 or at least 7 of the following lipids: Cer(d18:1/16:0), Cer(d18:1/18:0), Cer(d18:1/24:0), Cer(d18:1/24:1), PC 16:0/22:5, PC 14:0/22:6 and/or PC 16:0/16:0.

In certain embodiments of all aspects of the disclosure, the score is based on the following lipids: Cer(d18:1/16:0), Cer(d18:1/18:0), Cer(d18:1/24:0), Cer(d18:1/24:1), PC 16:0/22:5, PC 14:0/22:6 and/or PC 16:0/16:0.

In certain embodiments of all aspects of the disclosure, the score is based on the following lipid ratios and individual lipid: Cer(d18:1/16:0)/PC 16:0/22:5, Cer(d18:1/18:0)/PC 14:0/22:6, Cer(d18:1/24:1)/Cer(d18:1/24:0) and/or PC 16:0/16:0.

In certain embodiments of all aspects of the disclosure, the score is based on the following lipids: Cer(d18:1/16:0), Cer(d18:1/18:0), Cer(d18:1/24:0), Cer(d18:1/24:1), PC 38:5 and/or PC 36:6.

In certain embodiments of all aspects of the disclosure, the score is based on the following lipids: Cer(d18:1/16:0), Cer(d18:1/18:0), Cer(d18:1/24:0), Cer(d18:1/24:1), PC 38:5, PC 36:6 and/or PC 32:0.

In certain embodiments of all aspects of the disclosure, the score is based on the following lipid ratios: Cer(d18:1/16:0)/PC 38:5, Cer(d18:1/18:0)/PC 36:6 and/or Cer(d18:1/24:1)/Cer(d18:1/24:0).

In certain embodiments of all aspects of the disclosure, the score is constructed according to Table 8, 9, 10 or 11.

In certain embodiments of all aspects of the disclosure, the score further comprises determining other cardiovascular biomarkers, including, but not limited to, triglyseride (TG), C-reactive protein (CRP), troponin T (TNT or TnT), troponin I (TNI or TnI), B-type natriuretic peptide (BNP), N-terminal pro B-type natriuretic peptide (NT-proBNP), Cystatin C, glycated haemoglobin A1c (HbA1c), glucose, suppression of tumorigenicity 2 (St2), Galectin, trimethylamine-N-oxide (TMAO), lipoprotein-associated phospholipase A2 (Lp-PLA2), growth differentiation factor 15 (GDF15), lipoprotein (a) (Lp(a)), any other lipoprotein subgroup composition or particle number, or any combination thereof.

In certain embodiments of all aspects of the present disclosure, the score may further comprise determining any other cardiovascular or metabolic biomarker, including, but not limited to creatine kinase (CK).

In certain embodiments of all aspects of the disclosure, the score further comprises TNT.

In certain embodiments of all aspects of the present disclosure, the score further comprises using other personal information or health data, such as sex, age, blood pressure, BMI, smoking status, diabetes, lipid lowering treatment or other medication, history of cardiovascular events, ethnic background, geographical location, medical imaging data, e.g. from angiography or computed tomography (CT), or any combination thereof.

In certain embodiments of all aspects of the present disclosure, the score may further comprise any personal information or health data, including, but not limited to history of CVD and/or CV events, family history of CVD and/or CV events, family history of diabetes, family history of other diseases.

In certain embodiments of all aspects of the disclosure, the score further comprises medical imaging data.

DETAILED DESCRIPTION OF THE INVENTION

The present disclosure is based on the finding that certain molecules are expressed at higher levels and certain molecules are expressed at lower levels, when compared to a control, in biological samples, e.g., blood of subjects having a risk to develop one or more cardiovascular (CV) events in the future. A combination derived from the concentrations of these molecules were found to be a surprisingly superior predictive biomarker of cardiovascular events, as described herein.

According to the present disclosure, a combination of the concentrations of at least one ceramide (Cer) and at least one phosphatidylcholine (PC) provide a specific and sensitive diagnostic test which can be used to identify subjects who are in a risk of developing cardiovascular events. The biomarker combination of the present disclosure can be used for predicting CV events when the levels of conventional markers, such as LDL-C(low density lipoprotein cholesterol), HDL-C(high density lipoprotein cholesterol) and total cholesterol, are either normal, increased or decreased. The present biomarker combination can also be used for subjects who have or have not traditional risk factors, such as diabetes, high blood pressure or smoking. In addition, the predictive test according to the present disclosure may advantageously be used for patients who are on statin treatment to assess whether they have a residual risk to develop one or more cardiovascular events. The test can also be used for cardiovascular disease patients who have experienced a CV event to determine whether they have a high risk of developing one or more subsequent CV event.

The methods of predicting one or more coronary artery disease events according to the present disclosure, comprise the steps of measuring the concentrations of the at least one ceramide and the at least one phosphatidylcholine molecule, and optionally at least one additional ceramide and/or phosphatidylcholine from a sample, such as a blood sample, e.g., a serum and/or plasma sample. The novel combination, derived from the concentrations of the specific Cer and PC molecules, is used as a marker for future cardiovascular events.

Collecting information on a lipid biomarker, such as a lipid concentration, from the subject's sample, according to the methods of the present disclosure, can be performed via various chemical and high resolution analytical techniques. Particularly suitable analytical techniques include, but are not limited to, mass spectrometry (MS) and nuclear magnetic resonance (NMR) spectroscopy. Indeed, any high resolution technique capable of resolving individual lipid species and providing structural information of the same can be used to determine the lipid markers according to the present disclosure. For the purposes of the methods of the present disclosure, the lipid concentrations are typically determined by using mass spectrometry. The MS instrument can be coupled to a direct sample infusion method, such as a robotic nanoflow ion source device, or to a high performance separation method such as LC, GC, HPLC, UHPLC, or UPLC. In addition, nuclear magnetic resonance spectroscopy, fluorescence spectroscopy or dual polarisation interferometry, high performance separation methods such as HPLC, UHPLC or UPLC, an immunoassay, such as an ELISA, and/or the use of a binding moiety capable of specifically binding the lipid analyte are useful in this regard.

In the present disclosure, a novel combination of lipid biomarkers determined from a biological sample, e.g., a plasma or serum sample has been identified. Surprisingly, combinations of ceramide and phosphatidylcholine concentrations showed superior performance as predictive biomarkers for cardiovascular events, compared to the existing and conventionally used biomarkers.

Abbreviations

As used herein, "ACS" is acute coronary syndrome, "AMI" is acute myocardial infarction, "ApoA" is apolipoprotein A, "ApoAI" is apolipoprotein AI, "ApoAII" is apolipoprotein AII, "ApoB" is apolipoprotein B, "ApoC" is apolipoprotein C, "BMI" is body mass index, "BNP" is B-type natriuretic peptide, "$^{13}$C" is carbon-13 isotope, "CAC" is coronary artery calcification, "CAD" is coronary artery disease, "Cer" is ceramide, "CETP" is cholesteryl ester transfer protein, "CHD" is coronary heart disease, "CRP" is C-reactive protein, "CT" is computed tomography, "CV" is cardiovascular, "CVD" is cardiovascular disease/ coronary vascular disease, "ELISA" is enzyme-linked immunosorbent assay ", FA" is fatty acid, "GC is gas chromatography, "GC×GC" is two-dimensional gas chromatography, "GDF15" is growth differentiation factor 15, "$^{2}$H" is deuterium, "HbA1c" is glycated haemoglobin A1c, "HDL" is high density lipoprotein, "HDL-C" is high density lipoprotein cholesterol, "HDL-P" is high density lipoprotein particle or high density lipoprotein particle number, "HMG-CoA" is 3-hydroxy-3-methyl-glutaryl-coenzyme A, "HPLC" is high performance liquid chromatography, "HR" is hazard ratio, "IHD" is ischemic heart disease, "IL-1 mAb" is interleukin-1 monoclonal antibody, "LC is liquid chromatography, "LC×LC" is two-dimensional liquid chromatography, "LDL" is low density lipoprotein, "LDL-C" is low density lipoprotein cholesterol, "LDL-P" is low density lipoprotein particle or low density lipoprotein particle number, "Lp(a) is lipoprotein (a), "Lp-PLA2" is lipoprotein-associated phospholipase A2, "MI" is myocardial infarction, "MRM" is multiple reaction monitoring, "MS" is mass spectrometry, "$^{15}$N" is nitrogen-15 isotope, "NMR" is nuclear magnetic resonance, "NT-proBNP" is N-terminal pro B-type natriuretic peptide, "PC" is phosphatidylcholine, "PCSK9" is proprotein convertase subtilisin/kexin type 9, "RNA" is ribonucleic acid, "SB" is sphingoid base, "SCH-48461" is (3R,4S)-1,4-bis(4-methoxyphenyl)-3-(3-phenyl-propyl)-2-azetidinone, "SD" is standard deviation, "siRNA" is small interfering RNA, "St2" is suppression of tumorigenicity 2, "TC" is total cholesterol, "TG" is triglyseride, "TMAO" is trimethylamine-N-oxide, "TNF-alpha mAb" is tumor necrosis factor alpha monoclonal antibody, "TNI" or "TnI" is troponin I or high sensitivity troponin I, "TNT" or "TnT" is troponin T or high sensitivity troponin T, "UHPLC" is ultra high performance liquid chromatography, "UPLC" is ultra performance liquid chromatography.

In addition, the following abbreviations are used in the present disclosure: "ACE" is angiotensin-converting enzyme, "ACL" is adenosine triphosphate citrate lyase, "ALA" is a-linolenic acid, "ARB" is angiotensin II receptor blocker, "ATP" is adenocine triphosphate, "CCTA" is coronary computed tomography angiography, "CK" is creatine kinase, "DHA" is docosahexaenoic acid, "ECG or EKG" is electrocardiography, "EPA" is eicosapentaenoic acid, "GLP1" is glucagon-like peptide 1, "MRI" is magnetic resonance imaging, "NM" is nuclear medicine, "PET" is positron-emission tomography, "SPECT" is single-photon emission computed tomography, "SGLT2" is sodium-glucose transporter 2, "ω-3 or n-3" is omega-3 and "ω-6 or n-6" is omega-6.

Definitions

In order that the present invention may be more readily understood, certain terms are defined herein. Additional definitions are set forth throughout the detailed description.

As used herein, "cardiovascular disease (CVD)" has its general meaning in the art and it is used to classify numerous conditions that affect the heart, heart valves, blood, and vasculature of the body, including coronary artery disease (CAD). The CVD may or may not involve atherosclerosis. In the present disclosure, the terms CVD and CAD may be used interchangeably.

As used herein, "coronary artery disease (CAD)", also known as "coronary heart disease (CHD)" and "ischemic heart disease (IHD)", is characterized by atherosclerosis in the coronary arteries. Atherosclerotic plaques narrow the coronary artery lumen decreasing blood flow to the heart.

When the flow of oxygen-rich blood to the heart is reduced or blocked, angina or myocardial infarction can occur.

In the present disclosure, "cardiovascular (CV) event" comprises stable angina pectoris, unstable angina pectoris, myocardial infarction (MI), acute myocardial infarction (AMI), acute coronary syndrome (ACS), stroke, transient ischemic attacks, deep vein thrombosis, heart failure, hospitalization for heart failure and cardiovascular death. Such events may involve atherosclerosis. In the present disclosure the terms CV event, CVD event, CAD event, CHD event, CV complication, CVD complication, CAD complication, CHD complication, CV outcome, CVD outcome, CAD outcome and CHD outcome may be used interchangeably.

In the present disclosure, "cardiovascular (CV) event" may also comprise peripheral artery disease (also called peripheral arterial disease) and different forms of arrhythmias, such as atrial fibrillation.

As used herein, the terms "subject", "patient" and "individual" are used interchangeably herein to refer to any mammalian subject for whom prediction, diagnosis or therapy is desired, particularly humans. The subject may be a healthy individual with no previous signs or symptoms of CVD. Or, the subject may have previously suffered or is suffering from CVD or CAD. The subject may also be suspected of suffering from CVD and/or being at high risk of developing CV events. The subject may or may not have previously suffered from a cardiovascular event, such as angina pectoris, myocardial infarction or stroke. The subject may or may not suffer from a metabolic disease, such as diabetes. In addition, the subject may or may not have normal levels of traditional lipid markers, such as total cholesterol, LDL or HDL, and/or may or may not have traditional risk factors, such as diabetes, high blood pressure or smoking.

The subject may be or may have been under a treatment, such as, but not limited to, a statin treatment, or may not have had any previous treatment or medication.

As used herein, a "sample" is a biological sample obtained from a subject or a group or population of subjects. The sample may be a blood sample, a serum sample, a plasma sample, a saliva sample, a urine sample, a tissue sample or a fraction thereof, such as a lipoprotein fraction. Blood serum and plasma samples are typical. The sample can be prepared with techniques well known in the art. In certain embodiments, the blood sample is a dried blood spot. In certain embodiments, the blood sample is dried on a filter.

In some embodiments, a blood sample may be collected as dried plasma or serum on a card. The card separates plasma or serum from a drop of blood and the separated plasma or serum sample is dried on the card.

As used herein, a "control" may be a control sample. A control may also be a concentration determined from a sample from a single healthy individual. The control may also be a sample that represents a combination of samples from a generalized population of healthy individuals. Alternatively, the control may be a control value, a score or a set of data concerning the biomarker in a sample previously determined, calculated or extrapolated, or may have yet to be determined, calculated or extrapolated, or may also be taken from the literature.

In some embodiments, the control sample may be previously obtained from the same subject or the control value may be obtained from a previously taken sample from the same subject. In other embodiments, the control sample or the control value may be obtained from another subject.

A "control" as used herein, i.e., a control value or a control sample, is typically representative of a group of subjects or a population of subjects. In this context, "representative" means that the lipid concentration(s) reflected by said control value to which a comparison is made in the context of the present disclosure correspond(s) to the average concentration value(s) of said lipid concentration(s) in corresponding individual samples from the subjects of said group or population. Likewise, in the case of a control sample "representative" means that the lipid concentration (s) in said control sample to which a comparison is made in the context of the present disclosure correspond(s) to the average concentration(s) of said lipid concentration(s) in corresponding individual samples from the subjects of said group or population. Typically, the concentrations of all lipid concentrations in said control sample correspond to the average concentrations of said lipid concentrations in corresponding individual samples from the subjects of said group or population. An individual with such values can be considered a "healthy individual" for the purposes of the present disclosure.

A control sample can be particularly suitably compared to the subject's sample if it has been obtained from the same type of biological tissue or source in the same, or essentially the same, manner. For example, if the subject's sample is a serum sample or a plasma sample, a corresponding control sample will likewise be a serum sample or a plasma sample, respectively.

In some embodiments, a control sample from a group of subjects or a control sample from a population of subjects in the sense of the present disclosure is obtained by mixing equal amounts of samples directly obtained from the subjects of said group or population, or by mixing equal amounts of fractions, constituents or reaction products thereof.

It will be appreciated that a useful control value for the purposes of the present disclosure is typically one that has been, or is, obtained using any one of the suitable control samples described herein.

In the context of the present disclosure, a control sample can be from a healthy individual, a generalized population of healthy individuals, a CVD patient that has remained free of any major CV events, or a group of CVD patients that have remained free of any major CV events.

In some embodiments of the methods described herein, a control may be a control value, e.g., a score or a combination value of the concentrations of the at least one ceramide of Formula I and the at least one phosphatidylcholine of Formula II or a combination value of the at least one ceramide of Formula I and the at least one phosphatidylcholine of Formula II and the at least one additional ceramide or phosphatidylcholine, selected from any of the Cer and PC species referred to in Table 1.

For the purposes of the present disclosure, lipids are named according to the following nomenclature: Cer is ceramide and PC is phosphatidylcholine.

As used herein, the nomenclature of ceramides (Cer) is presented as a first pair of numbers corresponding to the sphingoid base (SB) and a second pair of numbers corresponding to the fatty acid (FA) chain of the molecule. In SB and FA nomenclature, the first number of each pair refers to the number of carbon atoms in the SB or FA chain, and the second number refers to the number of carbon-carbon double bonds of the SB or FA chain.

As used herein, a ceramide (Cer) of Formula I refers to ceramide species with the following structure:

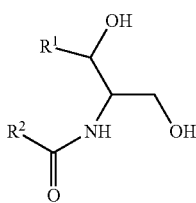

wherein $R^1$ is a saturated, mono-unsaturated or di-unsaturated alkyl chain having 11-17 carbon atoms, and wherein $R^2$ is a saturated, mono-unsaturated or di-unsaturated alkyl chain having 13-25 carbon atoms.

As used herein, the nomenclature of phosphatidylcholines (PC) is presented either as brutto species or molecular species. In brutto nomenclature, a first number refers to the total number of carbon atoms in the molecule and the second number refers to the total number of the carbon-carbon double bonds of the molecule. In molecular nomenclature, a first pair of numbers corresponds to the first fatty acid (FA) chain and a second pair of numbers corresponds to the second FA chain of the molecule. In FA nomenclature, the first number of each pair refers to the number of carbon atoms in the FA chain, and the second number refers to the number of carbon-carbon double bonds of the FA chain. In molecular nomenclature, the first FA chain may be either $R_1$ or $R_2$ in Formula II. Accordingly, the second FA chain may also be either $R_1$ or $R_2$ in Formula II.

As used herein, a phosphatidylcholine (PC) of Formula II refers to a phosphatidylcholine species with the following structure:

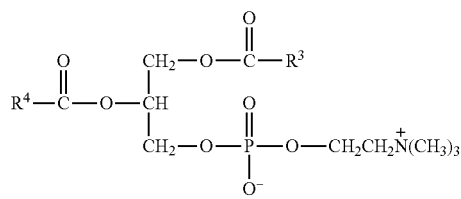

wherein $R^3$ and $R^4$ are be saturated, mono-unsaturated or polyunsaturated alkyl chains.

A "treatment" and "therapy" are used interchangeably in the present disclosure and may comprise any therapeutic treatment typically given to a subject at risk of developing CVD or a subject suffering from CVD, such as, but not limited to, administering a drug and/or providing therapeutic, behavioural and/or lifestyle modification to the subject. Behavioural and/or lifestyle modification may comprise, for example, lifestyle interventions and/or counselling, including, but not limited to, instructions, encouragement and/or follow-up regarding a healthy diet, weight management, physical activity/exercise and/or smoking cessation. A treatment may also be a surgical operation, such as angioplasty, stent placement or bypass surgery. A treatment may also include controlling of progression of CVD and/or its complications.

As used herein, a treatment may also be any cardiac and/or vascular operation, such as, but not limited to, revascularization, such as angioplasty, stent placement or bypass surgery, and any lifestyle modifications, such as lifestyle interventions and/or counselling, including, but not limited to, instructions, encouragement and/or follow-up regarding a healthy diet, weight management, physical activity/exercise, stress management and/or smoking cessation.

A treatment may further comprise any cardiac and/or vascular imaging and testing, such as, but not limited to, ultrasound, echocardiography, angiography, electrocardiography (ECG or EKG), cardiac stress test, computed tomography (CT), coronary CT calcium scan, coronary computed tomography angiography (CCTA), magnetic resonance imaging (MRI), nuclear medicine (NM) imaging, positron-emission tomography (PET), single-photon emission computed tomography (SPECT) and/or myocardial perfusion imaging.

A treatment may also comprise providing any medical and/or lifestyle management services to a subject. A treatment may be given by any healthcare provider, such as, but not limited to, a clinician, a physician, a medical doctor, a therapist, a nurse, a psychologist, a physiotherapist, a personal trainer and/or dietician.

A treatment may also comprise preventive measures, such as, but not limited to, administering a drug and/or providing therapeutic, behavioural and/or lifestyle modification to the subject. Behavioural and/or lifestyle modification may comprise, for example, lifestyle interventions and/or counselling, including, but not limited to, instructions, encouragement and/or follow-up regarding a healthy diet, weight management, physical activity/exercise, stress management and/or smoking cessation.

A treatment or prevention may further comprise requesting a test, for example, from a commercial laboratory, which provides the results of an assay useful for determining if a subject is in need of a treatment or prevention.

A "drug", "pharmaceutical", "medicament", "medicine" and "medication" are used interchangeably in the present disclosure and may comprise any pharmaceutical typically given to a subject having CVD, such as a statin, another lipid lowering/modifying drug, and/or a modulator of lipid concentrations.

As used herein, a drug may be, for example, an HMG-CoA reductase inhibitor (a statin or other HMG-CoA reductase inhibitor), niacin (nicotinic acid), a cholesterol absorption inhibitor (ezetimibe), a cholesteryl ester transfer protein (CETP) inhibitor, a bile acid sequestrant, a fibrate, a phytosterol, an anti-inflammatory drug (e.g. methotrexate, IL-1 mAb, TNF-alpha mAb), acetylsalicylic acid (aspirin) or a PCSK9 inhibitor, or a modulator of lipid concentrations selected from a small molecule, an antibody, an antisense RNA, a small interfering RNA (siRNA), and a natural or modified lipid, or any combination thereof.

As used herein, a drug may also be any pharmaceutical for treating or preventing CVD, diabetes, metabolic syndrome or other metabolic disorders, including, but not limited to, anticoagulant and antitrombotic drugs (e.g. rivaroxaban), diabetes medication (e.g. insulin, SGLT2 (sodium-glucose transporter 2) inhibitors, metformin, GLP1 (glucagon-like peptide 1) agonists), blood pressure medication (e.g. diuretics, beta-blockers, angiotensin-converting enzyme (ACE) inhibitors, angiotensin II receptor blockers (ARBs), calcium channel blockers, alpha-blockers, beta-blockers, renin inhibitors), heart failure medication, omega-3 (ω-3 or n-3) and omega-6 (ω-6 or n-6) polyunsaturated fatty acids (e.g. eicosapentaenoic acid (EPA), docosahexaenoic acid (DHA), a-linolenic acid (ALA)), ATP (adenosine triphosphate) citrate lyase (ACL) inhibitor (e.g. bempedoic acid), antisense oligonucleotide, or any combination thereof.

As used herein, "statins" is a class of lipid-lowering medications (HMG-CoA reductase inhibitors). Statin is selected from, but is not limited to, the group consisting of atorvastatin, cerivastatin, fluvastatin, fluvastatin XL, lovastatin, pitavastatin, pravastatin, rosuvastatin and simvastatin, or any combination thereof.

As used herein, statin may also be mevastatin.

For the purposes of the present disclosure, a "cholesterol absorption inhibitor" may be ezetimibe or SCH-48461; a cholesteryl ester transfer protein (CETP) inhibitor may be evacetrapib, anacetrapib or dalcetrapib; a bile acid sequestrant may be colesevelam, cholestyramine or colestipol; a fibrate may be fenofibrate, gemfibrozil, clofibrate, or bezafibrate, and the PCSK9 inhibitor is selected from, but is not limited to, a PCSK9 specific antibody, an siRNA, and a peptidomimetic.

A "modulator" according to the present disclosure may be a small molecule (<1500 dalton molecular weight, typically <800 dalton molecular weight), an antibody, an antisense RNA, a small interfering RNA (siRNA), or a natural or modified lipid.

As used herein, "effectiveness of a treatment" and "effectiveness of a therapy" is taken to mean the ability of a treatment to achieve the therapeutic purpose for which it is administered.

As used herein, a "CVD marker combination" refers to a specific combination of lipid biomarkers used for the methods and uses of the present disclosure. The CVD marker combination comprises at least one ceramide of Formula I and at least one phosphatidylcholine of Formula II. In some embodiments, the CVD marker combination further comprises at least one additional ceramide and/or at least one additional phosphatidylcholine, selected from any of the Cer and PC species referred to in Table 1 of the present disclosure. As used herein, the combination may be e.g. a ratio, sum, difference, product, remainder, value, score, calculation, formula, equation, algorithm, or any combination thereof, of the at least one ceramide of Formula I and at least one phosphatidylcholine of Formula II. In some embodiments, the combination may be calculated from the concentrations of the at least one ceramide of Formula I and at least one phosphatidylcholine of Formula II. In some embodiments, the CVD marker combination may be a concentration ratio of the at least one ceramide of Formula I and at least one phosphatidylcholine of Formula II. In some embodiments, the combination further comprises at least one additional ceramide and/or at least one additional phosphatidylcholine, selected from any of the Cer and PC species referred to in Table 1 of the present disclosure.

In some embodiments, the at least one additional Cer is at least 2, at least 3, at least 4, at least 5, at least 6, at least 7, at least 8, at least 9 or at least 10 additional Cers, selected from any of the Cer species referred to in Table 1. In some embodiments, the at least one additional Cer is a combination, including, but not limited to, a Cer/Cer ratio, of at least 2, at least 3, at least 4, at least 5, at least 6, at least 7, at least 8, at least 9 or at least 10 additional Cers. The combination may also be another combination as described herein.

In some embodiments, the at least one additional PC is at least 2, at least 3, at least 4, at least 5, at least 6, at least 7, at least 8, at least 9 or at least 10 additional PCs, selected from any of the PC species referred to in Table 1. In some embodiments, the at least one additional PC is a combination, including, but not limited to, a PC/PC ratio, of at least 2, at least 3, at least 4, at least 5, at least 6, at least 7, at least 8, at least 9 or at least 10 additional PCs. The combination may also be another combination as described herein.

In some embodiments, the CVD marker combination further comprises other cardiovascular biomarkers, including, but not limited to, LDL, LDL-C, LDL-P, HDL, HDL-C, HDL-P, any other lipoprotein subgroup composition or particle number, TC, TG, CRP, troponin T, troponin I, BNP, NT-proBNP, Cystatin C, HbA1c, glucose, St2, Galectin, TMAO, Lp-PLA2, GDF15, Lp(a), ApoB, ApoAI, ApoAII, ApoC, or any combination thereof. In some embodiments, the CVD marker combination further comprises other personal information or health data, such as sex, age, blood pressure, smoking status, diabetes, lipid lowering treatment or other medication, history of cardiovascular events, ethnic background, geographical location, medical imaging data, e.g. from angiography or computed tomography (CT), or any combination thereof. In some embodiments, the marker combination may be constructed by linear combinations, regression models, other unsupervised or supervised frequentist or Bayesian statistical classification or machine learning methods, such as support vector machines, kernel estimations, decision trees or, neural networks.

In some embodiments, the CVD marker combination may further comprise any other cardiovascular or metabolic biomarker, including, but not limited to creatine kinase (CK).

In some embodiments, the marker combination is a continuous or discrete scoring systems based on the Cer, PC, Cer/PC, Cer/Cer, PC/Cer, PC/PC or other cardiovascular biomarkers. For discrete scoring, the points may be given based on intervals with non-equal probabilities, quantiles or other cut-off values, determined from the same or other populations, of the individual score components.

In the present disclosure, the terms CVD marker combination, CVD biomarker combination, CV marker combination, CV biomarker combination, marker combination, biomarker combination, lipid marker combination and combination may be used interchangeable.

As used herein, a "standard combination" refers to a specific combination of lipid standards used for the methods and uses of the present disclosure. The standard combination comprises at least one ceramide of Formula I and at least one phosphatidylcholine of Formula II. In some embodiments, the standard combination further comprises at least one additional ceramide and/or phosphatidylcholine, selected from any of the Cer and PC species referred to in Table 1 of the present disclosure. In some embodiments, one or more of the components of the standard combination is isotope-labelled. In some embodiments, the isotope of the isotope-labelled component is deuterium ($^2H$). In some embodiments, the isotope of the isotope-labelled component is $^{13}C$ or $^{15}N$.

As used herein, a "composition" or "kit" may be any combination of any standard(s), control(s), reagent(s), solution(s) or solvent(s) used for the methods and uses of the present disclosure. The composition or kit may comprise at least one ceramide of Formula I and at least one phosphatidylcholine of Formula II. In some embodiments, the composition or kit further comprises at least one additional ceramide and/or phosphatidylcholine, selected from any of the Cer and PC species referred to in Table 1 of the present disclosure. In some embodiments, one or more of the components of the composition or kit is isotope-labelled. In some embodiments, the isotope of the isotope-labelled component is deuterium. In some embodiments, the isotope of the isotope-labelled component is $^{13}C$ or $^{15}N$.

As used herein, the composition or kit may further include container(s), use instruction(s) for the methods or uses disclosed herein, and/or other element(s) for performing the methods or uses disclosed in the present disclosure. In some embodiments, the composition or kit includes element(s) for collecting a blood sample, for example, a dried blood spot on a filter.

The composition or kit may be purchased from a commercial manufacturer or prepared in-house in a laboratory. The composition or kit may be a test kit for used in a laboratory or a home use test kit (over-the-counter test).

In certain embodiments, the composition or kit is a combination of any standard(s), control(s), reagent(s), solution(s) or solvent(s) used for assaying a concentration of at least one ceramide of Formula I and a concentration of at least one phosphatidylcholine of Formula II and optionally a concentration of at least one additional ceramide and/or phosphatidylcholine, selected from any of the Cer and PC species referred to in Table 1 of the present disclosure.

The composition or kit may be used in assays performed with various chemical and high-resolution analytical techniques, such as, but not limited to, mass spectrometry (MS) and nuclear magnetic resonance (NMR). The MS analysis can be coupled to another high performance separation method, such as gas chromatography (GC), two-dimensional gas chromatography (GC×GC), liquid chromatography (LC), two-dimensional liquid chromatography (LC× LC), high performance liquid chromatography (HPLC) or ultra-high performance liquid chromatography (UHPLC).

As used herein, a "reagent" may be any standard(s), control(s), substance(s), compound(s), solution(s), solvent (s), agent(s), ingredient(s), preparation(s), or any combination thereof used for the methods and uses of the present disclosure. A reagent may also be a combination or mixture of any standard(s), control(s), substance(s), compound(s), solution(s), solvent(s), agent(s), ingredient(s) and preparation(s) used in the methods and uses of the present disclosure.

In some embodiments, one or more of any components of a reagent is isotope-labelled. In some embodiments, the isotope of the isotope-labelled component is deuterium. In some embodiments, the isotope of the isotope-labelled component is $^{13}C$ or $^{15}N$.

In some embodiments, a reagent is used for assaying in a sample a concentration of at least one ceramide (Cer) of Formula I and a concentration of at least one phosphatidylcholine (PC) of Formula II. In some embodiments, a reagent is further used for assaying a concentration of at least one additional ceramide and/or phosphatidylcholine, selected from any of the Cer and PC species referred to in Table 1 of the present disclosure.

In some embodiments, a reagent is used in a preparation of a reagent, kit or composition for performing the methods and uses of the present disclosure.

For the purposes of the present disclosure, the terms "obtaining data", "collecting data", "obtaining information" and "collecting information" may be used interchangeably.

As used herein, "determining" in reference to a biomarker as disclosed herein refers to quantitatively or relatively determining an amount of a biomarker in a sample. For quantitative determination, either the absolute or precise amount of the biomarker in a sample is determined. The relative amount or level of a biomarker in a sample, may alternatively be determined, e.g., the biomarker amount in the sample is determined to be enlarged or diminished with respect to a control as described herein.

As used herein, "assaying", "detecting", "analyzing" or "generating quantitative data" refers to a measurement of a quantity, amount, abundance, level or concentration of the biomarkers of the present disclosure in a sample using a laboratory apparatus, equipment or device, such as, but not limited to, mass spectrometry.

As used herein, a "biomarker", "marker", "CVD marker", "CVD biomarker", "CV marker", "CV biomarker", "lipid marker" and "lipid biomarker" may be used interchangeably.

As used herein, a "combination", "group", "set", "composition" and "mixture" may be used interchangeably.

As used herein, and according to Table 1, a "direction of change" refers to a change in a quantity, amount, abundance, level or concentration of the biomarker in a sample from a subject when the subject is having a risk of developing one or more cardiovascular events, when compared to a control. When evaluating the effectiveness of a CVD treatment in a subject, according to some aspects of the percent disclosure, directions of change are opposite of which are presented in Table 1.

As used herein, a "risk" refers to a low, intermediate or high risk of developing one or more cardiovascular events.

The terms "the disclosure, description or invention", "in accordance with the disclosure, description or invention", "according to the disclosure, description or invention", "the present disclosure, description or invention", as used herein, are intended to refer to all aspects and embodiments of the disclosure described and/or claimed herein.

As used herein, the term "comprising" is to be construed as encompassing both "including" and "consisting of".

EXAMPLES

Example 1. Materials and Methods

Description of Study Cohorts and Samples

Plasma samples were obtained from 3700 adult subjects, with suspected stable angina pectoris, who underwent coronary angiography. These subjects were followed up on average for 10 years for cardiovascular (CV) death or CV events.

In addition to the first study cohort, samples were also analysed from another study cohort, a population study cohort. 7300 serum samples were analysed from adult subjects of the cohort. The subjects were followed up on average 16 years for several cardiovascular outcomes, e.g. myocardial infarction, heart failure and CV death.

Analytical Methods

For quantification of lipids, serum samples were extracted using a modified Folch lipid extraction performed on a Hamilton MICROLAB® STAR™ pipetting system robot, as described in Jung H R et al., High throughput quantitative molecular lipidomics. Biochim Biophys Acta. 2011 November; 1811(11):925-34, which is hereby incorporated by reference in its entirety. Samples were spiked with known amounts of non-endogeneous synthetic internal standards. After lipid extraction, samples were reconstituted in chloroform:methanol (1:2, v/v) and a synthetic external standard was post-extract spiked to the extracts. The extracts were stored at −20° C. prior to MS analysis.

Ceramides and phospholipids (e.g. phosphatidylcholines) were analyzed on a hybrid triple quadrupole/linear ion trap mass spectrometer (5500 QTRAP® mass spectrometer) equipped with an ultra high pressure liquid chromatography (UHPLC) system (EKSIGENT™ ULTRALC 100 liquid chromatography system) using multiple reaction monitoring (MRM). Ceramides were analysed based on method in negative ion mode based on the description by Sullards M C et al., Structure-specific, quantitative methods for analysis of sphingolipids by liquid chromatography-tandem mass spectrometry: "inside-out" sphingolipidomics. Methods Enzymol. 2007; 432:83-115. Phospholipids were analyzed based on previously published method by Niemi et al., Ovarian tumours of different histologic type and clinical stage induce similar changes in lipid metabolism. British Journal of Cancer. 2018; 119:847-854.

Statistical Analyses

All statistical analyses were performed using R software. Cox proportional hazards models (constructed using the R package survival) were used to determine the association of variables or their combinations to outcome of the study subjects. The hazard ratios (HRs) obtained from the cox regression models are expressed per standard deviation (SD). Linear combinations of variables were constructed using binary logistic regression models, and C-statistics for cox regression models were calculated using the Hmisc package.

Example 2. Results

Tables 2-12 present results of the first study cohort and tables 13-18 of the second study cohort.

Table 2 shows that ceramide vs. phosphatidylcholine or ceramide vs. ceramide ratios predict more accurately the CV events than the corresponding ceramides or phosphatidylcholines alone. In this example, the cox models were adjusted with age and stratified for sex. As shown in the Table 2, lipid ratios have lower p-values and higher C-statistics as compared to the individual lipid components.

TABLE 2

The p-value of lipid ratios are lower than the corresponding lipids alone.

| | Lipid ratio | | | Denominator lipid | | | Numerator lipid | | |
|---|---|---|---|---|---|---|---|---|---|
| Lipid ratio | HR (95% CI) | p-value | C-stat | HR (95% CI) | p-value | C-stat | HR (95% CI) | p-value | C-stat |
| Cer(d18:1/16:0)/PC 37:6 | 1.27 (1.20, 1.35) | 3.9E−15 | 0.639 | 1.23 (1.15, 1.31) | 4.4E−10 | 0.629 | 0.82 (0.76, 0.89) | 3.0E−06 | 0.630 |
| Cer(d18:1/24:1)/PC 37:6 | 1.26 (1.19, 1.34) | 6.1E−15 | 0.641 | 1.16 (1.09, 1.24) | 6.7E−06 | 0.626 | 0.82 (0.76, 0.89) | 3.0E−06 | 0.630 |
| Cer(d18:1/18:0)/PC 37:6 | 1.25 (1.18, 1.33) | 4.7E−14 | 0.639 | 1.21 (1.13, 1.28) | 7.8E−09 | 0.630 | 0.82 (0.76, 0.89) | 3.0E−06 | 0.630 |
| Cer(d18:1/16:0)/PC 36:6 | 1.21 (1.15, 1.28) | 6.7E−13 | 0.635 | 1.23 (1.15, 1.31) | 4.4E−10 | 0.629 | 0.86 (0.79, 0.93) | 1.8E−04 | 0.627 |
| Cer(d18:1/16:0)/PC 16:0/22:5 | 1.27 (1.19, 1.35) | 7.9E−13 | 0.634 | 1.23 (1.15, 1.31) | 4.4E−10 | 0.629 | 0.93 (0.86, 1.01) | 7.4E−02 | 0.620 |
| Cer(d18:1/18:0)/PC 39:6 | 1.24 (1.17, 1.32) | 9.8E−13 | 0.634 | 1.21 (1.13, 1.28) | 7.8E−09 | 0.630 | 0.83 (0.76, 0.89) | 2.4E−06 | 0.629 |
| Cer(d18:1/24:1)/PC 36:6 | 1.22 (1.15, 1.29) | 1.6E−12 | 0.638 | 1.16 (1.09, 1.24) | 6.7E−06 | 0.626 | 0.86 (0.79, 0.93) | 1.8E−04 | 0.627 |
| Cer(d18:1/18:0)/PC 36:6 | 1.20 (1.14, 1.27) | 6.1E−12 | 0.636 | 1.21 (1.13, 1.28) | 7.8E−09 | 0.630 | 0.86 (0.79, 0.93) | 1.8E−04 | 0.627 |
| Cer(d18:1/18:0)/PC 16:0/22:5 | 1.24 (1.17, 1.33) | 7.8E−12 | 0.635 | 1.21 (1.13, 1.28) | 7.8E−09 | 0.630 | 0.93 (0.86, 1.01) | 7.4E−02 | 0.620 |
| Cer(d18:1/16:0)/PC 16:0/22:6 | 1.22 (1.16, 1.30) | 8.5E−12 | 0.633 | 1.23 (1.15, 1.31) | 4.4E−10 | 0.629 | 0.90 (0.84, 0.98) | 9.3E−03 | 0.622 |
| Cer(d18:1/20:0)/PC 37:6 | 1.23 (1.16, 1.30) | 1.0E−11 | 0.635 | 1.15 (1.08, 1.22) | 4.9E−06 | 0.625 | 0.82 (0.76, 0.89) | 3.0E−06 | 0.630 |
| Cer(d18:1/18:0)/PC 16:0/22:6 | 1.24 (1.16, 1.32) | 1.1E−11 | 0.635 | 1.21 (1.13, 1.28) | 7.8E−09 | 0.630 | 0.90 (0.84, 0.98) | 9.3E−03 | 0.622 |
| Cer(d18:1/16:0)/PC 39:6 | 1.22 (1.15, 1.30) | 1.6E−11 | 0.632 | 1.23 (1.15, 1.31) | 4.4E−10 | 0.629 | 0.83 (0.76, 0.89) | 2.4E−06 | 0.629 |
| Cer(d18:1/24:1)/PC 39:6 | 1.22 (1.15, 1.29) | 1.7E−11 | 0.633 | 1.16 (1.09, 1.24) | 6.7E−06 | 0.626 | 0.83 (0.76, 0.89) | 2.4E−06 | 0.629 |
| Cer(d18:1/24:1)/PC 16:0/22:6 | 1.20 (1.13, 1.26) | 7.0E−11 | 0.634 | 1.16 (1.09, 1.24) | 6.7E−06 | 0.626 | 0.90 (0.84, 0.98) | 9.3E−03 | 0.622 |
| Cer(d18:2/16:0)/PC 37:6 | 1.22 (1.15, 1.30) | 1.8E−10 | 0.634 | 1.09 (1.01, 1.17) | 1.9E−02 | 0.619 | 0.82 (0.76, 0.89) | 3.0E−06 | 0.630 |
| Cer(d18:1/18:0)/PC 38:7 | 1.16 (1.11, 1.22) | 7.5E−10 | 0.631 | 1.21 (1.13, 1.28) | 7.8E−09 | 0.630 | 0.88 (0.81, 0.96) | 3.4E−03 | 0.625 |
| Cer(d18:1/20:0)/PC 36:6 | 1.16 (1.11, 1.22) | 9.0E−10 | 0.632 | 1.15 (1.08, 1.22) | 4.9E−06 | 0.625 | 0.86 (0.79, 0.93) | 1.8E−04 | 0.627 |
| Cer(d18:1/24:1)/PC 35:5 | 1.21 (1.14, 1.29) | 1.2E−09 | 0.631 | 1.16 (1.09, 1.24) | 6.7E−06 | 0.626 | 0.84 (0.78, 0.91) | 4.1E−05 | 0.625 |
| Cer(d18:1/20:0)/PC 39:6 | 1.20 (1.13, 1.28) | 1.3E−09 | 0.630 | 1.15 (1.08, 1.22) | 4.9E−06 | 0.625 | 0.83 (0.76, 0.89) | 2.4E−06 | 0.629 |
| Cer(d18:1/22:0)/Cer(d18:2/24:0) | 1.21 (1.14, 1.29) | 1.3E−09 | 0.632 | 1.14 (1.07, 1.22) | 1.1E−04 | 0.624 | 0.97 (0.90, 1.05) | 4.5E−01 | 0.620 |
| Cer(d18:1/24:1)/PC 38:7 | 1.16 (1.10, 1.21) | 1.5E−09 | 0.631 | 1.16 (1.09, 1.24) | 6.7E−06 | 0.626 | 0.88 (0.81, 0.96) | 3.4E−03 | 0.625 |
| Cer(d16:1/16:0)/PC 37:6 | 1.23 (1.15, 1.31) | 1.9E−09 | 0.633 | 1.08 (1.01, 1.16) | 2.6E−02 | 0.620 | 0.82 (0.76, 0.89) | 3.0E−06 | 0.630 |
| Cer(d16:1/16:0)/PC 36:6 | 1.20 (1.13, 1.28) | 2.7E−09 | 0.632 | 1.08 (1.01, 1.16) | 2.6E−02 | 0.620 | 0.86 (0.79, 0.93) | 1.8E−04 | 0.627 |
| Cer(d18:1/18:0)/PC 17:0/18:1 | 1.21 (1.14, 1.29) | 3.9E−09 | 0.633 | 1.21 (1.13, 1.28) | 7.8E−09 | 0.630 | 1.00 (0.93, 1.08) | 9.7E−01 | 0.619 |
| Cer(d18:2/24:1)/PC 37:6 | 1.20 (1.13, 1.28) | 4.4E−09 | 0.633 | 1.06 (0.98, 1.13) | 1.3E−01 | 0.619 | 0.82 (0.76, 0.89) | 3.0E−06 | 0.630 |

TABLE 2-continued

The p-value of lipid ratios are lower than the corresponding lipids alone.

| Lipid ratio | Lipid ratio | | | Denominator lipid | | | Numerator lipid | | |
|---|---|---|---|---|---|---|---|---|---|
| | HR (95% CI) | p-value | C-stat | HR (95% CI) | p-value | C-stat | HR (95% CI) | p-value | C-stat |
| Cer(d18:1/20:0)/PC 16:0/22:5 | 1.21 (1.13, 1.29) | 4.8E−09 | 0.630 | 1.15 (1.08, 1.22) | 4.9E−06 | 0.625 | 0.93 (0.86, 1.01) | 7.4E−02 | 0.620 |
| Cer(d18:1/18:0)/PC 35:4 | 1.20 (1.13, 1.28) | 5.0E−09 | 0.633 | 1.21 (1.13, 1.28) | 7.8E−09 | 0.630 | 0.95 (0.88, 1.02) | 1.7E−01 | 0.620 |
| Cer(d18:1/24:1)/PC 16:0/22:5 | 1.21 (1.13, 1.29) | 6.0E−09 | 0.631 | 1.16 (1.09, 1.24) | 6.7E−06 | 0.626 | 0.93 (0.86, 1.01) | 7.4E−02 | 0.620 |
| Cer(d18:1/22:0)/PC 37:6 | 1.21 (1.13, 1.29) | 6.4E−09 | 0.631 | 1.14 (1.07, 1.22) | 1.1E−04 | 0.624 | 0.82 (0.76, 0.89) | 3.0E−06 | 0.630 |
| Cer(d18:2/16:0)/PC 36:6 | 1.18 (1.12, 1.25) | 9.0E−09 | 0.630 | 1.09 (1.01, 1.17) | 1.9E−02 | 0.619 | 0.86 (0.79, 0.93) | 1.8E−04 | 0.627 |
| Cer(d18:1/20:0)/PC 16:0/22:6 | 1.20 (1.13, 1.28) | 1.1E−08 | 0.629 | 1.15 (1.08, 1.22) | 4.9E−06 | 0.625 | 0.90 (0.84, 0.98) | 9.3E−03 | 0.622 |
| Cer(d20:1/24:1)/PC 39:6 | 1.19 (1.12, 1.27) | 1.5E−08 | 0.631 | 1.09 (1.02, 1.16) | 1.3E−02 | 0.622 | 0.83 (0.76, 0.89) | 2.4E−06 | 0.629 |
| Cer(d18:1/22:0)/PC 36:6 | 1.19 (1.12, 1.26) | 2.0E−08 | 0.631 | 1.14 (1.07, 1.22) | 1.1E−04 | 0.624 | 0.86 (0.79, 0.93) | 1.8E−04 | 0.627 |
| Cer(d18:1/20:0)/PC 38:7 | 1.16 (1.10, 1.21) | 2.3E−08 | 0.629 | 1.15 (1.08, 1.22) | 4.9E−06 | 0.625 | 0.88 (0.81, 0.96) | 3.4E−03 | 0.625 |
| Cer(d16:1/18:0)/PC 37:6 | 1.21 (1.13, 1.29) | 2.4E−08 | 0.631 | 1.08 (1.01, 1.16) | 3.2E−02 | 0.620 | 0.82 (0.76, 0.89) | 3.0E−06 | 0.630 |
| Cer(d18:2/18:0)/PC 37:6 | 1.19 (1.12, 1.27) | 5.8E−08 | 0.631 | 1.06 (0.99, 1.14) | 8.7E−02 | 0.619 | 0.82 (0.76, 0.89) | 3.0E−06 | 0.630 |
| Cer(d20:1/24:1)/PC 35:5 | 1.17 (1.10, 1.23) | 6.1E−08 | 0.628 | 1.09 (1.02, 1.16) | 1.3E−02 | 0.622 | 0.84 (0.78, 0.91) | 4.1E−05 | 0.625 |
| Cer(d20:1/24:1)/PC 37:6 | 1.16 (1.10, 1.22) | 7.0E−08 | 0.631 | 1.09 (1.02, 1.16) | 1.3E−02 | 0.622 | 0.82 (0.76, 0.89) | 3.0E−06 | 0.630 |
| Cer(d16:1/18:0)/PC 36:6 | 1.19 (1.12, 1.27) | 7.5E−08 | 0.631 | 1.08 (1.01, 1.16) | 3.2E−02 | 0.620 | 0.86 (0.79, 0.93) | 1.8E−04 | 0.627 |
| Cer(d18:1/24:1)/PC 18:0/20:5 | 1.18 (1.11, 1.25) | 8.4E−08 | 0.626 | 1.16 (1.09, 1.24) | 6.7E−06 | 0.626 | 0.88 (0.81, 0.95) | 9.7E−04 | 0.622 |
| Cer(d20:1/24:1)/PC 38:7 | 1.16 (1.10, 1.23) | 9.3E−08 | 0.628 | 1.09 (1.02, 1.16) | 1.3E−02 | 0.622 | 0.88 (0.81, 0.96) | 3.4E−03 | 0.625 |
| Cer(d18:1/24:1)/PC 38:6 | 1.17 (1.10, 1.24) | 1.5E−07 | 0.629 | 1.16 (1.09, 1.24) | 6.7E−06 | 0.626 | 0.92 (0.85, 0.99) | 3.1E−02 | 0.620 |
| Cer(d18:1/24:1)/PC 16:0/20:5 | 1.18 (1.11, 1.25) | 1.5E−07 | 0.626 | 1.16 (1.09, 1.24) | 6.7E−06 | 0.626 | 0.90 (0.83, 0.97) | 5.1E−03 | 0.621 |
| Cer(d20:1/24:1)/PC 36:6 | 1.15 (1.09, 1.21) | 2.2E−07 | 0.630 | 1.09 (1.02, 1.16) | 1.3E−02 | 0.622 | 0.86 (0.79, 0.93) | 1.8E−04 | 0.627 |
| Cer(d18:1/20:0)/PC 38:6 | 1.19 (1.11, 1.26) | 2.3E−07 | 0.627 | 1.15 (1.08, 1.22) | 4.9E−06 | 0.625 | 0.92 (0.85, 0.99) | 3.1E−02 | 0.620 |
| Cer(d18:1/20:0)/Cer(d18:2/24:0) | 1.12 (1.07, 1.17) | 2.3E−07 | 0.627 | 1.15 (1.08, 1.22) | 4.9E−06 | 0.625 | 0.97 (0.90, 1.05) | 4.5E−01 | 0.620 |
| Cer(d18:1/22:0)/Cer(d16:1/24:0) | 1.19 (1.11, 1.27) | 2.7E−07 | 0.628 | 1.14 (1.07, 1.22) | 1.1E−04 | 0.624 | 0.96 (0.90, 1.04) | 3.4E−01 | 0.619 |
| Cer(d18:2/16:0)/PC 38:7 | 1.15 (1.09, 1.21) | 3.1E−07 | 0.627 | 1.09 (1.01, 1.17) | 1.9E−02 | 0.619 | 0.88 (0.81, 0.96) | 3.4E−03 | 0.625 |
| Cer(d20:1/24:1)/PC 18:0/20:5 | 1.17 (1.10, 1.24) | 3.5E−07 | 0.627 | 1.09 (1.02, 1.16) | 1.3E−02 | 0.622 | 0.88 (0.81, 0.95) | 9.7E−04 | 0.622 |
| Cer(d20:1/22:0)/PC 36:6 | 1.16 (1.10, 1.23) | 4.2E−07 | 0.629 | 1.10 (1.03, 1.18) | 4.6E−03 | 0.622 | 0.86 (0.79, 0.93) | 1.8E−04 | 0.627 |
| Cer(d18:1/24:1)/PC 40:8 | 1.13 (1.08, 1.19) | 6.2E−07 | 0.627 | 1.16 (1.09, 1.24) | 6.7E−06 | 0.626 | 0.90 (0.84, 0.97) | 8.0E−03 | 0.623 |
| Cer(d16:1/20:0)/PC 36:6 | 1.17 (1.10, 1.25) | 7.0E−07 | 0.628 | 1.08 (1.00, 1.16) | 4.3E−02 | 0.619 | 0.86 (0.79, 0.93) | 1.8E−04 | 0.627 |
| Cer(d18:1/22:0)/PC 38:7 | 1.15 (1.09, 1.21) | 9.3E−07 | 0.627 | 1.14 (1.07, 1.22) | 1.1E−04 | 0.624 | 0.88 (0.81, 0.96) | 3.4E−03 | 0.625 |
| Cer(d20:1/22:0)/PC 38:7 | 1.15 (1.09, 1.21) | 9.6E−07 | 0.626 | 1.10 (1.03, 1.18) | 4.6E−03 | 0.622 | 0.88 (0.81, 0.96) | 3.4E−03 | 0.625 |
| Cer(d18:2/24:1)/PC 36:6 | 1.16 (1.09, 1.23) | 1.2E−06 | 0.630 | 1.06 (0.98, 1.13) | 1.3E−01 | 0.619 | 0.86 (0.79, 0.93) | 1.8E−04 | 0.627 |
| Cer(d20:1/24:1)/PC 16:0/20:5 | 1.17 (1.10, 1.24) | 1.2E−06 | 0.626 | 1.09 (1.02, 1.16) | 1.3E−02 | 0.622 | 0.90 (0.83, 0.97) | 5.1E−03 | 0.621 |
| Cer(d18:1/22:0)/PC 16:0/22:5 | 1.17 (1.10, 1.25) | 1.2E−06 | 0.626 | 1.14 (1.07, 1.22) | 1.1E−04 | 0.624 | 0.93 (0.86, 1.01) | 7.4E−02 | 0.620 |
| Cer(d18:1/22:0)/PC 37:2 | 1.16 (1.09, 1.23) | 1.4E−06 | 0.625 | 1.14 (1.07, 1.22) | 1.1E−04 | 0.624 | 0.99 (0.92, 1.06) | 7.9E−01 | 0.619 |
| Cer(d18:2/18:0)/PC 36:6 | 1.16 (1.09, 1.23) | 1.6E−06 | 0.629 | 1.06 (0.99, 1.14) | 8.7E−02 | 0.619 | 0.86 (0.79, 0.93) | 1.8E−04 | 0.627 |
| Cer(d18:1/20:0)/PC 35:5 | 1.15 (1.09, 1.22) | 1.8E−06 | 0.626 | 1.15 (1.08, 1.22) | 4.9E−06 | 0.625 | 0.84 (0.78, 0.91) | 4.1E−05 | 0.625 |
| Cer(d16:1/18:0)/PC 35:5 | 1.16 (1.09, 1.24) | 3.0E−06 | 0.626 | 1.08 (1.01, 1.16) | 3.2E−02 | 0.620 | 0.84 (0.78, 0.91) | 4.1E−05 | 0.625 |
| Cer(d18:1/20:0)/PC 35:4 | 1.15 (1.09, 1.22) | 3.1E−06 | 0.628 | 1.15 (1.08, 1.22) | 4.9E−06 | 0.625 | 0.95 (0.88, 1.02) | 1.7E−01 | 0.620 |

TABLE 2-continued

The p-value of lipid ratios are lower than the corresponding lipids alone.

| Lipid ratio | Lipid ratio | | | Denominator lipid | | | Numerator lipid | | |
|---|---|---|---|---|---|---|---|---|---|
| | HR (95% CI) | p-value | C-stat | HR (95% CI) | p-value | C-stat | HR (95% CI) | p-value | C-stat |
| Cer(d16:1/16:0)/PC 38:7 | 1.13 (1.07, 1.19) | 3.9E−06 | 0.625 | 1.08 (1.01, 1.16) | 2.6E−02 | 0.620 | 0.88 (0.81, 0.96) | 3.4E−03 | 0.625 |
| Cer(d20:1/24:1)/PC 16:0/22:6 | 1.16 (1.09, 1.23) | 3.9E−06 | 0.628 | 1.09 (1.02, 1.16) | 1.3E−02 | 0.622 | 0.90 (0.84, 0.98) | 9.3E−03 | 0.622 |
| Cer(d16:1/18:0)/PC 38:7 | 1.14 (1.08, 1.20) | 4.1E−06 | 0.626 | 1.08 (1.01, 1.16) | 3.2E−02 | 0.620 | 0.88 (0.81, 0.96) | 3.4E−03 | 0.625 |
| Cer(d20:1/24:1)/PC 38:5 | 1.16 (1.09, 1.23) | 4.3E−06 | 0.625 | 1.09 (1.02, 1.16) | 1.3E−02 | 0.622 | 0.89 (0.82, 0.96) | 3.5E−03 | 0.621 |
| Cer(d18:1/20:0)/PC 40:5 | 1.15 (1.09, 1.23) | 4.4E−06 | 0.626 | 1.15 (1.08, 1.22) | 4.9E−06 | 0.625 | 0.94 (0.87, 1.01) | 1.1E−01 | 0.620 |
| Cer(d20:1/23:0)/PC 36:6 | 1.15 (1.08, 1.22) | 4.6E−06 | 0.627 | 1.05 (0.98, 1.13) | 1.4E−01 | 0.620 | 0.86 (0.79, 0.93) | 1.8E−04 | 0.627 |
| Cer(d18:2/16:0)/PC 16:0/22:5 | 1.17 (1.09, 1.25) | 6.0E−06 | 0.624 | 1.09 (1.01, 1.17) | 1.9E−02 | 0.619 | 0.93 (0.86, 1.01) | 7.4E−02 | 0.620 |
| Cer(d18:2/24:1)/PC 35:5 | 1.16 (1.09, 1.23) | 8.4E−06 | 0.626 | 1.06 (0.98, 1.13) | 1.3E−01 | 0.619 | 0.84 (0.78, 0.91) | 4.1E−05 | 0.625 |
| Cer(d18:2/18:0)/PC 38:7 | 1.13 (1.07, 1.20) | 9.2E−06 | 0.626 | 1.06 (0.99, 1.14) | 8.7E−02 | 0.619 | 0.88 (0.81, 0.96) | 3.4E−03 | 0.625 |
| Cer(d18:2/18:0)/PC 35:5 | 1.16 (1.09, 1.24) | 9.4E−06 | 0.625 | 1.06 (0.99, 1.14) | 8.7E−02 | 0.619 | 0.84 (0.78, 0.91) | 4.1E−05 | 0.625 |
| Cer(d16:1/16:0)/PC 35:5 | 1.16 (1.09, 1.24) | 9.5E−06 | 0.625 | 1.08 (1.01, 1.16) | 2.6E−02 | 0.620 | 0.84 (0.78, 0.91) | 4.1E−05 | 0.625 |
| Cer(d18:1/22:0)/PC 35:4 | 1.15 (1.08, 1.22) | 1.3E−05 | 0.627 | 1.14 (1.07, 1.22) | 1.1E−04 | 0.624 | 0.95 (0.88, 1.02) | 1.7E−01 | 0.620 |
| Cer(d18:1/22:0)/PC 16:0/22:6 | 1.16 (1.08, 1.23) | 1.4E−05 | 0.625 | 1.14 (1.07, 1.22) | 1.1E−04 | 0.624 | 0.90 (0.84, 0.98) | 9.3E−03 | 0.622 |
| Cer(d18:2/16:0)/PC 16:0/22:6 | 1.15 (1.08, 1.22) | 1.6E−05 | 0.624 | 1.09 (1.01, 1.17) | 1.9E−02 | 0.619 | 0.90 (0.84, 0.98) | 9.3E−03 | 0.622 |
| Cer(d18:2/16:0)/PC 40:8 | 1.11 (1.06, 1.16) | 1.8E−05 | 0.624 | 1.09 (1.01, 1.17) | 1.9E−02 | 0.619 | 0.90 (0.84, 0.97) | 8.0E−03 | 0.623 |
| Cer(d20:1/23:0)/PC 38:7 | 1.13 (1.07, 1.19) | 2.0E−05 | 0.625 | 1.05 (0.98, 1.13) | 1.4E−01 | 0.620 | 0.88 (0.81, 0.96) | 3.4E−03 | 0.625 |
| Cer(d18:1/22:0)/PC 40:8 | 1.12 (1.06, 1.17) | 2.2E−05 | 0.626 | 1.14 (1.07, 1.22) | 1.1E−04 | 0.624 | 0.90 (0.84, 0.97) | 8.0E−03 | 0.623 |
| Cer(d18:2/24:1)/PC 38:7 | 1.12 (1.06, 1.18) | 2.5E−05 | 0.626 | 1.06 (0.98, 1.13) | 1.3E−01 | 0.619 | 0.88 (0.81, 0.96) | 3.4E−03 | 0.625 |
| Cer(d20:1/22:0)/PC 39:4 | 1.14 (1.07, 1.21) | 2.5E−05 | 0.623 | 1.10 (1.03, 1.18) | 4.6E−03 | 0.622 | 0.98 (0.91, 1.05) | 5.7E−01 | 0.619 |
| Cer(d16:1/16:0)/PC 16:0/22:5 | 1.16 (1.08, 1.24) | 2.5E−05 | 0.624 | 1.08 (1.01, 1.16) | 2.6E−02 | 0.620 | 0.93 (0.86, 1.01) | 7.4E−02 | 0.620 |
| Cer(d20:1/24:1)/PC 39:2 | 1.12 (1.06, 1.19) | 2.6E−05 | 0.624 | 1.09 (1.02, 1.16) | 1.3E−02 | 0.622 | 0.98 (0.91, 1.05) | 5.1E−01 | 0.619 |
| Cer(d20:1/22:0)/PC 40:1 | 1.15 (1.08, 1.23) | 2.6E−05 | 0.627 | 1.10 (1.03, 1.18) | 4.6E−03 | 0.622 | 0.98 (0.91, 1.06) | 6.4E−01 | 0.619 |
| Cer(d16:1/16:0)/PC 40:8 | 1.12 (1.06, 1.18) | 3.3E−05 | 0.625 | 1.08 (1.01, 1.16) | 2.6E−02 | 0.620 | 0.90 (0.84, 0.97) | 8.0E−03 | 0.623 |
| Cer(d18:1/22:0)/PC 17:0/18:2 | 1.16 (1.08, 1.24) | 3.6E−05 | 0.626 | 1.14 (1.07, 1.22) | 1.1E−04 | 0.624 | 1.03 (0.95, 1.11) | 4.7E−01 | 0.618 |
| Cer(d18:1/22:0)/PC 17:0/20:3 | 1.15 (1.08, 1.23) | 3.6E−05 | 0.627 | 1.14 (1.07, 1.22) | 1.1E−04 | 0.624 | 0.99 (0.92, 1.07) | 8.5E−01 | 0.620 |
| Cer(d18:1/22:0)/PC 40:1 | 1.14 (1.07, 1.22) | 4.8E−05 | 0.626 | 1.14 (1.07, 1.22) | 1.1E−04 | 0.624 | 0.98 (0.91, 1.06) | 6.4E−01 | 0.619 |
| Cer(d18:1/22:0)/Cer(d18:1/24:0) | 1.14 (1.07, 1.21) | 5.0E−05 | 0.625 | 1.14 (1.07, 1.22) | 1.1E−04 | 0.624 | 1.07 (0.99, 1.15) | 8.5E−02 | 0.619 |
| Cer(d18:1/22:0)/PC 36:0 | 1.14 (1.07, 1.22) | 5.1E−05 | 0.625 | 1.14 (1.07, 1.22) | 1.1E−04 | 0.624 | 1.01 (0.94, 1.08) | 8.7E−01 | 0.618 |
| Cer(d20:1/24:1)/PC 36:5 | 1.14 (1.07, 1.22) | 5.1E−05 | 0.624 | 1.09 (1.02, 1.16) | 1.3E−02 | 0.622 | 0.91 (0.85, 0.99) | 2.3E−02 | 0.620 |
| Cer(d20:1/22:0)/PC 16:0/22:5 | 1.14 (1.07, 1.22) | 5.1E−05 | 0.625 | 1.10 (1.03, 1.18) | 4.6E−03 | 0.622 | 0.93 (0.86, 1.01) | 7.4E−02 | 0.620 |
| Cer(d20:1/24:1)/PC 38:6 | 1.14 (1.07, 1.22) | 5.2E−05 | 0.626 | 1.09 (1.02, 1.16) | 1.3E−02 | 0.622 | 0.92 (0.85, 0.99) | 3.1E−02 | 0.620 |
| Cer(d16:1/16:0)/Cer(d16:1/24:0) | 1.15 (1.07, 1.23) | 5.4E−05 | 0.623 | 1.08 (1.01, 1.16) | 2.6E−02 | 0.620 | 0.96 (0.90, 1.04) | 3.4E−01 | 0.619 |
| Cer(d18:1/22:0)/PC 35:2 | 1.14 (1.07, 1.22) | 6.5E−05 | 0.626 | 1.14 (1.07, 1.22) | 1.1E−04 | 0.624 | 1.01 (0.94, 1.09) | 7.4E−01 | 0.618 |
| Cer(d20:1/22:0)/PC 16:0/22:6 | 1.15 (1.07, 1.23) | 6.8E−05 | 0.625 | 1.10 (1.03, 1.18) | 4.6E−03 | 0.622 | 0.90 (0.84, 0.98) | 9.3E−03 | 0.622 |
| Cer(d20:1/22:0)/PC 39:2 | 1.12 (1.06, 1.18) | 8.1E−05 | 0.623 | 1.10 (1.03, 1.18) | 4.6E−03 | 0.622 | 0.98 (0.91, 1.05) | 5.1E−01 | 0.619 |
| Cer(d18:1/22:0)/PC 38:6 | 1.14 (1.07, 1.22) | 9.5E−05 | 0.624 | 1.14 (1.07, 1.22) | 1.1E−04 | 0.624 | 0.92 (0.85, 0.99) | 3.1E−02 | 0.620 |
| Cer(d18:2/16:0)/PC 16:0/20:5 | 1.14 (1.07, 1.22) | 1.0E−04 | 0.622 | 1.09 (1.01, 1.17) | 1.9E−02 | 0.619 | 0.90 (0.83, 0.97) | 5.1E−03 | 0.621 |

TABLE 2-continued

The p-value of lipid ratios are lower than the corresponding lipids alone.

| | Lipid ratio | | | Denominator lipid | | | Numerator lipid | | |
|---|---|---|---|---|---|---|---|---|---|
| Lipid ratio | HR (95% CI) | p-value | C-stat | HR (95% CI) | p-value | C-stat | HR (95% CI) | p-value | C-stat |
| Cer(d18:2/18:0)/ PC 18:0/20:5 | 1.14 (1.06, 1.22) | 1.3E−04 | 0.622 | 1.06 (0.99, 1.14) | 8.7E−02 | 0.619 | 0.88 (0.81, 0.95) | 9.7E−04 | 0.622 |
| Cer(d18:2/16:0)/ PC 38:5 | 1.12 (1.06, 1.19) | 1.4E−04 | 0.621 | 1.09 (1.01, 1.17) | 1.9E−02 | 0.619 | 0.89 (0.82, 0.96) | 3.5E−03 | 0.621 |
| Cer(d16:1/16:0)/ PC 35:4 | 1.14 (1.06, 1.21) | 1.5E−04 | 0.625 | 1.08 (1.01, 1.16) | 2.6E−02 | 0.620 | 0.95 (0.88, 1.02) | 1.7E−01 | 0.620 |
| Cer(d16:1/18:0)/ PC 18:0/20:5 | 1.14 (1.06, 1.22) | 1.5E−04 | 0.622 | 1.08 (1.01, 1.16) | 3.2E−02 | 0.620 | 0.88 (0.81, 0.95) | 9.7E−04 | 0.622 |
| Cer(d16:1/18:0)/ PC 16:0/22:5 | 1.14 (1.07, 1.22) | 1.5E−04 | 0.624 | 1.08 (1.01, 1.16) | 3.2E−02 | 0.620 | 0.93 (0.86, 1.01) | 7.4E−02 | 0.620 |
| Cer(d20:1/22:0)/ Cer(d18:2/24:0) | 1.13 (1.06, 1.20) | 1.6E−04 | 0.626 | 1.10 (1.03, 1.18) | 4.6E−03 | 0.622 | 0.97 (0.90, 1.05) | 4.5E−01 | 0.620 |
| Cer(d20:1/24:1)/ PC 40:8 | 1.08 (1.04, 1.12) | 1.7E−04 | 0.624 | 1.09 (1.02, 1.16) | 1.3E−02 | 0.622 | 0.90 (0.84, 0.97) | 8.0E−03 | 0.623 |
| Cer(d16:1/18:0)/ PC 16:0/20:5 | 1.14 (1.06, 1.22) | 1.8E−04 | 0.623 | 1.08 (1.01, 1.16) | 3.2E−02 | 0.620 | 0.90 (0.83, 0.97) | 5.1E−03 | 0.621 |
| Cer(d20:1/22:0)/ PC 35:4 | 1.13 (1.06, 1.20) | 1.9E−04 | 0.625 | 1.10 (1.03, 1.18) | 4.6E−03 | 0.622 | 0.95 (0.88, 1.02) | 1.7E−01 | 0.620 |
| Cer(d18:2/18:0)/ PC 38:5 | 1.12 (1.05, 1.18) | 1.9E−04 | 0.622 | 1.06 (0.99, 1.14) | 8.7E−02 | 0.619 | 0.89 (0.82, 0.96) | 3.5E−03 | 0.621 |
| Cer(d16:1/26:0)/ PC 16:0/20:3 | 0.86 (0.79, 0.93) | 2.1E−04 | 0.631 | 0.90 (0.83, 0.98) | 1.0E−02 | 0.629 | 1.11 (1.03, 1.20) | 8.5E−03 | 0.620 |
| Cer(d20:1/22:0)/ PC 18:0/20:5 | 1.13 (1.06, 1.20) | 2.1E−04 | 0.623 | 1.10 (1.03, 1.18) | 4.6E−03 | 0.622 | 0.88 (0.81, 0.95) | 9.7E−04 | 0.622 |
| Cer(d18:2/16:0)/ PC 38:6 | 1.13 (1.06, 1.21) | 2.2E−04 | 0.623 | 1.09 (1.01, 1.17) | 1.9E−02 | 0.619 | 0.92 (0.85, 0.99) | 3.1E−02 | 0.620 |
| Cer(d20:1/24:1)/ PC 16:0/22:5 | 1.13 (1.06, 1.20) | 2.2E−04 | 0.625 | 1.09 (1.02, 1.16) | 1.3E−02 | 0.622 | 0.93 (0.86, 1.01) | 7.4E−02 | 0.620 |
| Cer(d20:1/24:1)/ PC 40:6 | 1.13 (1.06, 1.21) | 2.3E−04 | 0.624 | 1.09 (1.02, 1.16) | 1.3E−02 | 0.622 | 0.95 (0.88, 1.02) | 1.5E−01 | 0.619 |
| Cer(d18:2/18:0)/ PC 16:0/20:5 | 1.13 (1.06, 1.21) | 2.3E−04 | 0.622 | 1.06 (0.99, 1.14) | 8.7E−02 | 0.619 | 0.90 (0.83, 0.97) | 5.1E−03 | 0.621 |
| Cer(d20:1/22:0)/ PC 37:2 | 1.13 (1.06, 1.20) | 2.5E−04 | 0.624 | 1.10 (1.03, 1.18) | 4.6E−03 | 0.622 | 0.99 (0.92, 1.06) | 7.9E−01 | 0.619 |
| Cer(d16:1/18:0)/ PC 38:5 | 1.12 (1.05, 1.19) | 2.6E−04 | 0.622 | 1.08 (1.01, 1.16) | 3.2E−02 | 0.620 | 0.89 (0.82, 0.96) | 3.5E−03 | 0.621 |
| Cer(d20:1/22:0)/ PC 40:8 | 1.09 (1.04, 1.15) | 2.7E−04 | 0.624 | 1.10 (1.03, 1.18) | 4.6E−03 | 0.622 | 0.90 (0.84, 0.97) | 8.0E−03 | 0.623 |
| Cer(d20:1/22:0)/ Cer(d16:1/24:0) | 1.13 (1.06, 1.21) | 2.8E−04 | 0.625 | 1.10 (1.03, 1.18) | 4.6E−03 | 0.622 | 0.96 (0.90, 1.04) | 3.4E−01 | 0.619 |
| Cer(d20:1/22:0)/ PC 38:5 | 1.13 (1.06, 1.20) | 2.9E−04 | 0.623 | 1.10 (1.03, 1.18) | 4.6E−03 | 0.622 | 0.89 (0.82, 0.96) | 3.5E−03 | 0.621 |
| Cer(d20:1/22:0)/ PC 38:6 | 1.14 (1.06, 1.22) | 2.9E−04 | 0.624 | 1.10 (1.03, 1.18) | 4.6E−03 | 0.622 | 0.92 (0.85, 0.99) | 3.1E−02 | 0.620 |
| Cer(d16:1/18:0)/ PC 40:8 | 1.10 (1.05, 1.16) | 3.1E−04 | 0.623 | 1.08 (1.01, 1.16) | 3.2E−02 | 0.620 | 0.90 (0.84, 0.97) | 8.0E−03 | 0.623 |
| Cer(d16:1/26:0)/ Cer(d20:1/24:1) | 0.52 (0.36, 0.74) | 3.2E−04 | 0.633 | 0.90 (0.83, 0.98) | 1.0E−02 | 0.629 | 1.08 (1.00, 1.15) | 4.5E−02 | 0.621 |
| Cer(d20:1/22:0)/ PC 36:0 | 1.13 (1.06, 1.21) | 3.2E−04 | 0.626 | 1.10 (1.03, 1.18) | 4.6E−03 | 0.622 | 1.01 (0.94, 1.08) | 8.7E−01 | 0.618 |
| Cer(d16:1/16:0)/ Cer(d18:2/24:0) | 1.13 (1.06, 1.21) | 3.4E−04 | 0.623 | 1.08 (1.01, 1.16) | 2.6E−02 | 0.620 | 0.97 (0.90, 1.05) | 4.5E−01 | 0.620 |
| Cer(d16:1/26:0)/ PC 16:0/18:2 | 0.86 (0.80, 0.94) | 3.9E−04 | 0.630 | 0.90 (0.83, 0.98) | 1.0E−02 | 0.629 | 1.12 (1.04, 1.20) | 2.7E−03 | 0.619 |
| Cer(d18:2/16:0)/ PC 36:5 | 1.13 (1.06, 1.21) | 4.2E−04 | 0.620 | 1.09 (1.01, 1.17) | 1.9E−02 | 0.619 | 0.91 (0.85, 0.99) | 2.3E−02 | 0.620 |
| Cer(d20:1/24:1)/ PC 39:4 | 1.10 (1.04, 1.16) | 4.4E−04 | 0.622 | 1.09 (1.02, 1.16) | 1.3E−02 | 0.622 | 0.98 (0.91, 1.05) | 5.7E−01 | 0.619 |
| Cer(d18:2/18:0)/ PC 16:0/22:5 | 1.13 (1.06, 1.21) | 4.4E−04 | 0.623 | 1.06 (0.99, 1.14) | 8.7E−02 | 0.619 | 0.93 (0.86, 1.01) | 7.4E−02 | 0.620 |
| Cer(d16:1/18:0)/ PC 39:2 | 1.11 (1.05, 1.17) | 4.5E−04 | 0.622 | 1.08 (1.01, 1.16) | 3.2E−02 | 0.620 | 0.98 (0.91, 1.05) | 5.1E−01 | 0.619 |
| Cer(d16:1/18:0)/ PC 35:4 | 1.13 (1.05, 1.21) | 4.7E−04 | 0.624 | 1.08 (1.01, 1.16) | 3.2E−02 | 0.620 | 0.95 (0.88, 1.02) | 1.7E−01 | 0.620 |
| Cer(d16:1/16:0)/ PC 16:0/20:5 | 1.13 (1.05, 1.21) | 4.7E−04 | 0.621 | 1.08 (1.01, 1.16) | 2.6E−02 | 0.620 | 0.90 (0.83, 0.97) | 5.1E−03 | 0.621 |
| Cer(d16:1/26:0)/ PC 36:3 | 0.86 (0.80, 0.94) | 5.2E−04 | 0.630 | 0.90 (0.83, 0.98) | 1.0E−02 | 0.629 | 1.09 (1.02, 1.18) | 1.7E−02 | 0.620 |
| Cer(d20:1/22:0)/ PC 16:0/20:5 | 1.12 (1.05, 1.19) | 5.3E−04 | 0.622 | 1.10 (1.03, 1.18) | 4.6E−03 | 0.622 | 0.90 (0.83, 0.97) | 5.1E−03 | 0.621 |
| Cer(d16:1/20:0)/ PC 38:5 | 1.12 (1.05, 1.19) | 5.4E−04 | 0.621 | 1.08 (1.00, 1.16) | 4.3E−02 | 0.619 | 0.89 (0.82, 0.96) | 3.5E−03 | 0.621 |
| Cer(d16:1/18:0)/ PC 16:0/22:6 | 1.13 (1.05, 1.21) | 5.5E−04 | 0.623 | 1.08 (1.01, 1.16) | 3.2E−02 | 0.620 | 0.90 (0.84, 0.98) | 9.3E−03 | 0.622 |

TABLE 2-continued

The p-value of lipid ratios are lower than the corresponding lipids alone.

| | Lipid ratio | | | Denominator lipid | | | Numerator lipid | | |
|---|---|---|---|---|---|---|---|---|---|
| Lipid ratio | HR (95% CI) | p-value | C-stat | HR (95% CI) | p-value | C-stat | HR (95% CI) | p-value | C-stat |
| Cer(d18:2/16:0)/ PC 39:2 | 1.11 (1.05, 1.18) | 5.6E−04 | 0.621 | 1.09 (1.01, 1.17) | 1.9E−02 | 0.619 | 0.98 (0.91, 1.05) | 5.1E−01 | 0.619 |
| Cer(d16:1/16:0)/ PC 16:0/22:6 | 1.13 (1.05, 1.21) | 5.7E−04 | 0.623 | 1.08 (1.01, 1.16) | 2.6E−02 | 0.620 | 0.90 (0.84, 0.98) | 9.3E−03 | 0.622 |
| Cer(d18:2/16:0)/ PC 35:4 | 1.12 (1.05, 1.20) | 5.8E−04 | 0.624 | 1.09 (1.01, 1.17) | 1.9E−02 | 0.619 | 0.95 (0.88, 1.02) | 1.7E−01 | 0.620 |
| Cer(d20:1/22:0)/ PC 31:0 | 1.13 (1.05, 1.20) | 5.9E−04 | 0.625 | 1.10 (1.03, 1.18) | 4.6E−03 | 0.622 | 0.99 (0.92, 1.06) | 7.0E−01 | 0.619 |
| Cer(d16:1/16:0)/ PC 34:4 | 1.12 (1.05, 1.19) | 6.2E−04 | 0.623 | 1.08 (1.01, 1.16) | 2.6E−02 | 0.620 | 0.98 (0.91, 1.06) | 6.6E−01 | 0.619 |
| Cer(d20:1/22:0)/ PC 40:5 | 1.12 (1.05, 1.20) | 6.2E−04 | 0.623 | 1.10 (1.03, 1.18) | 4.6E−03 | 0.622 | 0.94 (0.87, 1.01) | 1.1E−01 | 0.620 |
| Cer(d18:2/18:0)/ PC 16:0/22:6 | 1.12 (1.05, 1.20) | 6.2E−04 | 0.623 | 1.06 (0.99, 1.14) | 8.7E−02 | 0.619 | 0.90 (0.84, 0.98) | 9.3E−03 | 0.622 |
| Cer(d16:1/20:0)/ PC 16:0/20:5 | 1.13 (1.05, 1.20) | 6.5E−04 | 0.621 | 1.08 (1.00, 1.16) | 4.3E−02 | 0.619 | 0.90 (0.83, 0.97) | 5.1E−03 | 0.621 |
| Cer(d18:2/16:0)/ Cer(d18:2/24:0) | 1.12 (1.05, 1.20) | 6.8E−04 | 0.622 | 1.09 (1.01, 1.17) | 1.9E−02 | 0.619 | 0.97 (0.90, 1.05) | 4.5E−01 | 0.620 |
| Cer(d16:1/26:0)/ PC 36:4 | 0.87 (0.80, 0.94) | 7.6E−04 | 0.630 | 0.90 (0.83, 0.98) | 1.0E−02 | 0.629 | 1.09 (1.01, 1.17) | 3.3E−02 | 0.620 |
| Cer(d16:1/16:0)/ PC 39:2 | 1.11 (1.04, 1.17) | 8.0E−04 | 0.621 | 1.08 (1.01, 1.16) | 2.6E−02 | 0.620 | 0.98 (0.91, 1.05) | 5.1E−01 | 0.619 |
| Cer(d16:1/26:0)/ PC 16:0/20:4 | 0.87 (0.80, 0.94) | 8.5E−04 | 0.630 | 0.90 (0.83, 0.98) | 1.0E−02 | 0.629 | 1.09 (1.01, 1.18) | 2.3E−02 | 0.620 |
| Cer(d16:1/26:0)/ PC 16:0/18:1 | 0.87 (0.81, 0.95) | 9.1E−04 | 0.630 | 0.90 (0.83, 0.98) | 1.0E−02 | 0.629 | 1.11 (1.04, 1.19) | 2.9E−03 | 0.621 |
| Cer(d20:1/22:0)/ PC 30:2 | 1.10 (1.04, 1.17) | 9.2E−04 | 0.624 | 1.10 (1.03, 1.18) | 4.6E−03 | 0.622 | 0.99 (0.92, 1.06) | 7.9E−01 | 0.619 |
| Cer(d16:1/26:0)/ PC 18:1/18:1 | 0.87 (0.80, 0.95) | 9.2E−04 | 0.630 | 0.90 (0.83, 0.98) | 1.0E−02 | 0.629 | 1.10 (1.04, 1.16) | 1.6E−03 | 0.621 |
| Cer(d20:1/22:0)/ PC 17:0/20:4 | 1.12 (1.05, 1.19) | 9.6E−04 | 0.623 | 1.10 (1.03, 1.18) | 4.6E−03 | 0.622 | 0.99 (0.92, 1.07) | 8.5E−01 | 0.619 |
| Cer(d18:2/24:1)/ PC 40:8 | 1.09 (1.04, 1.15) | 9.8E−04 | 0.623 | 1.06 (0.98, 1.13) | 1.3E−01 | 0.619 | 0.90 (0.84, 0.97) | 8.0E−03 | 0.623 |
| Cer(d18:2/24:1)/ PC 16:0/20:5 | 1.12 (1.05, 1.19) | 9.9E−04 | 0.622 | 1.06 (0.98, 1.13) | 1.3E−01 | 0.619 | 0.90 (0.83, 0.97) | 5.1E−03 | 0.621 |
| Cer(d16:1/16:0)/ PC 31:0 | 1.12 (1.05, 1.19) | 1.1E−03 | 0.624 | 1.08 (1.01, 1.16) | 2.6E−02 | 0.620 | 0.99 (0.92, 1.06) | 7.0E−01 | 0.619 |
| Cer(d18:2/18:0)/ PC 39:2 | 1.10 (1.04, 1.17) | 1.1E−03 | 0.621 | 1.06 (0.99, 1.14) | 8.7E−02 | 0.619 | 0.98 (0.91, 1.05) | 5.1E−01 | 0.619 |
| Cer(d16:1/26:0)/ PC 18:0/18:2 | 0.87 (0.81, 0.95) | 1.1E−03 | 0.629 | 0.90 (0.83, 0.98) | 1.0E−02 | 0.629 | 1.10 (1.02, 1.18) | 1.1E−02 | 0.619 |
| Cer(d20:1/22:0)/ PC 37:4 | 1.09 (1.03, 1.14) | 1.2E−03 | 0.622 | 1.10 (1.03, 1.18) | 4.6E−03 | 0.622 | 0.98 (0.91, 1.06) | 6.3E−01 | 0.619 |
| Cer(d16:1/26:0)/ PC 18:0/20:3 | 0.87 (0.80, 0.95) | 1.2E−03 | 0.629 | 0.90 (0.83, 0.98) | 1.0E−02 | 0.629 | 1.09 (1.01, 1.17) | 3.5E−02 | 0.619 |
| Cer(d16:1/20:0)/ PC 16:0/22:5 | 1.12 (1.05, 1.20) | 1.2E−03 | 0.621 | 1.08 (1.00, 1.16) | 4.3E−02 | 0.619 | 0.93 (0.86, 1.01) | 7.4E−02 | 0.620 |
| Cer(d20:1/22:0)/ PC 17:0/20:3 | 1.11 (1.04, 1.17) | 1.2E−03 | 0.625 | 1.10 (1.03, 1.18) | 4.6E−03 | 0.622 | 0.99 (0.92, 1.07) | 8.5E−01 | 0.620 |
| Cer(d16:1/26:0)/ Cer(d18:1/24:0) | 0.87 (0.81, 0.95) | 1.2E−03 | 0.630 | 0.90 (0.83, 0.98) | 1.0E−02 | 0.629 | 1.07 (0.99, 1.15) | 8.5E−02 | 0.619 |
| Cer(d20:1/24:1)/ PC 31:0 | 1.11 (1.04, 1.19) | 1.3E−03 | 0.625 | 1.09 (1.02, 1.16) | 1.3E−02 | 0.622 | 0.99 (0.92, 1.06) | 7.0E−01 | 0.619 |
| Cer(d18:2/18:0)/ PC 36:5 | 1.12 (1.04, 1.20) | 1.4E−03 | 0.621 | 1.06 (0.99, 1.14) | 8.7E−02 | 0.619 | 0.91 (0.85, 0.99) | 2.3E−02 | 0.620 |
| Cer(d18:2/24:1)/ PC 38:5 | 1.10 (1.04, 1.17) | 1.4E−03 | 0.621 | 1.06 (0.98, 1.13) | 1.3E−01 | 0.619 | 0.89 (0.82, 0.96) | 3.5E−03 | 0.621 |
| Cer(d18:2/16:0)/ PC 40:5 | 1.12 (1.04, 1.20) | 1.4E−03 | 0.621 | 1.09 (1.01, 1.17) | 1.9E−02 | 0.619 | 0.94 (0.87, 1.01) | 1.1E−01 | 0.620 |
| Cer(d16:1/18:0)/ PC 31:0 | 1.11 (1.04, 1.19) | 1.5E−03 | 0.623 | 1.08 (1.01, 1.16) | 3.2E−02 | 0.620 | 0.99 (0.92, 1.06) | 7.0E−01 | 0.619 |
| Cer(d20:1/22:0)/ PC 35:2 | 1.11 (1.04, 1.19) | 1.5E−03 | 0.624 | 1.10 (1.03, 1.18) | 4.6E−03 | 0.622 | 1.01 (0.94, 1.09) | 7.4E−01 | 0.618 |
| Cer(d16:1/16:0)/ PC 37:4 | 1.09 (1.03, 1.14) | 1.5E−03 | 0.621 | 1.08 (1.01, 1.16) | 2.6E−02 | 0.620 | 0.98 (0.91, 1.06) | 6.3E−01 | 0.619 |
| Cer(d16:1/26:0)/ PC 38:4 | 0.87 (0.80, 0.95) | 1.5E−03 | 0.630 | 0.90 (0.83, 0.98) | 1.0E−02 | 0.629 | 1.07 (0.99, 1.15) | 7.4E−02 | 0.619 |
| Cer(d20:1/24:1)/ PC 40:1 | 1.11 (1.04, 1.18) | 1.5E−03 | 0.625 | 1.09 (1.02, 1.16) | 1.3E−02 | 0.622 | 0.98 (0.91, 1.06) | 6.4E−01 | 0.619 |
| Cer(d16:1/16:0)/ PC 40:5 | 1.12 (1.04, 1.20) | 1.5E−03 | 0.621 | 1.08 (1.01, 1.16) | 2.6E−02 | 0.620 | 0.94 (0.87, 1.01) | 1.1E−01 | 0.620 |
| Cer(d20:1/22:0)/ PC 17:0/18:2 | 1.12 (1.04, 1.20) | 1.5E−03 | 0.624 | 1.10 (1.03, 1.18) | 4.6E−03 | 0.622 | 1.03 (0.95, 1.11) | 4.7E−01 | 0.618 |

TABLE 2-continued

The p-value of lipid ratios are lower than the corresponding lipids alone.

| Lipid ratio | Lipid ratio | | | Denominator lipid | | | Numerator lipid | | |
|---|---|---|---|---|---|---|---|---|---|
| | HR (95% CI) | p-value | C-stat | HR (95% CI) | p-value | C-stat | HR (95% CI) | p-value | C-stat |
| Cer(d20:1/24:1)/ PC 40:3 | 1.10 (1.04, 1.17) | 1.6E−03 | 0.623 | 1.09 (1.02, 1.16) | 1.3E−02 | 0.622 | 0.94 (0.87, 1.01) | 7.2E−02 | 0.620 |
| Cer(d16:1/16:0)/ PC 35:0 | 1.09 (1.03, 1.15) | 1.8E−03 | 0.624 | 1.08 (1.01, 1.16) | 2.6E−02 | 0.620 | 0.96 (0.89, 1.04) | 2.9E−01 | 0.620 |
| Cer(d16:1/18:0)/ PC 36:5 | 1.12 (1.04, 1.20) | 1.8E−03 | 0.620 | 1.08 (1.01, 1.16) | 3.2E−02 | 0.620 | 0.91 (0.85, 0.99) | 2.3E−02 | 0.620 |
| Cer(d20:1/23:0)/ PC 38:5 | 1.11 (1.04, 1.19) | 1.8E−03 | 0.621 | 1.05 (0.98, 1.13) | 1.4E−01 | 0.620 | 0.89 (0.82, 0.96) | 3.5E−03 | 0.621 |
| Cer(d16:1/26:0)/ PC 34:1 | 0.88 (0.81, 0.95) | 1.9E−03 | 0.629 | 0.90 (0.83, 0.98) | 1.0E−02 | 0.629 | 1.10 (1.02, 1.18) | 8.9E−03 | 0.620 |
| Cer(d16:1/16:0)/ PC 36:5 | 1.11 (1.04, 1.19) | 2.0E−03 | 0.620 | 1.08 (1.01, 1.16) | 2.6E−02 | 0.620 | 0.91 (0.85, 0.99) | 2.3E−02 | 0.620 |
| Cer(d20:1/24:1)/ PC 40:5 | 1.10 (1.04, 1.17) | 2.0E−03 | 0.623 | 1.09 (1.02, 1.16) | 1.3E−02 | 0.622 | 0.94 (0.87, 1.01) | 1.1E−01 | 0.620 |
| Cer(d16:1/18:0)/ PC 40:5 | 1.11 (1.04, 1.19) | 2.1E−03 | 0.621 | 1.08 (1.01, 1.16) | 3.2E−02 | 0.620 | 0.94 (0.87, 1.01) | 1.1E−01 | 0.620 |
| Cer(d18:2/24:1)/ PC 16:0/22:6 | 1.11 (1.04, 1.18) | 2.1E−03 | 0.623 | 1.06 (0.98, 1.13) | 1.3E−01 | 0.619 | 0.90 (0.84, 0.98) | 9.3E−03 | 0.622 |
| Cer(d16:1/20:0)/ PC 36:5 | 1.11 (1.04, 1.19) | 2.3E−03 | 0.620 | 1.08 (1.00, 1.16) | 4.3E−02 | 0.619 | 0.91 (0.85, 0.99) | 2.3E−02 | 0.620 |
| Cer(d16:1/16:0)/ PC 38:6 | 1.11 (1.04, 1.19) | 2.3E−03 | 0.622 | 1.08 (1.01, 1.16) | 2.6E−02 | 0.620 | 0.92 (0.85, 0.99) | 3.1E−02 | 0.620 |
| Cer(d20:1/23:0)/ PC 16:0/20:5 | 1.11 (1.04, 1.18) | 2.4E−03 | 0.621 | 1.05 (0.98, 1.13) | 1.4E−01 | 0.620 | 0.90 (0.83, 0.97) | 5.1E−03 | 0.621 |
| Cer(d16:1/20:0)/ PC 35:4 | 1.11 (1.04, 1.18) | 2.6E−03 | 0.623 | 1.08 (1.00, 1.16) | 4.3E−02 | 0.619 | 0.95 (0.88, 1.02) | 1.7E−01 | 0.620 |
| Cer(d18:2/24:1)/ PC 39:2 | 1.10 (1.03, 1.17) | 2.8E−03 | 0.621 | 1.06 (0.98, 1.13) | 1.3E−01 | 0.619 | 0.98 (0.91, 1.05) | 5.1E−01 | 0.619 |
| Cer(d16:1/26:0)/ PC 18:0/18:1 | 0.89 (0.82, 0.96) | 2.8E−03 | 0.629 | 0.90 (0.83, 0.98) | 1.0E−02 | 0.629 | 1.07 (1.00, 1.14) | 5.0E−02 | 0.619 |
| Cer(d20:1/24:1)/ PC 37:4 | 1.10 (1.03, 1.16) | 2.9E−03 | 0.622 | 1.09 (1.02, 1.16) | 1.3E−02 | 0.622 | 0.98 (0.91, 1.06) | 6.3E−01 | 0.619 |
| Cer(d20:1/23:0)/ PC 16:0/22:6 | 1.11 (1.04, 1.19) | 2.9E−03 | 0.622 | 1.05 (0.98, 1.13) | 1.4E−01 | 0.620 | 0.90 (0.84, 0.98) | 9.3E−03 | 0.622 |
| Cer(d18:2/16:0)/ PC 31:0 | 1.11 (1.04, 1.19) | 3.0E−03 | 0.623 | 1.09 (1.01, 1.17) | 1.9E−02 | 0.619 | 0.99 (0.92, 1.06) | 7.0E−01 | 0.619 |
| Cer(d20:1/22:0)/ PC 34:4 | 1.08 (1.03, 1.13) | 3.1E−03 | 0.623 | 1.10 (1.03, 1.18) | 4.6E−03 | 0.622 | 0.98 (0.91, 1.06) | 6.6E−01 | 0.619 |
| Cer(d20:1/23:0)/ PC 39:2 | 1.10 (1.03, 1.17) | 3.1E−03 | 0.621 | 1.05 (0.98, 1.13) | 1.4E−01 | 0.620 | 0.98 (0.91, 1.05) | 5.1E−01 | 0.619 |
| Cer(d16:1/26:0)/ PC 18:0/20:4 | 0.88 (0.82, 0.96) | 3.1E−03 | 0.629 | 0.90 (0.83, 0.98) | 1.0E−02 | 0.629 | 1.08 (1.00, 1.16) | 6.2E−02 | 0.619 |
| Cer(d20:1/24:1)/ PC 35:4 | 1.10 (1.03, 1.18) | 3.4E−03 | 0.623 | 1.09 (1.02, 1.16) | 1.3E−02 | 0.622 | 0.95 (0.88, 1.02) | 1.7E−01 | 0.620 |
| Cer(d20:1/23:0)/ PC 16:0/22:5 | 1.11 (1.03, 1.18) | 3.4E−03 | 0.622 | 1.05 (0.98, 1.13) | 1.4E−01 | 0.620 | 0.93 (0.86, 1.01) | 7.4E−02 | 0.620 |
| Cer(d16:1/18:0)/ PC 38:6 | 1.11 (1.03, 1.19) | 3.5E−03 | 0.622 | 1.08 (1.01, 1.16) | 3.2E−02 | 0.620 | 0.92 (0.85, 0.99) | 3.1E−02 | 0.620 |
| Cer(d16:1/20:0)/ PC 31:0 | 1.11 (1.03, 1.19) | 3.6E−03 | 0.622 | 1.08 (1.00, 1.16) | 4.3E−02 | 0.619 | 0.99 (0.92, 1.06) | 7.0E−01 | 0.619 |
| Cer(d18:1/23:0)/ PC 36:5 | 1.11 (1.03, 1.19) | 3.6E−03 | 0.620 | 1.04 (0.97, 1.11) | 3.3E−01 | 0.619 | 0.91 (0.85, 0.99) | 2.3E−02 | 0.620 |
| Cer(d18:2/18:0)/ PC 38:6 | 1.10 (1.03, 1.18) | 3.7E−03 | 0.622 | 1.06 (0.99, 1.14) | 8.7E−02 | 0.619 | 0.92 (0.85, 0.99) | 3.1E−02 | 0.620 |
| Cer(d18:2/24:1)/ PC 16:0/22:5 | 1.10 (1.03, 1.18) | 3.7E−03 | 0.622 | 1.06 (0.98, 1.13) | 1.3E−01 | 0.619 | 0.93 (0.86, 1.01) | 7.4E−02 | 0.620 |
| Cer(d16:1/20:0)/ PC 39:2 | 1.09 (1.03, 1.16) | 3.8E−03 | 0.620 | 1.08 (1.00, 1.16) | 4.3E−02 | 0.619 | 0.98 (0.91, 1.05) | 5.1E−01 | 0.619 |
| Cer(d18:2/16:0)/ PC 37:4 | 1.07 (1.02, 1.12) | 4.0E−03 | 0.621 | 1.09 (1.01, 1.17) | 1.9E−02 | 0.619 | 0.98 (0.91, 1.06) | 6.3E−01 | 0.619 |
| Cer(d20:1/22:0)/ PC 14:0/18:2 | 1.09 (1.03, 1.16) | 4.1E−03 | 0.624 | 1.10 (1.03, 1.18) | 4.6E−03 | 0.622 | 1.00 (0.93, 1.08) | 9.5E−01 | 0.619 |
| Cer(d20:1/22:0)/ PC 17:0/18:1 | 1.10 (1.03, 1.18) | 4.2E−03 | 0.623 | 1.10 (1.03, 1.18) | 4.6E−03 | 0.622 | 1.00 (0.93, 1.08) | 9.7E−01 | 0.619 |
| Cer(d18:1/26:1)/ PC 16:0/18:3 | 0.89 (0.82, 0.96) | 4.4E−03 | 0.619 | 0.96 (0.89, 1.03) | 2.9E−01 | 0.619 | 1.07 (1.01, 1.15) | 3.3E−02 | 0.619 |
| Cer(d20:1/24:1)/ PC 37:2 | 1.09 (1.03, 1.17) | 5.0E−03 | 0.622 | 1.09 (1.02, 1.16) | 1.3E−02 | 0.622 | 0.99 (0.92, 1.06) | 7.9E−01 | 0.619 |
| Cer(d16:1/18:0)/ PC 37:4 | 1.09 (1.03, 1.15) | 5.1E−03 | 0.621 | 1.08 (1.01, 1.16) | 3.2E−02 | 0.620 | 0.98 (0.91, 1.06) | 6.3E−01 | 0.619 |
| Cer(d20:1/24:1)/ PC 38:1 | 1.09 (1.03, 1.17) | 5.1E−03 | 0.623 | 1.09 (1.02, 1.16) | 1.3E−02 | 0.622 | 0.99 (0.92, 1.06) | 7.8E−01 | 0.619 |
| Cer(d18:2/18:0)/ PC 35:4 | 1.10 (1.03, 1.17) | 5.2E−03 | 0.623 | 1.06 (0.99, 1.14) | 8.7E−02 | 0.619 | 0.95 (0.88, 1.02) | 1.7E−01 | 0.620 |

TABLE 2-continued

The p-value of lipid ratios are lower than the corresponding lipids alone.

| | Lipid ratio | | | Denominator lipid | | | Numerator lipid | | |
|---|---|---|---|---|---|---|---|---|---|
| Lipid ratio | HR (95% CI) | p-value | C-stat | HR (95% CI) | p-value | C-stat | HR (95% CI) | p-value | C-stat |
| Cer(d18:1/26:1)/ PC 34:1 | 0.90 (0.83, 0.97) | 5.4E−03 | 0.620 | 0.96 (0.89, 1.03) | 2.9E−01 | 0.619 | 1.10 (1.02, 1.18) | 8.9E−03 | 0.620 |
| Cer(d20:1/23:0)/ PC 38:6 | 1.11 (1.03, 1.19) | 5.4E−03 | 0.622 | 1.05 (0.98, 1.13) | 1.4E−01 | 0.620 | 0.92 (0.85, 0.99) | 3.1E−02 | 0.620 |
| Cer(d18:2/24:1)/ PC 37:2 | 1.10 (1.03, 1.18) | 5.6E−03 | 0.621 | 1.06 (0.98, 1.13) | 1.3E−01 | 0.619 | 0.99 (0.92, 1.06) | 7.9E−01 | 0.619 |
| Cer(d16:1/18:0)/ PC 35:0 | 1.08 (1.02, 1.14) | 5.7E−03 | 0.622 | 1.08 (1.01, 1.16) | 3.2E−02 | 0.620 | 0.96 (0.89, 1.04) | 2.9E−01 | 0.620 |
| Cer(d20:1/23:0)/ PC 39:4 | 1.09 (1.02, 1.16) | 6.0E−03 | 0.621 | 1.05 (0.98, 1.13) | 1.4E−01 | 0.620 | 0.98 (0.91, 1.05) | 5.7E−01 | 0.619 |
| Cer(d18:2/16:0)/ PC 34:4 | 1.09 (1.03, 1.16) | 6.1E−03 | 0.622 | 1.09 (1.01, 1.17) | 1.9E−02 | 0.619 | 0.98 (0.91, 1.06) | 6.6E−01 | 0.619 |
| Cer(d18:2/16:0)/ PC 39:4 | 1.08 (1.02, 1.15) | 6.1E−03 | 0.621 | 1.09 (1.01, 1.17) | 1.9E−02 | 0.619 | 0.98 (0.91, 1.05) | 5.7E−01 | 0.619 |
| Cer(d16:1/20:0)/ Cer(d18:2/24:0) | 1.10 (1.03, 1.18) | 6.1E−03 | 0.621 | 1.08 (1.00, 1.16) | 4.3E−02 | 0.619 | 0.97 (0.90, 1.05) | 4.5E−01 | 0.620 |
| Cer(d16:1/16:0)/ PC 35:2 | 1.10 (1.03, 1.17) | 6.2E−03 | 0.622 | 1.08 (1.01, 1.16) | 2.6E−02 | 0.620 | 1.01 (0.94, 1.09) | 7.4E−01 | 0.618 |
| Cer(d16:1/18:0)/ Cer(d16:1/24:0) | 1.10 (1.03, 1.18) | 6.2E−03 | 0.622 | 1.08 (1.01, 1.16) | 3.2E−02 | 0.620 | 0.96 (0.90, 1.04) | 3.4E−01 | 0.619 |
| Cer(d16:1/20:0)/ PC 35:0 | 1.09 (1.02, 1.16) | 6.4E−03 | 0.622 | 1.08 (1.00, 1.16) | 4.3E−02 | 0.619 | 0.96 (0.89, 1.04) | 2.9E−01 | 0.620 |
| Cer(d18:1/23:0)/ PC 16:0/22:5 | 1.10 (1.03, 1.18) | 6.6E−03 | 0.620 | 1.04 (0.97, 1.11) | 3.3E−01 | 0.619 | 0.93 (0.86, 1.01) | 7.4E−02 | 0.620 |
| Cer(d20:1/24:1)/ PC 17:0/20:4 | 1.10 (1.03, 1.18) | 6.7E−03 | 0.622 | 1.09 (1.02, 1.16) | 1.3E−02 | 0.622 | 0.99 (0.92, 1.07) | 8.5E−01 | 0.619 |
| Cer(d18:2/16:0)/ PC 35:0 | 1.08 (1.02, 1.15) | 6.9E−03 | 0.622 | 1.09 (1.01, 1.17) | 1.9E−02 | 0.619 | 0.96 (0.89, 1.04) | 2.9E−01 | 0.620 |
| Cer(d16:1/26:0)/ PC 40:5 | 0.89 (0.82, 0.97) | 6.9E−03 | 0.629 | 0.90 (0.83, 0.98) | 1.0E−02 | 0.629 | 1.09 (1.01, 1.18) | 3.0E−02 | 0.620 |
| Cer(d18:2/16:0)/ PC 17:0/20:4 | 1.10 (1.03, 1.18) | 7.0E−03 | 0.620 | 1.09 (1.01, 1.17) | 1.9E−02 | 0.619 | 0.99 (0.92, 1.07) | 8.5E−01 | 0.619 |
| Cer(d20:1/23:0)/ PC 40:1 | 1.09 (1.02, 1.17) | 7.1E−03 | 0.622 | 1.05 (0.98, 1.13) | 1.4E−01 | 0.620 | 0.98 (0.91, 1.06) | 6.4E−01 | 0.619 |
| Cer(d18:2/16:0)/ PC 37:2 | 1.09 (1.02, 1.15) | 7.2E−03 | 0.621 | 1.09 (1.01, 1.17) | 1.9E−02 | 0.619 | 0.99 (0.92, 1.06) | 7.9E−01 | 0.619 |
| Cer(d16:1/18:0)/ Cer(d18:2/24:0) | 1.10 (1.03, 1.18) | 7.3E−03 | 0.622 | 1.08 (1.01, 1.16) | 3.2E−02 | 0.620 | 0.97 (0.90, 1.05) | 4.5E−01 | 0.620 |
| Cer(d20:1/23:0)/ PC 35:4 | 1.09 (1.02, 1.16) | 7.4E−03 | 0.622 | 1.05 (0.98, 1.13) | 1.4E−01 | 0.620 | 0.95 (0.88, 1.02) | 1.7E−01 | 0.620 |
| Cer(d16:1/20:0)/ PC 40:5 | 1.10 (1.03, 1.18) | 7.4E−03 | 0.620 | 1.08 (1.00, 1.16) | 4.3E−02 | 0.619 | 0.94 (0.87, 1.01) | 1.1E−01 | 0.620 |
| Cer(d18:2/16:0)/ Cer(d16:1/24:0) | 1.10 (1.03, 1.18) | 7.5E−03 | 0.620 | 1.09 (1.01, 1.17) | 1.9E−02 | 0.619 | 0.96 (0.90, 1.04) | 3.4E−01 | 0.619 |
| Cer(d20:1/23:0)/ PC 36:5 | 1.10 (1.03, 1.18) | 7.6E−03 | 0.620 | 1.05 (0.98, 1.13) | 1.4E−01 | 0.620 | 0.91 (0.85, 0.99) | 2.3E−02 | 0.620 |
| Cer(d16:1/18:0)/ PC 39:4 | 1.08 (1.02, 1.15) | 7.6E−03 | 0.621 | 1.08 (1.01, 1.16) | 3.2E−02 | 0.620 | 0.98 (0.91, 1.05) | 5.7E−01 | 0.619 |
| Cer(d16:1/16:0)/ PC 17:0/20:3 | 1.10 (1.02, 1.17) | 7.8E−03 | 0.623 | 1.08 (1.01, 1.16) | 2.6E−02 | 0.620 | 0.99 (0.92, 1.07) | 8.5E−01 | 0.620 |
| Cer(d16:1/18:0)/ PC 37:2 | 1.09 (1.02, 1.16) | 8.0E−03 | 0.621 | 1.08 (1.01, 1.16) | 3.2E−02 | 0.620 | 0.99 (0.92, 1.06) | 7.9E−01 | 0.619 |
| Cer(d16:1/16:0)/ PC 37:2 | 1.08 (1.02, 1.15) | 8.4E−03 | 0.622 | 1.08 (1.01, 1.16) | 2.6E−02 | 0.620 | 0.99 (0.92, 1.06) | 7.9E−01 | 0.619 |
| Cer(d16:1/16:0)/ PC 33:2 | 1.09 (1.02, 1.16) | 8.5E−03 | 0.623 | 1.08 (1.01, 1.16) | 2.6E−02 | 0.620 | 1.00 (0.93, 1.08) | 1.0E+00 | 0.619 |
| Cer(d16:1/20:0)/ PC 37:4 | 1.07 (1.02, 1.13) | 8.6E−03 | 0.620 | 1.08 (1.00, 1.16) | 4.3E−02 | 0.619 | 0.98 (0.91, 1.06) | 6.3E−01 | 0.619 |
| Cer(d18:1/23:0)/ PC 39:2 | 1.09 (1.02, 1.16) | 8.8E−03 | 0.620 | 1.04 (0.97, 1.11) | 3.3E−01 | 0.619 | 0.98 (0.91, 1.05) | 5.1E−01 | 0.619 |
| Cer(d18:2/16:0)/ PC 35:2 | 1.09 (1.02, 1.16) | 8.9E−03 | 0.621 | 1.09 (1.01, 1.17) | 1.9E−02 | 0.619 | 1.01 (0.94, 1.09) | 7.4E−01 | 0.618 |
| Cer(d18:2/24:1)/ PC 36:5 | 1.09 (1.02, 1.16) | 8.9E−03 | 0.620 | 1.06 (0.98, 1.13) | 1.3E−01 | 0.619 | 0.91 (0.85, 0.99) | 2.3E−02 | 0.620 |
| Cer(d18:1/26:1)/ PC 36:3 | 0.90 (0.83, 0.97) | 9.1E−03 | 0.620 | 0.96 (0.89, 1.03) | 2.9E−01 | 0.619 | 1.09 (1.02, 1.18) | 1.7E−02 | 0.620 |
| Cer(d18:2/16:0)/ PC 36:0 | 1.10 (1.02, 1.18) | 9.3E−03 | 0.621 | 1.09 (1.01, 1.17) | 1.9E−02 | 0.619 | 1.01 (0.94, 1.08) | 8.7E−01 | 0.618 |
| Cer(d16:1/20:0)/ PC 35:2 | 1.09 (1.02, 1.17) | 9.7E−03 | 0.621 | 1.08 (1.00, 1.16) | 4.3E−02 | 0.619 | 1.01 (0.94, 1.09) | 7.4E−01 | 0.618 |
| Cer(d16:1/18:0)/ PC 35:2 | 1.09 (1.02, 1.17) | 9.8E−03 | 0.621 | 1.08 (1.01, 1.16) | 3.2E−02 | 0.620 | 1.01 (0.94, 1.09) | 7.4E−01 | 0.618 |
| Cer(d18:2/24:1)/ PC 38:6 | 1.09 (1.02, 1.16) | 9.8E−03 | 0.622 | 1.06 (0.98, 1.13) | 1.3E−01 | 0.619 | 0.92 (0.85, 0.99) | 3.1E−02 | 0.620 |

TABLE 2-continued

The p-value of lipid ratios are lower than the corresponding lipids alone.

| Lipid ratio | Lipid ratio | | | Denominator lipid | | | Numerator lipid | | |
|---|---|---|---|---|---|---|---|---|---|
| | HR (95% CI) | p-value | C-stat | HR (95% CI) | p-value | C-stat | HR (95% CI) | p-value | C-stat |
| Cer(d18:1/26:1)/ PC 18:0/18:1 | 0.91 (0.84, 0.98) | 9.8E−03 | 0.620 | 0.96 (0.89, 1.03) | 2.9E−01 | 0.619 | 1.07 (1.00, 1.14) | 5.0E−02 | 0.619 |
| Cer(d18:2/18:0)/ PC 31:0 | 1.10 (1.02, 1.17) | 1.0E−02 | 0.622 | 1.06 (0.99, 1.14) | 8.7E−02 | 0.619 | 0.99 (0.92, 1.06) | 7.0E−01 | 0.619 |
| Cer(d20:1/24:1)/ PC 36:0 | 1.09 (1.02, 1.16) | 1.0E−02 | 0.623 | 1.09 (1.02, 1.16) | 1.3E−02 | 0.622 | 1.01 (0.94, 1.08) | 8.7E−01 | 0.618 |
| Cer(d16:1/16:0)/ PC 39:4 | 1.08 (1.02, 1.14) | 1.0E−02 | 0.621 | 1.08 (1.01, 1.16) | 2.6E−02 | 0.620 | 0.98 (0.91, 1.05) | 5.7E−01 | 0.619 |
| Cer(d18:2/18:0)/ PC 40:5 | 1.09 (1.02, 1.17) | 1.0E−02 | 0.621 | 1.06 (0.99, 1.14) | 8.7E−02 | 0.619 | 0.94 (0.87, 1.01) | 1.1E−01 | 0.620 |
| Cer(d16:1/16:0)/ PC 17:0/20:4 | 1.09 (1.02, 1.17) | 1.0E−02 | 0.620 | 1.08 (1.01, 1.16) | 2.6E−02 | 0.620 | 0.99 (0.92, 1.07) | 8.5E−01 | 0.619 |
| Cer(d16:1/18:0)/ PC 17:0/20:4 | 1.10 (1.02, 1.17) | 1.0E−02 | 0.620 | 1.08 (1.01, 1.16) | 3.2E−02 | 0.620 | 0.99 (0.92, 1.07) | 8.5E−01 | 0.619 |
| Cer(d18:1/26:1)/ PC 34:2 | 0.90 (0.83, 0.98) | 1.1E−02 | 0.620 | 0.96 (0.89, 1.03) | 2.9E−01 | 0.619 | 1.08 (1.00, 1.16) | 4.8E−02 | 0.619 |
| Cer(d18:2/24:1)/ PC 35:4 | 1.09 (1.02, 1.17) | 1.1E−02 | 0.623 | 1.06 (0.98, 1.13) | 1.3E−01 | 0.619 | 0.95 (0.88, 1.02) | 1.7E−01 | 0.620 |
| Cer(d18:1/26:1)/ PC 36:4 | 0.91 (0.84, 0.98) | 1.1E−02 | 0.620 | 0.96 (0.89, 1.03) | 2.9E−01 | 0.619 | 1.09 (1.01, 1.17) | 3.3E−02 | 0.620 |
| Cer(d16:1/20:0)/ PC 17:0/20:3 | 1.09 (1.02, 1.17) | 1.1E−02 | 0.622 | 1.08 (1.00, 1.16) | 4.3E−02 | 0.619 | 0.99 (0.92, 1.07) | 8.5E−01 | 0.620 |
| Cer(d20:1/23:0)/ PC 31:0 | 1.09 (1.02, 1.17) | 1.2E−02 | 0.622 | 1.05 (0.98, 1.13) | 1.4E−01 | 0.620 | 0.99 (0.92, 1.06) | 7.0E−01 | 0.619 |
| Cer(d18:1/26:0)/ PC 39:2 | 1.08 (1.02, 1.15) | 1.3E−02 | 0.619 | 1.01 (0.94, 1.08) | 8.1E−01 | 0.618 | 0.98 (0.91, 1.05) | 5.1E−01 | 0.619 |
| Cer(d16:1/18:0)/ PC 17:0/20:3 | 1.09 (1.02, 1.17) | 1.3E−02 | 0.623 | 1.08 (1.01, 1.16) | 3.2E−02 | 0.620 | 0.99 (0.92, 1.07) | 8.5E−01 | 0.620 |
| Cer(d16:1/20:0)/ Cer(d16:1/24:0) | 1.09 (1.02, 1.17) | 1.3E−02 | 0.620 | 1.08 (1.00, 1.16) | 4.3E−02 | 0.619 | 0.96 (0.90, 1.04) | 3.4E−01 | 0.619 |
| Cer(d16:1/16:0)/ PC 32:2 | 1.09 (1.02, 1.16) | 1.4E−02 | 0.622 | 1.08 (1.01, 1.16) | 2.6E−02 | 0.620 | 0.99 (0.92, 1.07) | 8.8E−01 | 0.619 |
| Cer(d18:1/26:0)/ PC 37:4 | 1.08 (1.01, 1.14) | 1.4E−02 | 0.620 | 1.01 (0.94, 1.08) | 8.1E−01 | 0.618 | 0.98 (0.91, 1.06) | 6.3E−01 | 0.619 |
| Cer(d18:2/24:1)/ PC 39:4 | 1.08 (1.02, 1.14) | 1.4E−02 | 0.621 | 1.06 (0.98, 1.13) | 1.3E−01 | 0.619 | 0.98 (0.91, 1.05) | 5.7E−01 | 0.619 |
| Cer(d18:2/16:0)/ PC 40:6 | 1.09 (1.02, 1.17) | 1.4E−02 | 0.619 | 1.09 (1.01, 1.17) | 1.9E−02 | 0.619 | 0.95 (0.88, 1.02) | 1.5E−01 | 0.619 |
| Cer(d16:1/20:0)/ PC 17:0/20:4 | 1.09 (1.02, 1.17) | 1.4E−02 | 0.620 | 1.08 (1.00, 1.16) | 4.3E−02 | 0.619 | 0.99 (0.92, 1.07) | 8.5E−01 | 0.619 |
| Cer(d16:1/16:0)/ PC 36:0 | 1.09 (1.02, 1.17) | 1.5E−02 | 0.621 | 1.08 (1.01, 1.16) | 2.6E−02 | 0.620 | 1.01 (0.94, 1.08) | 8.7E−01 | 0.618 |
| Cer(d18:2/18:0)/ PC 37:2 | 1.08 (1.02, 1.16) | 1.5E−02 | 0.621 | 1.06 (0.99, 1.14) | 8.7E−02 | 0.619 | 0.99 (0.92, 1.06) | 7.9E−01 | 0.619 |
| Cer(d16:1/22:0)/ Cer(d16:1/24:0) | 1.09 (1.02, 1.17) | 1.5E−02 | 0.620 | 1.02 (0.95, 1.10) | 5.6E−01 | 0.619 | 0.96 (0.90, 1.04) | 3.4E−01 | 0.619 |
| Cer(d18:1/26:1)/ PC 34:3 | 0.90 (0.83, 0.98) | 1.6E−02 | 0.620 | 0.96 (0.89, 1.03) | 2.9E−01 | 0.619 | 1.06 (0.98, 1.13) | 1.3E−01 | 0.619 |
| Cer(d16:1/20:0)/ PC 34:4 | 1.08 (1.02, 1.15) | 1.6E−02 | 0.622 | 1.08 (1.00, 1.16) | 4.3E−02 | 0.619 | 0.98 (0.91, 1.06) | 6.6E−01 | 0.619 |
| Cer(d16:1/18:0)/ PC 34:4 | 1.08 (1.01, 1.15) | 1.6E−02 | 0.622 | 1.08 (1.01, 1.16) | 3.2E−02 | 0.620 | 0.98 (0.91, 1.06) | 6.6E−01 | 0.619 |
| Cer(d18:1/23:0)/ Cer(d18:2/24:0) | 1.09 (1.02, 1.17) | 1.6E−02 | 0.621 | 1.04 (0.97, 1.11) | 3.3E−01 | 0.619 | 0.97 (0.90, 1.05) | 4.5E−01 | 0.620 |
| Cer(d18:2/18:0)/ Cer(d18:2/24:0) | 1.09 (1.02, 1.17) | 1.6E−02 | 0.622 | 1.06 (0.99, 1.14) | 8.7E−02 | 0.619 | 0.97 (0.90, 1.05) | 4.5E−01 | 0.620 |
| Cer(d20:1/23:0)/ PC 30:2 | 1.08 (1.01, 1.15) | 1.7E−02 | 0.622 | 1.05 (0.98, 1.13) | 1.4E−01 | 0.620 | 0.99 (0.92, 1.06) | 7.9E−01 | 0.619 |
| Cer(d18:1/26:1)/ PC 36:5 | 1.09 (1.01, 1.17) | 1.8E−02 | 0.620 | 0.96 (0.89, 1.03) | 2.9E−01 | 0.619 | 0.91 (0.85, 0.99) | 2.3E−02 | 0.620 |
| Cer(d18:1/26:1)/ Cer(d20:1/24:0) | 0.83 (0.71, 0.97) | 1.9E−02 | 0.622 | 0.96 (0.89, 1.03) | 2.9E−01 | 0.619 | 1.08 (1.00, 1.15) | 4.5E−02 | 0.621 |
| Cer(d16:1/18:0)/ PC 36:0 | 1.09 (1.01, 1.17) | 1.9E−02 | 0.621 | 1.08 (1.01, 1.16) | 3.2E−02 | 0.620 | 1.01 (0.94, 1.08) | 8.7E−01 | 0.618 |
| Cer(d18:2/18:0)/ PC 37:4 | 1.07 (1.01, 1.13) | 1.9E−02 | 0.620 | 1.06 (0.99, 1.14) | 8.7E−02 | 0.619 | 0.98 (0.91, 1.06) | 6.3E−01 | 0.619 |
| Cer(d18:2/18:0)/ PC 39:4 | 1.07 (1.01, 1.13) | 1.9E−02 | 0.620 | 1.06 (0.99, 1.14) | 8.7E−02 | 0.619 | 0.98 (0.91, 1.05) | 5.7E−01 | 0.619 |
| Cer(d16:1/18:0)/ PC 16:1/18:2 | 1.08 (1.01, 1.16) | 1.9E−02 | 0.621 | 1.08 (1.01, 1.16) | 3.2E−02 | 0.620 | 1.03 (0.96, 1.12) | 3.9E−01 | 0.617 |
| Cer(d20:1/23:0)/ PC 40:5 | 1.08 (1.01, 1.16) | 2.0E−02 | 0.621 | 1.05 (0.98, 1.13) | 1.4E−01 | 0.620 | 0.94 (0.87, 1.01) | 1.1E−01 | 0.620 |
| Cer(d16:1/16:0)/ PC 16:1/18:2 | 1.09 (1.01, 1.16) | 2.0E−02 | 0.621 | 1.08 (1.01, 1.16) | 2.6E−02 | 0.620 | 1.03 (0.96, 1.12) | 3.9E−01 | 0.617 |

TABLE 2-continued

The p-value of lipid ratios are lower than the corresponding lipids alone.

| | Lipid ratio | | | Denominator lipid | | | Numerator lipid | | |
|---|---|---|---|---|---|---|---|---|---|
| Lipid ratio | HR (95% CI) | p-value | C-stat | HR (95% CI) | p-value | C-stat | HR (95% CI) | p-value | C-stat |
| Cer(d16:1/16:0)/ PC 14:0/18:1 | 1.09 (1.01, 1.16) | 2.0E−02 | 0.622 | 1.08 (1.01, 1.16) | 2.6E−02 | 0.620 | 1.03 (0.96, 1.11) | 4.2E−01 | 0.618 |
| Cer(d18:1/23:0)/ PC 31:0 | 1.09 (1.01, 1.17) | 2.1E−02 | 0.621 | 1.04 (0.97, 1.11) | 3.3E−01 | 0.619 | 0.99 (0.92, 1.06) | 7.0E−01 | 0.619 |
| Cer(d18:2/18:0)/ PC 17:0/20:4 | 1.08 (1.01, 1.16) | 2.1E−02 | 0.620 | 1.06 (0.99, 1.14) | 8.7E−02 | 0.619 | 0.99 (0.92, 1.07) | 8.5E−01 | 0.619 |
| Cer(d18:2/24:1)/ PC 31:0 | 1.08 (1.01, 1.16) | 2.2E−02 | 0.622 | 1.06 (0.98, 1.13) | 1.3E−01 | 0.619 | 0.99 (0.92, 1.06) | 7.0E−01 | 0.619 |
| Cer(d16:1/16:0)/ PC 14:0/18:2 | 1.08 (1.01, 1.15) | 2.2E−02 | 0.622 | 1.08 (1.01, 1.16) | 2.6E−02 | 0.620 | 1.00 (0.93, 1.08) | 9.5E−01 | 0.619 |
| Cer(d16:1/20:0)/ PC 37:2 | 1.08 (1.01, 1.15) | 2.3E−02 | 0.620 | 1.08 (1.00, 1.16) | 4.3E−02 | 0.619 | 0.99 (0.92, 1.06) | 7.9E−01 | 0.619 |
| Cer(d18:2/18:0)/ PC 35:0 | 1.07 (1.01, 1.14) | 2.4E−02 | 0.621 | 1.06 (0.99, 1.14) | 8.7E−02 | 0.619 | 0.96 (0.89, 1.04) | 2.9E−01 | 0.620 |
| Cer(d16:1/23:0)/ PC 39:2 | 1.07 (1.01, 1.13) | 2.4E−02 | 0.620 | 1.00 (0.93, 1.08) | 9.8E−01 | 0.618 | 0.98 (0.91, 1.05) | 5.1E−01 | 0.619 |
| Cer(d18:2/24:1)/ PC 40:3 | 1.08 (1.01, 1.15) | 2.4E−02 | 0.621 | 1.06 (0.98, 1.13) | 1.3E−01 | 0.619 | 0.94 (0.87, 1.01) | 7.2E−02 | 0.620 |
| Cer(d16:1/20:0)/ PC 14:0/18:1 | 1.08 (1.01, 1.16) | 2.4E−02 | 0.622 | 1.08 (1.00, 1.16) | 4.3E−02 | 0.619 | 1.03 (0.96, 1.11) | 4.2E−01 | 0.618 |
| Cer(d16:1/16:0)/ PC 30:2 | 1.08 (1.01, 1.15) | 2.5E−02 | 0.622 | 1.08 (1.01, 1.16) | 2.6E−02 | 0.620 | 0.99 (0.92, 1.06) | 7.9E−01 | 0.619 |
| Cer(d20:1/23:0)/ Cer(d18:2/24:0) | 1.08 (1.01, 1.15) | 2.5E−02 | 0.622 | 1.05 (0.98, 1.13) | 1.4E−01 | 0.620 | 0.97 (0.90, 1.05) | 4.5E−01 | 0.620 |
| Cer(d16:1/18:0)/ PC 33:2 | 1.08 (1.01, 1.15) | 2.6E−02 | 0.621 | 1.08 (1.01, 1.16) | 3.2E−02 | 0.620 | 1.00 (0.93, 1.08) | 1.0E+00 | 0.619 |
| Cer(d20:1/23:0)/ PC 37:2 | 1.08 (1.01, 1.15) | 2.6E−02 | 0.621 | 1.05 (0.98, 1.13) | 1.4E−01 | 0.620 | 0.99 (0.92, 1.06) | 7.9E−01 | 0.619 |
| Cer(d16:1/20:0)/ PC 33:2 | 1.08 (1.01, 1.15) | 2.7E−02 | 0.621 | 1.08 (1.00, 1.16) | 4.3E−02 | 0.619 | 1.00 (0.93, 1.08) | 1.0E+00 | 0.619 |
| Cer(d18:1/23:0)/ PC 35:4 | 1.08 (1.01, 1.15) | 2.7E−02 | 0.621 | 1.04 (0.97, 1.11) | 3.3E−01 | 0.619 | 0.95 (0.88, 1.02) | 1.7E−01 | 0.620 |
| Cer(d18:1/26:1)/ Cer(d18:1/24:0) | 0.92 (0.85, 0.99) | 2.7E−02 | 0.620 | 0.96 (0.89, 1.03) | 2.9E−01 | 0.619 | 1.07 (0.99, 1.15) | 8.5E−02 | 0.619 |
| Cer(d16:1/20:0)/ PC 36:0 | 1.08 (1.01, 1.16) | 2.8E−02 | 0.620 | 1.08 (1.00, 1.16) | 4.3E−02 | 0.619 | 1.01 (0.94, 1.08) | 8.7E−01 | 0.618 |
| Cer(d16:1/22:0)/ PC 39:2 | 1.07 (1.01, 1.14) | 2.8E−02 | 0.620 | 1.02 (0.95, 1.10) | 5.6E−01 | 0.619 | 0.98 (0.91, 1.05) | 5.1E−01 | 0.619 |
| Cer(d18:1/23:0)/ PC 30:2 | 1.07 (1.01, 1.14) | 2.9E−02 | 0.621 | 1.04 (0.97, 1.11) | 3.3E−01 | 0.619 | 0.99 (0.92, 1.06) | 7.9E−01 | 0.619 |
| Cer(d18:1/26:0)/ PC 30:2 | 1.07 (1.01, 1.13) | 2.9E−02 | 0.621 | 1.01 (0.94, 1.08) | 8.1E−01 | 0.618 | 0.99 (0.92, 1.06) | 7.9E−01 | 0.619 |
| Cer(d16:1/18:0)/ PC 17:0/18:1 | 1.08 (1.01, 1.16) | 3.0E−02 | 0.621 | 1.08 (1.01, 1.16) | 3.2E−02 | 0.620 | 1.00 (0.93, 1.08) | 9.7E−01 | 0.619 |
| Cer(d20:1/23:0)/ Cer(d16:1/24:0) | 1.08 (1.01, 1.15) | 3.0E−02 | 0.621 | 1.05 (0.98, 1.13) | 1.4E−01 | 0.620 | 0.96 (0.90, 1.04) | 3.4E−01 | 0.619 |
| Cer(d18:2/18:0)/ PC 35:2 | 1.08 (1.01, 1.15) | 3.1E−02 | 0.621 | 1.06 (0.99, 1.14) | 8.7E−02 | 0.619 | 1.01 (0.94, 1.09) | 7.4E−01 | 0.618 |
| Cer(d20:1/23:0)/ PC 40:6 | 1.08 (1.01, 1.16) | 3.1E−02 | 0.620 | 1.05 (0.98, 1.13) | 1.4E−01 | 0.620 | 0.95 (0.88, 1.02) | 1.5E−01 | 0.619 |
| Cer(d16:1/20:0)/ PC 17:0/18:2 | 1.08 (1.01, 1.16) | 3.1E−02 | 0.620 | 1.08 (1.00, 1.16) | 4.3E−02 | 0.619 | 1.03 (0.95, 1.11) | 4.7E−01 | 0.618 |
| Cer(d20:1/23:0)/ PC 36:0 | 1.08 (1.01, 1.15) | 3.2E−02 | 0.621 | 1.05 (0.98, 1.13) | 1.4E−01 | 0.620 | 1.01 (0.94, 1.08) | 8.7E−01 | 0.618 |
| Cer(d20:1/23:0)/ PC 39:0 | 1.06 (1.01, 1.13) | 3.2E−02 | 0.621 | 1.05 (0.98, 1.13) | 1.4E−01 | 0.620 | 1.03 (0.97, 1.11) | 3.2E−01 | 0.619 |
| Cer(d18:1/23:0)/ PC 37:4 | 1.07 (1.01, 1.13) | 3.3E−02 | 0.620 | 1.04 (0.97, 1.11) | 3.3E−01 | 0.619 | 0.98 (0.91, 1.06) | 6.3E−01 | 0.619 |
| Cer(d20:1/23:0)/ PC 37:4 | 1.06 (1.01, 1.13) | 3.3E−02 | 0.620 | 1.05 (0.98, 1.13) | 1.4E−01 | 0.620 | 0.98 (0.91, 1.06) | 6.3E−01 | 0.619 |
| Cer(d18:1/26:1)/ PC 38:2 | 0.92 (0.85, 0.99) | 3.3E−02 | 0.619 | 0.96 (0.89, 1.03) | 2.9E−01 | 0.619 | 1.05 (0.98, 1.12) | 2.0E−01 | 0.618 |
| Cer(d16:1/20:0)/ PC 17:0/18:1 | 1.08 (1.01, 1.16) | 3.3E−02 | 0.621 | 1.08 (1.00, 1.16) | 4.3E−02 | 0.619 | 1.00 (0.93, 1.08) | 9.7E−01 | 0.619 |
| Cer(d16:1/20:0)/ PC 16:1/18:2 | 1.08 (1.01, 1.15) | 3.4E−02 | 0.620 | 1.08 (1.00, 1.16) | 4.3E−02 | 0.619 | 1.03 (0.96, 1.12) | 3.9E−01 | 0.617 |
| Cer(d18:1/26:1)/ PC 36:2 | 0.92 (0.85, 0.99) | 3.6E−02 | 0.619 | 0.96 (0.89, 1.03) | 2.9E−01 | 0.619 | 1.06 (0.98, 1.14) | 1.4E−01 | 0.619 |
| Cer(d18:1/23:0)/ PC 37:2 | 1.07 (1.00, 1.14) | 3.8E−02 | 0.620 | 1.04 (0.97, 1.11) | 3.3E−01 | 0.619 | 0.99 (0.92, 1.06) | 7.9E−01 | 0.619 |
| Cer(d18:2/24:1)/ PC 37:4 | 1.05 (1.00, 1.11) | 3.9E−02 | 0.620 | 1.06 (0.98, 1.13) | 1.3E−01 | 0.619 | 0.98 (0.91, 1.06) | 6.3E−01 | 0.619 |
| Cer(d16:1/20:0)/ PC 30:2 | 1.07 (1.00, 1.14) | 4.0E−02 | 0.621 | 1.08 (1.00, 1.16) | 4.3E−02 | 0.619 | 0.99 (0.92, 1.06) | 7.9E−01 | 0.619 |

TABLE 2-continued

The p-value of lipid ratios are lower than the corresponding lipids alone.

| Lipid ratio | Lipid ratio | | | Denominator lipid | | | Numerator lipid | | |
|---|---|---|---|---|---|---|---|---|---|
| | HR (95% CI) | p-value | C-stat | HR (95% CI) | p-value | C-stat | HR (95% CI) | p-value | C-stat |
| Cer(d18:1/26:1)/ PC 33:1 | 0.92 (0.86, 1.00) | 4.1E−02 | 0.619 | 0.96 (0.89, 1.03) | 2.9E−01 | 0.619 | 1.04 (0.97, 1.11) | 3.0E−01 | 0.618 |
| Cer(d18:2/24:1)/ PC 35:0 | 1.07 (1.00, 1.13) | 4.1E−02 | 0.621 | 1.06 (0.98, 1.13) | 1.3E−01 | 0.619 | 0.96 (0.89, 1.04) | 2.9E−01 | 0.620 |
| Cer(d16:1/22:0)/ PC 35:4 | 1.07 (1.00, 1.15) | 4.1E−02 | 0.621 | 1.02 (0.95, 1.10) | 5.6E−01 | 0.619 | 0.95 (0.88, 1.02) | 1.7E−01 | 0.620 |
| Cer(d16:1/22:0)/ PC 30:2 | 1.07 (1.00, 1.14) | 4.2E−02 | 0.621 | 1.02 (0.95, 1.10) | 5.6E−01 | 0.619 | 0.99 (0.92, 1.06) | 7.9E−01 | 0.619 |
| Cer(d18:2/18:0)/ PC 40:6 | 1.07 (1.00, 1.15) | 4.2E−02 | 0.620 | 1.06 (0.99, 1.14) | 8.7E−02 | 0.619 | 0.95 (0.88, 1.02) | 1.5E−01 | 0.619 |
| Cer(d18:2/24:1)/ Cer(d18:2/24:0) | 1.07 (1.00, 1.15) | 4.3E−02 | 0.621 | 1.06 (0.98, 1.13) | 1.3E−01 | 0.619 | 0.97 (0.90, 1.05) | 4.5E−01 | 0.620 |
| Cer(d20:1/23:0)/ PC 17:0/20:4 | 1.07 (1.00, 1.15) | 4.6E−02 | 0.620 | 1.05 (0.98, 1.13) | 1.4E−01 | 0.620 | 0.99 (0.92, 1.07) | 8.5E−01 | 0.619 |
| Cer(d18:1/26:0)/ PC 34:4 | 1.06 (1.00, 1.13) | 4.7E−02 | 0.620 | 1.01 (0.94, 1.08) | 8.1E−01 | 0.618 | 0.98 (0.91, 1.06) | 6.6E−01 | 0.619 |
| Cer(d20:1/23:0)/ PC 35:2 | 1.07 (1.00, 1.15) | 4.8E−02 | 0.621 | 1.05 (0.98, 1.13) | 1.4E−01 | 0.620 | 1.01 (0.94, 1.09) | 7.4E−01 | 0.618 |
| Cer(d18:1/23:0)/ Cer(d16:1/24:0) | 1.07 (1.00, 1.15) | 4.9E−02 | 0.620 | 1.04 (0.97, 1.11) | 3.3E−01 | 0.619 | 0.96 (0.90, 1.04) | 3.4E−01 | 0.619 |

In the examples below (Tables 3-12) the combinations of variables have been constructed using logistic regression, and unadjusted cox regression models were used to assess the predictive value of individual lipids or lipid ratios or their combinations. The results are presented both for all CV events as well as for CV death, as hazard ratios and C-statistics.

Table 3 presents an example, where combination of two ceramide/phosphatidylcholine ratios yields lower p-value and higher C-statistics as compared to individual ceramide/phosphatidylcholine ratios alone. Furthermore, additional ceramide/ceramide ratio and an individual phosphatidylcholine increases the predictive value. In addition, high sensitivity troponin (TNT) also leads into more accurate prediction.

TABLE 3

Example of combinations of lipid ratios, an individual lipid concentration and other cardiovascular biomarker (TNT).

| | CV events | | | CV death | | |
|---|---|---|---|---|---|---|
| | HR | p-value | C-stat | HR | p-value | C-stat |
| Cer(d18:1/16:0)/PC 16:0/22:5 | 1.26 (1.18, 1.34) | 5.79E−13 | 0.568 | 1.41 (1.29, 1.54) | 6.18E−14 | 0.607 |
| Cer(d18:1/18:0)/PC 14:0/22:6 | 1.18 (1.11, 1.24) | 7.85E−09 | 0.561 | 1.23 (1.13, 1.32) | 3.47E−07 | 0.579 |
| Cer(d18:1/16:0)/PC 16:0/22:5 + Cer(d18:1/18:0)/PC 14:0/22:6 | 1.26 (1.19, 1.34) | 3.40E−14 | 0.573 | 1.39 (1.28, 1.51) | 2.12E−14 | 0.610 |
| Cer(d18:1/16:0)/PC 16:0/22:5 + Cer(d18:1/18:0)/PC 14:0/22:6 + Cer(d18:1/24:1)/Cer(d18:1/24:0) | 1.32 (1.24, 1.41) | 2.31E−19 | 0.586 | 1.52 (1.40, 1.65) | 1.74E−22 | 0.644 |
| Cer(d18:1/16:0)/PC 16:0/22:5 + Cer(d18:1/18:0)/PC 14:0/22:6 + Cer(d18:1/24:1)/Cer(d18:1/24:0) + PC 16:0/16:0 | 1.37 (1.29, 1.45) | 3.85E−24 | 0.598 | 1.59 (1.46, 1.73) | 1.13E−27 | 0.653 |
| Cer(d18:1/16:0)/PC 16:0/22:5 + Cer(d18:1/18:0)/PC 14:0/22:6 + Cer(d18:1/24:1)/Cer(d18:1/24:0) + TNT | 1.58 (1.50, 1.67) | 3.32E−61 | 0.659 | 1.86 (1.73, 2.01) | 5.47E−59 | 0.739 |
| Cer(d18:1/16:0)/PC 16:0/22:5 + Cer(d18:1/18:0)/PC 14:0/22:6 + Cer(d18:1/24:1)/Cer(d18:1/24:0) + PC 16:0/16:0 + TNT | 1.61 (1.52, 1.70) | 2.55E−65 | 0.661 | 1.92 (1.78, 2.07) | 1.60E−63 | 0.740 |

Table 4 presents an example, where a combination of a ceramide/phosphatidylcholine ratio and a ceramide/ceramide ratio yields lower p-value and higher C-statistics as compared to individual lipid ratios alone. Furthermore, additional ceramide/phosphatidylcholine ratio and an individual phosphatidylcholine increases the predictive value.

TABLE 4

Example of combinations of lipid ratios and an individual lipid concentration.

|  | CV events | | | CV death | | |
| --- | --- | --- | --- | --- | --- | --- |
|  | HR | p-value | C-stat | HR | p-value | C-stat |
| Cer(d18:1/24:1)/PC 16:0/22:5 | 1.27 (1.19, 1.35) | 3.86E−14 | 0.576 | 1.42 (1.30, 1.55) | 7.52E−15 | 0.619 |
| Cer(d18:1/16:0)/Cer(d18:1/24:0) | 1.20 (1.13, 1.28) | 2.73E−09 | 0.565 | 1.34 (1.23, 1.45) | 1.72E−12 | 0.610 |
| Cer(d18:1/24:1)/PC 16:0/22:5 + Cer(d18:1/16:0)/Cer(d18:1/24:0) | 1.33 (1.25, 1.42) | 7.87E−20 | 0.594 | 1.55 (1.42, 1.69) | 2.40E−23 | 0.646 |
| Cer(d18:1/24:1)/PC 16:0/22:5 + Cer(d18:1/16:0)/Cer(d18:1/24:0) + Cer(d18:1/18:0)/PC 16:0/22:6 + PC 16:0/16:0 | 1.38 (1.30, 1.46) | 1.72E−24 | 0.599 | 1.61 (1.48, 1.75) | 2.54E−27 | 0.650 |

Table 5 presents an example, where combinations of individual lipid concentrations of ceramides and phosphatidylcholines yield lower p-values and higher C-statistics when more lipids are incorporated into the model.

TABLE 5

Example of combinations of lipid concentrations.

|  | CV events | | | CV death | | |
| --- | --- | --- | --- | --- | --- | --- |
|  | HR | p-value | C-stat | HR | p-value | C-stat |
| Cer(d18:1/16:0) | 1.20 (1.13, 1.28) | 1.39E−08 | 0.554 | 1.29 (1.18, 1.41) | 2.01E−08 | 0.577 |
| Cer(d18:1/16:0) + Cer(d18:1/24:0) | 1.31 (1.23, 1.40) | 1.36E−15 | 0.575 | 1.53 (1.39, 1.68) | 5.53E−18 | 0.623 |
| Cer(d18:1/16:0) + Cer(d18:1/18:0) + Cer(d18:1/24:0) + Cer(d18:1/24:1) | 1.34 (1.25, 1.43) | 1.09E−17 | 0.583 | 1.54 (1.41, 1.70) | 1.76E−19 | 0.628 |
| Cer(d18:1/16:0) + Cer(d18:1/18:0) + Cer(d18:1/24:0) + Cer(d18:1/24:1) + PC 14:0/22:6 | 1.38 (1.29, 1.48) | 1.08E−21 | 0.596 | 1.63 (1.48, 1.79) | 1.98E−23 | 0.644 |
| Cer(d18:1/16:0) + Cer(d18:1/18:0) + Cer(d18:1/24:0) + Cer(d18:1/24:1) + PC 14:0/22:6 + PC 16:0/16:0 | 1.39 (1.30, 1.48) | 1.76E−22 | 0.596 | 1.62 (1.48, 1.78) | 1.05E−24 | 0.645 |
| Cer(d18:1/16:0) + Cer(d18:1/18:0) + Cer(d18:1/24:0) + Cer(d18:1/24:1) + PC 14:0/22:6 + PC 16:0/16:0 + PC 16:0/22:5 | 1.43 (1.34, 1.52) | 4.36E−26 | 0.601 | 1.72 (1.57, 1.89) | 1.93E−29 | 0.658 |

Table 6 presents an example, where a combination of a ceramide/ceramide ratio and a ceramide/phosphatidylcholine ratio yields lower p-value and higher C-statistics as compared to individual lipid ratios alone. Furthermore, additional ceramide/phosphatidylcholine ratio and an individual phosphatidylcholine increases the predictive value.

TABLE 6

Example of combinations of lipid ratios and an individual lipid concentration.

|  | CV events | | | CV death | | |
| --- | --- | --- | --- | --- | --- | --- |
|  | HR | p-value | C-stat | HR | p-value | C-stat |
| Cer(d18:1/24:1)/Cer(d18:1/24:0) | 1.14 (1.07, 1.21) | 3.10E−05 | 0.563 | 1.25 (1.15, 1.36) | 1.01E−07 | 0.598 |
| Cer(d18:1/16:0)/PC 16:0/22:5 | 1.26 (1.18, 1.34) | 5.79E−13 | 0.568 | 1.41 (1.29, 1.54) | 6.18E−14 | 0.607 |
| Cer(d18:1/24:1)/Cer(d18:1/24:0) + Cer(d18:1/16:0)/PC 16:0/22:5 | 1.32 (1.24, 1.41) | 2.56E−18 | 0.588 | 1.54 (1.41, 1.68) | 2.91E−22 | 0.643 |
| Cer(d18:1/24:1)/Cer(d18:1/24:0) + Cer(d18:1/16:0)/PC 16:0/22:5 + Cer(d18:1/18:0)/PC 40:8 + PC 16:0/18:3 | 1.36 (1.28, 1.45) | 1.64E−22 | 0.596 | 1.61 (1.48, 1.76) | 1.07E−27 | 0.659 |

Table 7 presents an example, where a combination of ceramide and phosphatidylcholine concentrations yields lower p-value and higher C-statistics as compared to individual lipids alone. Furthermore, additional ceramide/phosphatidylcholine ratios increase the predictive value.

TABLE 7

Example of combinations of lipid ratios and an individual lipid concentration.

| | CV events | | | CV death | | |
|---|---|---|---|---|---|---|
| | HR | p-value | C-stat | HR | p-value | C-stat |
| Cer(d18:1/18:0) | 1.17 (1.10, 1.25) | 4.87E−07 | 0.556 | 1.19 (1.08, 1.31) | 2.37E−04 | 0.562 |
| PC 16:0/20:4 | 0.93 (0.87, 1.01) | 6.90E−02 | 0.521 | 0.79 (0.70, 0.89) | 1.15E−04 | 0.565 |
| Cer(d18:1/18:0) + PC 16:0/20:4 | 1.23 (1.15, 1.32) | 5.93E−10 | 0.561 | 1.36 (1.24, 1.50) | 1.93E−10 | 0.601 |
| Cer(d18:1/18:0) + PC 16:0/20:4 + Cer(d18:1/16:0)/PC 38:7 | 1.26 (1.18, 1.33) | 8.57E−14 | 0.569 | 1.38 (1.27, 1.50) | 1.65E−14 | 0.614 |
| Cer(d18:1/18:0) + PC 16:0/20:4 + Cer(d18:1/16:0)/PC 38:7 + Cer(d18:1/24:1)/PC 18:0/20:4 | 1.29 (1.22, 1.37) | 2.82E−17 | 0.573 | 1.46 (1.35, 1.58) | 8.13E−20 | 0.626 |

Table 8 and 9 present simplifying scoring systems (points 0-12 and 0-9, respectively), where the points are given based on the quartiles (Q1-Q4) of the whole study population. For example, if the Cer(d18:1/16:0)/PC 16:0/22:5 ratio of a person belongs to the highest quartile, the person will receive 3 points. The same evaluation will be performed for the other three lipid biomarkers, and summed up.

TABLE 8

Example of a scoring system based on lipids.

| | Q1 | Q2 | Q3 | Q4 |
|---|---|---|---|---|
| Cer(d18:1/16:0)/PC 16:0/22:5 | 0 | 1 | 2 | 3 |
| Cer(d18:1/18:0)/PC 14:0/22:6 | 0 | 1 | 2 | 3 |
| Cer(d18:1/24:1)/Cer(d18:1/24:0) | 0 | 1 | 2 | 3 |
| PC 16:0/16:0 | 0 | 1 | 2 | 3 |

TABLE 9

Another example of a scoring system based on lipids.

| | Q1 | Q2 | Q3 | Q4 |
|---|---|---|---|---|
| Cer(d18:1/16:0)/PC 16:0/22:5 | 0 | 1 | 2 | 3 |
| Cer(d18:1/18:0)/PC 14:0/22:6 | 0 | 1 | 2 | 3 |
| Cer(d18:1/24:1)/Cer(d18:1/24:0) | 0 | 1 | 2 | 3 |

Table 10 and 11 present additional examples, where also a non-lipid cardiovascular biomarker, TNT, has been added into the scoring systems. In this case, the scale of scoring system is 0-15 and 0-12, respectively.

TABLE 10

Example of a scoring system based on lipids and TNT.

| | Q1 | Q2 | Q3 | Q4 |
|---|---|---|---|---|
| Cer(d18:1/16:0)/PC 16:0/22:5 | 0 | 1 | 2 | 3 |
| Cer(d18:1/18:0)/PC 14:0/22:6 | 0 | 1 | 2 | 3 |
| Cer(d18:1/24:1)/Cer(d18:1/24:0) | 0 | 1 | 2 | 3 |
| PC 16:0/16:0 | 0 | 1 | 2 | 3 |
| TNT | 0 | 1 | 2 | 3 |

TABLE 11

Another example of a scoring system based on lipids and TNT.

| | Q1 | Q2 | Q3 | Q4 |
|---|---|---|---|---|
| Cer(d18:1/16:0)/PC 16:0/22:5 | 0 | 1 | 2 | 3 |
| Cer(d18:1/18:0)/PC 14:0/22:6 | 0 | 1 | 2 | 3 |
| Cer(d18:1/24:1)/Cer(d18:1/24:0) | 0 | 1 | 2 | 3 |
| TNT | 0 | 1 | 2 | 3 |

Table 12 presents an example of the predictive value of the scoring systems. In this example, CV score (3 components) refers to the scoring system presented in Table 9, CV score (4 components) to the scoring system presented in Table 8 and CV score (4 components+TNT) to the scoring system presented in Table 10. As shown in this example, the scores give lower p-values and higher C-statistics than e.g. individual ceramide/phosphatidylcholine ratios.

TABLE 12

Predictive value of the scoring systems as compared to individual lipid ratios.

| | CV events | | | CV death | | |
|---|---|---|---|---|---|---|
| | HR | p-value | C-stat | HR | p-value | C-stat |
| Cer(d18:1/16:0)/PC 16:0/22:5 | 1.26 (1.18, 1.34) | 5.79E−13 | 0.568 | 1.41 (1.29, 1.54) | 6.18E−14 | 0.607 |
| Cer(d18:1/18:0)/PC 14:0/22:6 | 1.18 (1.11, 1.24) | 7.85E−09 | 0.561 | 1.23 (1.13, 1.32) | 3.47E−07 | 0.579 |
| CV score (3 components) | 1.40 (1.30, 1.50) | 1.15E−19 | 0.591 | 1.61 (1.44, 1.80) | 4.11E−17 | 0.628 |
| CV score (4 components) | 1.41 (1.31, 1.51) | 5.44E−21 | 0.590 | 1.66 (1.49, 1.85) | 2.81E−20 | 0.633 |
| CV score (4 components + TNT) | 1.67 (1.56, 1.80) | 2.90E−46 | 0.637 | 2.20 (1.97, 2.45) | 1.42E−45 | 0.705 |

Tables 13-18 show results of the second study cohort. Table 13 presents examples of ceramide and phosphatidylcholine combinations which predict acute coronary syndrome in the population study cohort subjects.

TABLE 13

Hazard ratios (HR) and p-values of ceramide and phosphatidylcholine combinations in subjects who developed acute coronary syndrome during the follow-up. CV score (4 components) refers to the scoring system presented in Table 8 and CV score (3 components) to the scoring system presented in Table 9.

| Lipid combination | Acute coronary syndrome | | |
|---|---|---|---|
| | HR | 95% CI | p-value |
| Cer(d18:1/22:0)/Cer(d18:2/24:0) | 1.35 | (1.25, 1.45) | 2.8E−15 |
| CV score (4 components) | 1.34 | (1.23, 1.47) | 3.1E−10 |
| Cer(d18:1/18:0)/PC 38:7 | 1.26 | (1.17, 1.35) | 1.5E−09 |
| Cer(d18:1/18:0)/PC 16:0/22:5 | 1.27 | (1.17, 1.37) | 4.0E−09 |
| Cer(d18:1/22:0)/PC 40:8 | 1.14 | (1.09, 1.19) | 7.1E−09 |
| Cer(d18:1/24:1)/PC 38:7 | 1.26 | (1.16, 1.36) | 9.1E−09 |
| Cer(d18:1/24:1)/PC 40:8 | 1.25 | (1.16, 1.35) | 1.7E−08 |
| Cer(d20:1/24:1)/PC 40:8 | 1.16 | (1.10, 1.22) | 4.1E−08 |
| CV score (3 components) | 1.29 | (1.18, 1.41) | 4.2E−08 |
| Cer(d18:1/24:1)/PC 16:0/22:5 | 1.25 | (1.15, 1.36) | 8.2E−08 |
| Cer(d18:1/22:0)/PC 38:7 | 1.22 | (1.13, 1.31) | 1.3E−07 |
| Cer(d20:1/22:0)/PC 16:0/22:5 | 1.22 | (1.13, 1.32) | 1.6E−07 |
| Cer(d18:1/16:0)/PC 16:0/22:5 | 1.25 | (1.15, 1.35) | 1.9E−07 |
| Cer(d20:1/24:1)/PC 38:7 | 1.20 | (1.12, 1.28) | 3.5E−07 |
| Cer(d18:1/18:0)/PC 36:6 | 1.21 | (1.12, 1.30) | 3.6E−07 |
| Cer(d18:1/20:0)/Cer(d18:2/24:0) | 1.15 | (1.09, 1.22) | 1.2E−06 |
| Cer(d18:1/22:0)/PC 16:0/22:5 | 1.22 | (1.12, 1.32) | 2.2E−06 |
| Cer(d18:1/20:0)/PC 16:0/22:5 | 1.21 | (1.11, 1.31) | 4.4E−06 |
| Cer(d20:1/22:0)/Cer(d18:2/24:0) | 1.07 | (1.04, 1.10) | 9.0E−06 |
| Cer(d16:1/18:0)/PC 38:7 | 1.10 | (1.05, 1.15) | 1.4E−05 |
| Cer(d20:1/24:1)/PC 40:6 | 1.17 | (1.09, 1.26) | 1.5E−05 |
| Cer(d18:1/24:1)/PC 36:6 | 1.18 | (1.10, 1.28) | 1.6E−05 |
| Cer(d20:1/24:1)/PC 36:6 | 1.17 | (1.08, 1.25) | 3.0E−05 |
| Cer(d18:1/22:0)/PC 35:2 | 1.16 | (1.08, 1.24) | 3.3E−05 |
| Cer(d18:1/22:0)/PC 37:2 | 1.18 | (1.09, 1.28) | 4.9E−05 |
| Cer(d20:1/24:1)/PC 16:0/22:5 | 1.17 | (1.08, 1.26) | 5.1E−05 |
| Cer(d18:1/22:0)/PC 36:6 | 1.18 | (1.09, 1.28) | 5.4E−05 |
| Cer(d20:1/24:1)/PC 39:4 | 1.15 | (1.07, 1.23) | 5.5E−05 |
| Cer(d18:1/16:0)/PC 36:6 | 1.18 | (1.09, 1.28) | 5.7E−05 |
| Cer(d18:1/20:0)/PC 36:6 | 1.13 | (1.06, 1.21) | 1.1E−04 |
| Cer(d18:1/20:0)/PC 38:7 | 1.07 | (1.03, 1.10) | 1.3E−04 |
| Cer(d16:1/18:0)/PC 36:6 | 1.16 | (1.07, 1.25) | 1.4E−04 |
| Cer(d16:1/20:0)/Cer(d18:2/24:0) | 1.11 | (1.05, 1.17) | 1.5E−04 |
| Cer(d18:1/22:0)/PC 36:0 | 1.17 | (1.08, 1.26) | 1.6E−04 |
| Cer(d20:1/24:1)/PC 37:2 | 1.14 | (1.07, 1.23) | 1.9E−04 |
| Cer(d16:1/20:0)/PC 36:6 | 1.09 | (1.04, 1.15) | 2.9E−04 |
| Cer(d20:1/22:0)/PC 36:6 | 1.06 | (1.03, 1.10) | 3.1E−04 |
| Cer(d20:1/24:1)/PC 40:5 | 1.15 | (1.06, 1.24) | 3.1E−04 |
| Cer(d20:1/24:1)/PC 35:4 | 1.12 | (1.05, 1.19) | 4.1E−04 |
| Cer(d20:1/24:1)/PC 36:0 | 1.15 | (1.06, 1.24) | 4.1E−04 |
| Cer(d16:1/18:0)/Cer(d18:2/24:0) | 1.15 | (1.07, 1.25) | 4.3E−04 |
| Cer(d20:1/22:0)/PC 36:0 | 1.06 | (1.03, 1.09) | 4.5E−04 |
| Cer(d20:1/24:1)/PC 38:1 | 1.15 | (1.06, 1.25) | 5.0E−04 |
| Cer(d16:1/20:0)/PC 16:0/22:5 | 1.16 | (1.06, 1.25) | 5.7E−04 |
| Cer(d16:1/18:0)/PC 16:0/22:5 | 1.15 | (1.06, 1.25) | 5.9E−04 |
| Cer(d16:1/18:0)/PC 40:8 | 1.06 | (1.02, 1.10) | 1.1E−03 |
| Cer(d16:1/18:0)/PC 39:4 | 1.09 | (1.04, 1.16) | 1.4E−03 |
| Cer(d16:1/18:0)/PC 37:2 | 1.11 | (1.04, 1.19) | 3.1E−03 |
| Cer(d18:1/22:0)/Cer(d18:1/24:1) | 1.13 | (1.04, 1.23) | 5.3E−03 |
| Cer(d16:1/18:0)/PC 35:0 | 1.12 | (1.03, 1.22) | 5.5E−03 |
| Cer(d16:1/20:0)/PC 35:0 | 1.12 | (1.03, 1.22) | 5.6E−03 |
| Cer(d16:1/16:0)/Cer(d18:2/24:0) | 1.08 | (1.02, 1.14) | 6.3E−03 |
| Cer(d20:1/22:0)/PC 37:2 | 1.04 | (1.01, 1.08) | 7.4E−03 |
| Cer(d18:2/16:0)/PC 38:7 | 1.09 | (1.02, 1.16) | 9.3E−03 |

95% CI = 95% confidence interval.

Table 14 presents examples of ceramide and phosphatidylcholine combinations which predict cardiovascular death in the population study cohort subjects.

TABLE 14

Hazard ratios (HR) and p-values of ceramide and phosphatidylcholine combinations in subjects who died due to cardiovascular reasons during the follow-up. CV score (4 components) refers to the scoring system presented in Table 8 and CV score (3 components) to the scoring system presented in Table 9.

| Lipid combination | Cardiovascular death | | |
|---|---|---|---|
| | HR | 95% CI | p-value |
| Cer(d18:1/22:0)/Cer(d18:2/24:0) | 1.57 | (1.40, 1.77) | 6.5E−14 |
| Cer(d18:1/20:0)/Cer(d18:2/24:0) | 1.24 | (1.14, 1.33) | 4.9E−08 |
| CV score (4 components) | 1.59 | (1.34, 1.88) | 5.4E−08 |
| Cer(d20:1/24:1)/PC 40:8 | 1.24 | (1.15, 1.34) | 5.9E−08 |
| Cer(d18:1/22:0)/PC 40:8 | 1.19 | (1.11, 1.27) | 8.9E−07 |
| Cer(d18:1/18:0)/PC 38:7 | 1.35 | (1.19, 1.53) | 4.2E−06 |
| Cer(d20:1/22:0)/Cer(d18:2/24:0) | 1.10 | (1.05, 1.14) | 4.9E−06 |
| CV score (3 components) | 1.46 | (1.24, 1.72) | 6.6E−06 |
| Cer(d16:1/20:0)/Cer(d18:2/24:0) | 1.17 | (1.09, 1.25) | 8.1E−06 |
| Cer(d18:1/18:0)/PC 36:6 | 1.32 | (1.17, 1.50) | 9.4E−06 |
| Cer(d16:1/16:0)/Cer(d18:2/24:0) | 1.14 | (1.07, 1.21) | 4.3E−05 |
| Cer(d20:1/24:1)/PC 40:6 | 1.27 | (1.13, 1.43) | 4.5E−05 |
| Cer(d16:1/18:0)/Cer(d18:2/24:0) | 1.30 | (1.15, 1.48) | 4.7E−05 |
| Cer(d18:1/18:0)/PC 16:0/22:5 | 1.32 | (1.15, 1.50) | 4.9E−05 |
| Cer(d16:1/18:0)/PC 36:6 | 1.27 | (1.13, 1.43) | 5.4E−05 |
| Cer(d18:1/24:1)/PC 40:8 | 1.31 | (1.15, 1.49) | 6.6E−05 |
| Cer(d16:1/18:0)/PC 38:7 | 1.14 | (1.07, 1.22) | 7.5E−05 |
| Cer(d18:1/20:0)/PC 36:6 | 1.21 | (1.10, 1.32) | 8.3E−05 |
| Cer(d16:1/18:0)/PC 37:2 | 1.21 | (1.10, 1.33) | 1.0E−04 |
| Cer(d20:1/24:1)/PC 36:6 | 1.26 | (1.12, 1.42) | 1.2E−04 |
| Cer(d20:1/24:1)/PC 37:2 | 1.24 | (1.11, 1.38) | 1.2E−04 |
| Cer(d18:1/22:0)/Cer(d18:1/24:0) | 1.32 | (1.14, 1.53) | 1.6E−04 |
| Cer(d18:1/16:0)/PC 36:6 | 1.30 | (1.13, 1.49) | 1.9E−04 |
| Cer(d20:1/24:1)/PC 38:7 | 1.25 | (1.11, 1.41) | 2.2E−04 |
| Cer(d16:1/18:0)/PC 40:8 | 1.09 | (1.04, 1.15) | 2.5E−04 |
| Cer(d18:2/16:0)/PC 37:2 | 1.15 | (1.07, 1.25) | 3.5E−04 |
| Cer(d16:1/20:0)/PC 36:6 | 1.14 | (1.06, 1.22) | 4.6E−04 |
| Cer(d18:1/16:0)/PC 16:0/22:5 | 1.28 | (1.11, 1.47) | 4.8E−04 |
| Cer(d18:1/18:0)/PC 35:4 | 3.63 | (1.75, 7.56) | 5.6E−04 |
| Cer(d18:1/22:0)/PC 37:2 | 1.26 | (1.10, 1.44) | 9.3E−04 |
| Cer(d18:1/22:0)/PC 38:7 | 1.25 | (1.09, 1.44) | 1.5E−03 |
| Cer(d20:1/22:0)/PC 16:0/22:5 | 1.23 | (1.08, 1.41) | 1.8E−03 |
| Cer(d18:1/20:0)/PC 16:0/22:5 | 1.24 | (1.08, 1.43) | 2.1E−03 |
| Cer(d16:1/18:0)/PC 16:0/22:5 | 1.24 | (1.08, 1.42) | 2.3E−03 |
| Cer(d18:1/20:0)/PC 38:7 | 1.09 | (1.03, 1.15) | 2.4E−03 |
| Cer(d18:1/22:0)/PC 36:6 | 1.25 | (1.08, 1.44) | 2.6E−03 |
| Cer(d18:1/24:1)/PC 36:6 | 1.23 | (1.07, 1.41) | 2.9E−03 |
| Cer(d16:1/18:0)/PC 35:0 | 1.23 | (1.07, 1.41) | 3.7E−03 |
| Cer(d18:1/24:1)/PC 38:7 | 1.24 | (1.07, 1.44) | 3.9E−03 |
| Cer(d20:1/22:0)/PC 36:6 | 1.08 | (1.03, 1.14) | 4.0E−03 |
| Cer(d16:1/16:0)/PC 37:2 | 1.07 | (1.02, 1.13) | 4.4E−03 |
| Cer(d18:2/16:0)/PC 40:8 | 1.09 | (1.03, 1.15) | 4.7E−03 |
| Cer(d16:1/18:0)/PC 39:4 | 1.13 | (1.04, 1.24) | 5.2E−03 |
| Cer(d16:1/16:0)/PC 36:6 | 1.10 | (1.03, 1.18) | 5.8E−03 |
| Cer(d18:2/18:0)/Cer(d18:2/24:0) | 1.20 | (1.05, 1.37) | 6.3E−03 |
| Cer(d16:1/18:0)/PC 35:4 | 1.31 | (1.07, 1.60) | 7.6E−03 |
| Cer(d18:2/18:0)/PC 36:6 | 1.18 | (1.04, 1.34) | 8.8E−03 |
| Cer(d20:1/22:0)/PC 37:2 | 1.06 | (1.02, 1.11) | 9.1E−03 |
| Cer(d18:2/16:0)/PC 40:6 | 1.11 | (1.03, 1.20) | 9.1E−03 |
| Cer(d16:1/18:0)/PC 36:0 | 1.20 | (1.05, 1.38) | 9.5E−03 |
| Cer(d18:1/22:0)/PC 16:0/22:5 | 1.21 | (1.05, 1.40) | 1.0E−02 |
| Cer(d20:1/22:0)/PC 36:0 | 1.08 | (1.02, 1.14) | 1.1E−02 |
| Cer(d16:1/18:0)/PC 40:5 | 1.09 | (1.02, 1.17) | 1.2E−02 |
| Cer(d20:1/24:1)/PC 16:0/22:5 | 1.18 | (1.03, 1.34) | 1.4E−02 |
| Cer(d16:1/18:0)/PC 35:2 | 1.11 | (1.02, 1.20) | 1.4E−02 |
| Cer(d18:1/18:0)/PC 37:6 | 1.13 | (1.02, 1.24) | 1.4E−02 |
| Cer(d16:1/20:0)/PC 16:0/22:5 | 1.19 | (1.03, 1.37) | 1.5E−02 |
| Cer(d20:1/24:1)/PC 35:4 | 1.23 | (1.04, 1.46) | 1.6E−02 |
| Cer(d16:1/16:0)/PC 35:0 | 1.18 | (1.03, 1.35) | 1.8E−02 |
| Cer(d18:2/18:0)/PC 37:2 | 1.12 | (1.02, 1.24) | 1.8E−02 |
| Cer(d16:1/20:0)/PC 37:2 | 1.08 | (1.01, 1.15) | 2.0E−02 |
| Cer(d16:1/16:0)/PC 16:0/22:5 | 1.19 | (1.02, 1.38) | 2.3E−02 |
| Cer(d18:1/22:0)/PC 35:2 | 1.17 | (1.02, 1.34) | 2.5E−02 |
| Cer(d18:2/18:0)/PC 38:7 | 1.09 | (1.01, 1.17) | 2.5E−02 |
| Cer(d18:2/16:0)/Cer(d18:2/24:0) | 1.16 | (1.02, 1.32) | 2.6E−02 |
| Cer(d20:1/24:1)/PC 40:5 | 1.16 | (1.01, 1.33) | 3.1E−02 |
| Cer(d18:2/16:0)/PC 38:7 | 1.12 | (1.01, 1.24) | 3.2E−02 |
| Cer(d18:2/16:0)/PC 37:6 | 1.12 | (1.01, 1.24) | 3.3E−02 |
| Cer(d18:2/18:0)/PC 40:6 | 1.07 | (1.01, 1.14) | 3.3E−02 |

TABLE 14-continued

Hazard ratios (HR) and p-values of ceramide and phosphatidylcholine combinations in subjects who died due to cardiovascular reasons during the follow-up. CV score (4 components) refers to the scoring system presented in Table 8 and CV score (3 components) to the scoring system presented in Table 9.

| | Cardiovascular death | | |
|---|---|---|---|
| Lipid combination | HR | 95% CI | p-value |
| Cer(d18:1/22:0)/PC 36:0 | 1.16 | (1.01, 1.33) | 3.6E−02 |
| Cer(d20:1/24:1)/PC 35:5 | 1.15 | (1.01, 1.30) | 3.6E−02 |
| Cer(d20:1/24:1)/PC 39:4 | 1.13 | (1.01, 1.27) | 3.7E−02 |
| Cer(d20:1/24:1)/PC 36:0 | 1.15 | (1.01, 1.31) | 3.8E−02 |
| Cer(d18:1/16:0)/PC 37:6 | 1.11 | (1.00, 1.23) | 4.1E−02 |
| Cer(d18:1/20:0)/PC 35:4 | 1.52 | (1.01, 2.28) | 4.2E−02 |
| Cer(d16:1/18:0)/PC 35:5 | 1.15 | (1.00, 1.33) | 4.7E−02 |

95% CI = 95% confidence interval.

Table 15 presents examples of ceramide and phosphatidylcholine combinations which predict heart failure in the population study cohort subjects.

TABLE 15

Hazard ratios (HR) and p-values of ceramide and phosphatidylcholine combinations in subjects who developed heart failure during the follow-up. CV score (4 components) refers to the scoring system presented in Table 8 and CV score (3 components) to the scoring system presented in Table 9.

| | Heart failure | | |
|---|---|---|---|
| Lipid combination | HR | 95% CI | p-value |
| Cer(d18:1/24:1)/PC 40:8 | 1.35 | (1.26, 1.45) | 1.1E−16 |
| Cer(d18:1/22:0)/PC 40:8 | 1.14 | (1.10, 1.19) | 7.5E−12 |
| Cer(d18:1/22:0)/Cer(d18:2/24:0) | 1.28 | (1.19, 1.37) | 3.0E−11 |
| Cer(d18:1/18:0)/PC 38:7 | 1.28 | (1.19, 1.37) | 7.4E−11 |
| Cer(d20:1/24:1)/PC 40:8 | 1.17 | (1.12, 1.23) | 1.3E−10 |
| Cer(d16:1/20:0)/Cer(d18:2/24:0) | 1.13 | (1.08, 1.18) | 3.2E−09 |
| Cer(d18:1/24:1)/PC 38:7 | 1.27 | (1.17, 1.37) | 3.3E−09 |
| Cer(d18:1/20:0)/Cer(d18:2/24:0) | 1.16 | (1.10, 1.22) | 1.7E−08 |
| Cer(d18:1/18:0)/PC 36:6 | 1.22 | (1.13, 1.31) | 4.3E−08 |
| CV score (4 components) | 1.27 | (1.17, 1.39) | 5.7E−08 |
| Cer(d16:1/18:0)/PC 38:7 | 1.11 | (1.07, 1.15) | 1.3E−07 |
| Cer(d18:1/18:0)/PC 16:0/22:5 | 1.22 | (1.13, 1.31) | 1.4E−07 |
| Cer(d18:2/24:1)/PC 40:8 | 1.20 | (1.12, 1.28) | 1.5E−07 |
| Cer(d16:1/18:0)/Cer(d18:2/24:0) | 1.21 | (1.12, 1.30) | 3.2E−07 |
| Cer(d16:1/18:0)/PC 40:8 | 1.07 | (1.04, 1.10) | 5.5E−07 |
| Cer(d16:1/18:0)/PC 36:6 | 1.19 | (1.11, 1.28) | 8.3E−07 |
| CV score (3 components) | 1.23 | (1.13, 1.34) | 2.1E−06 |
| Cer(d20:1/24:1)/PC 38:7 | 1.19 | (1.11, 1.28) | 2.6E−06 |
| Cer(d18:1/24:1)/PC 36:6 | 1.20 | (1.11, 1.30) | 3.2E−06 |
| Cer(d18:1/20:0)/PC 36:6 | 1.14 | (1.08, 1.21) | 5.0E−06 |
| Cer(d18:2/16:0)/PC 40:8 | 1.07 | (1.04, 1.10) | 6.5E−06 |
| Cer(d18:1/22:0)/PC 38:7 | 1.19 | (1.10, 1.29) | 7.0E−06 |
| Cer(d16:1/20:0)/PC 36:6 | 1.10 | (1.05, 1.15) | 1.3E−05 |
| Cer(d16:1/16:0)/PC 36:6 | 1.19 | (1.10, 1.29) | 1.4E−05 |
| Cer(d16:1/18:0)/PC 35:0 | 1.18 | (1.09, 1.27) | 3.1E−05 |
| Cer(d18:1/24:1)/PC 16:0/22:5 | 1.17 | (1.09, 1.27) | 5.0E−05 |
| Cer(d16:1/20:0)/PC 35:0 | 1.17 | (1.08, 1.26) | 5.5E−05 |
| Cer(d18:1/20:0)/PC 38:7 | 1.07 | (1.03, 1.10) | 5.7E−05 |
| Cer(d20:1/24:1)/PC 36:6 | 1.17 | (1.08, 1.26) | 7.6E−05 |
| Cer(d20:1/22:0)/Cer(d18:2/24:0) | 1.06 | (1.03, 1.10) | 8.8E−05 |
| Cer(d18:1/16:0)/PC 16:0/22:5 | 1.16 | (1.08, 1.25) | 9.5E−05 |
| Cer(d16:1/18:0)/PC 37:2 | 1.13 | (1.06, 1.20) | 1.1E−04 |
| Cer(d16:1/18:0)/PC 36:0 | 1.16 | (1.07, 1.25) | 1.4E−04 |
| Cer(d18:1/22:0)/PC 36:6 | 1.17 | (1.08, 1.28) | 1.9E−04 |
| Cer(d18:2/16:0)/PC 38:7 | 1.10 | (1.05, 1.16) | 2.3E−04 |
| Cer(d16:1/18:0)/PC 35:2 | 1.08 | (1.04, 1.13) | 2.6E−04 |
| Cer(d18:1/20:0)/PC 16:0/22:5 | 1.15 | (1.07, 1.24) | 3.3E−04 |
| Cer(d16:1/20:0)/PC 36:0 | 1.09 | (1.04, 1.15) | 3.5E−04 |
| Cer(d16:1/18:0)/PC 16:0/22:5 | 1.15 | (1.07, 1.24) | 3.6E−04 |
| Cer(d16:1/18:0)/PC 35:5 | 1.14 | (1.06, 1.23) | 4.9E−04 |
| Cer(d20:1/24:1)/PC 36:0 | 1.13 | (1.05, 1.21) | 9.0E−04 |
| Cer(d18:1/24:1)/PC 35:5 | 1.14 | (1.05, 1.23) | 9.6E−04 |

TABLE 15-continued

Hazard ratios (HR) and p-values of ceramide and phosphatidylcholine combinations in subjects who developed heart failure during the follow-up. CV score (4 components) refers to the scoring system presented in Table 8 and CV score (3 components) to the scoring system presented in Table 9.

| | Heart failure | | |
|---|---|---|---|
| Lipid combination | HR | 95% CI | p-value |
| Cer(d16:1/18:0)/PC 39:4 | 1.09 | (1.04, 1.15) | 1.1E−03 |
| Cer(d20:1/24:1)/PC 35:5 | 1.13 | (1.05, 1.22) | 1.3E−03 |
| Cer(d16:1/16:0)/Cer(d18:2/24:0) | 1.08 | (1.03, 1.14) | 1.4E−03 |
| Cer(d20:1/24:1)/PC 40:6 | 1.14 | (1.05, 1.23) | 1.5E−03 |
| Cer(d18:2/24:1)/PC 38:7 | 1.15 | (1.05, 1.25) | 1.6E−03 |
| Cer(d20:1/22:0)/PC 16:0/22:5 | 1.13 | (1.05, 1.22) | 1.7E−03 |
| Cer(d18:1/22:0)/PC 36:0 | 1.13 | (1.05, 1.22) | 1.7E−03 |
| Cer(d18:1/20:0)/PC 35:5 | 1.11 | (1.04, 1.18) | 1.9E−03 |
| Cer(d16:1/20:0)/PC 37:2 | 1.06 | (1.02, 1.10) | 2.0E−03 |
| Cer(d18:1/22:0)/PC 37:2 | 1.13 | (1.05, 1.23) | 2.3E−03 |
| Cer(d16:1/18:0)/PC 40:5 | 1.07 | (1.02, 1.11) | 2.3E−03 |
| Cer(d16:1/20:0)/PC 16:0/22:5 | 1.13 | (1.04, 1.22) | 2.3E−03 |
| Cer(d20:1/24:1)/PC 16:0/22:5 | 1.12 | (1.04, 1.21) | 2.7E−03 |
| Cer(d18:1/22:0)/PC 35:2 | 1.12 | (1.04, 1.20) | 3.1E−03 |
| Cer(d20:1/24:1)/PC 37:2 | 1.11 | (1.04, 1.20) | 3.4E−03 |
| Cer(d20:1/24:1)/PC 35:4 | 1.11 | (1.03, 1.18) | 4.2E−03 |
| Cer(d20:1/22:0)/PC 36:0 | 1.05 | (1.02, 1.09) | 5.4E−03 |
| Cer(d20:1/24:1)/PC 40:5 | 1.11 | (1.03, 1.20) | 5.7E−03 |
| Cer(d18:1/22:0)/PC 16:0/22:5 | 1.12 | (1.03, 1.21) | 6.1E−03 |
| Cer(d16:1/18:0)/PC 38:5 | 1.08 | (1.02, 1.14) | 6.1E−03 |
| Cer(d18:2/18:0)/PC 36:6 | 1.11 | (1.03, 1.20) | 6.9E−03 |
| Cer(d18:2/24:1)/PC 36:6 | 1.13 | (1.03, 1.23) | 6.9E−03 |
| Cer(d20:1/22:0)/PC 36:6 | 1.05 | (1.01, 1.09) | 7.4E−03 |
| Cer(d18:2/18:0)/PC 38:7 | 1.06 | (1.02, 1.11) | 7.5E−03 |
| Cer(d18:2/16:0)/PC 36:6 | 1.12 | (1.03, 1.22) | 7.8E−03 |
| Cer(d20:1/24:1)/PC 39:4 | 1.10 | (1.02, 1.18) | 8.3E−03 |
| Cer(d16:1/16:0)/PC 36:6 | 1.07 | (1.02, 1.12) | 8.5E−03 |

95% CI = 95% confidence interval.

Table 16 presents examples of ceramide and phosphatidylcholine combinations which predict myocardial infarction in the population study cohort subjects.

TABLE 16

Hazard ratios (HR) and p-values of ceramide and phosphatidylcholine combinations in subjects who developed myocardial infarction during the follow-up. CV score (4 components) refers to the scoring system presented in Table 8 and CV score (3 components) to the scoring system presented in Table 9.

| | Myocardial infarction | | |
|---|---|---|---|
| Lipid combination | HR | 95% CI | p-value |
| Cer(d18:1/22:0)/Cer(d18:2/24:0) | 1.36 | (1.23, 1.50) | 4.1E−10 |
| CV score (4 components) | 1.47 | (1.30, 1.66) | 4.8E−10 |
| Cer(d18:1/18:0)/PC 16:0/22:5 | 1.31 | (1.19, 1.45) | 1.0E−07 |
| CV score (3 components) | 1.38 | (1.22, 1.55) | 1.5E−07 |
| Cer(d18:1/22:0)/PC 40:8 | 1.15 | (1.09, 1.21) | 2.7E−07 |
| Cer(d18:1/24:1)/PC 16:0/22:5 | 1.30 | (1.17, 1.44) | 5.8E−07 |
| Cer(d20:1/24:1)/PC 16:0/22:5 | 1.27 | (1.15, 1.39) | 7.6E−07 |
| Cer(d18:1/24:1)/PC 40:8 | 1.28 | (1.16, 1.42) | 1.2E−06 |
| Cer(d18:1/20:0)/PC 16:0/22:5 | 1.27 | (1.15, 1.41) | 2.3E−06 |
| Cer(d18:1/16:0)/PC 16:0/22:5 | 1.28 | (1.15, 1.42) | 2.9E−06 |
| Cer(d18:1/22:0)/PC 16:0/22:5 | 1.26 | (1.14, 1.40) | 6.5E−06 |
| Cer(d20:1/24:1)/PC 40:8 | 1.17 | (1.09, 1.25) | 1.3E−05 |
| Cer(d18:1/18:0)/PC 38:7 | 1.24 | (1.12, 1.37) | 1.6E−05 |
| Cer(d18:1/24:1)/PC 38:7 | 1.24 | (1.12, 1.38) | 3.6E−05 |
| Cer(d16:1/16:0)/PC 16:0/22:5 | 1.23 | (1.11, 1.36) | 6.3E−05 |
| Cer(d20:1/22:0)/Cer(d18:2/24:0) | 1.07 | (1.04, 1.11) | 8.2E−05 |
| Cer(d16:1/18:0)/PC 16:0/22:5 | 1.22 | (1.11, 1.36) | 9.9E−05 |
| Cer(d18:1/22:0)/PC 38:7 | 1.21 | (1.09, 1.33) | 1.9E−04 |
| Cer(d16:1/18:0)/PC 38:7 | 1.11 | (1.05, 1.17) | 2.6E−04 |
| Cer(d20:1/24:1)/PC 16:0/22:5 | 1.19 | (1.08, 1.31) | 3.8E−04 |
| Cer(d18:1/18:0)/PC 36:6 | 1.20 | (1.08, 1.32) | 4.3E−04 |
| Cer(d16:1/20:0)/PC 35:0 | 1.20 | (1.08, 1.32) | 4.3E−04 |
| Cer(d18:1/18:0)/PC 35:4 | 2.71 | (1.55, 4.72) | 4.4E−04 |
| Cer(d18:1/20:0)/Cer(d18:2/24:0) | 1.15 | (1.06, 1.24) | 4.7E−04 |

TABLE 16-continued

Hazard ratios (HR) and p-values of ceramide and phosphatidylcholine combinations in subjects who developed myocardial infarction during the follow-up. CV score (4 components) refers to the scoring system presented in Table 8 and CV score (3 components) to the scoring system presented in Table 9.

| Lipid combination | Myocardial infarction | | |
|---|---|---|---|
| | HR | 95% CI | p-value |
| Cer(d16:1/20:0)/Cer(d18:2/24:0) | 1.12 | (1.05, 1.19) | 5.7E−04 |
| Cer(d20:1/24:1)/PC 38:7 | 1.18 | (1.07, 1.29) | 6.4E−04 |
| Cer(d16:1/18:0)/PC 40:8 | 1.07 | (1.03, 1.12) | 1.2E−03 |
| Cer(d16:1/18:0)/PC 35:0 | 1.18 | (1.07, 1.31) | 1.2E−03 |
| Cer(d18:1/22:0)/PC 36:0 | 1.18 | (1.07, 1.31) | 1.3E−03 |
| Cer(d18:1/20:0)/PC 36:6 | 1.14 | (1.05, 1.24) | 1.5E−03 |
| Cer(d18:1/22:0)/PC 35:2 | 1.16 | (1.06, 1.27) | 1.5E−03 |
| Cer(d16:1/20:0)/PC 36:6 | 1.10 | (1.04, 1.17) | 1.6E−03 |
| Cer(d18:1/24:1)/PC 36:6 | 1.18 | (1.06, 1.30) | 1.7E−03 |
| Cer(d16:1/18:0)/PC 36:6 | 1.17 | (1.06, 1.29) | 1.8E−03 |
| Cer(d18:1/20:0)/PC 38:7 | 1.07 | (1.02, 1.11) | 2.0E−03 |
| Cer(d20:1/22:0)/PC 36:0 | 1.06 | (1.02, 1.11) | 2.0E−03 |
| Cer(d16:1/18:0)/Cer(d18:2/24:0) | 1.17 | (1.06, 1.30) | 2.2E−03 |
| Cer(d18:1/22:0)/Cer(d18:1/24:0) | 1.19 | (1.06, 1.32) | 2.2E−03 |
| Cer(d18:1/22:0)/PC 37:2 | 1.17 | (1.06, 1.30) | 2.7E−03 |
| Cer(d16:1/18:0)/PC 35:4 | 1.25 | (1.08, 1.44) | 2.7E−03 |
| Cer(d18:1/22:0)/PC 36:6 | 1.18 | (1.06, 1.31) | 3.0E−03 |
| Cer(d18:1/22:0)/PC 35:4 | 1.93 | (1.25, 2.98) | 3.0E−03 |
| Cer(d20:1/24:1)/PC 38:1 | 1.17 | (1.05, 1.29) | 3.2E−03 |
| Cer(d16:1/18:0)/PC 39:4 | 1.10 | (1.03, 1.18) | 3.9E−03 |
| Cer(d16:1/20:0)/PC 36:0 | 1.10 | (1.03, 1.17) | 4.6E−03 |
| Cer(d20:1/24:1)/PC 40:5 | 1.15 | (1.04, 1.27) | 4.6E−03 |
| Cer(d16:1/22:0)/PC 35:4 | 2.26 | (1.28, 3.99) | 4.9E−03 |
| Cer(d20:1/22:0)/PC 36:6 | 1.06 | (1.02, 1.11) | 7.1E−03 |
| Cer(d16:1/18:0)/PC 36:0 | 1.15 | (1.04, 1.28) | 7.4E−03 |
| Cer(d20:1/24:1)/PC 36:6 | 1.14 | (1.04, 1.26) | 7.6E−03 |
| Cer(d18:1/16:0)/PC 36:6 | 1.16 | (1.04, 1.30) | 8.7E−03 |
| Cer(d16:1/18:0)/PC 37:2 | 1.12 | (1.03, 1.23) | 8.9E−03 |

95% CI = 95% confidence interval.

Table 17 presents examples of ceramide and phosphatidylcholine combinations which predict peripheral artery disease in the population study cohort subjects.

TABLE 17

Hazard ratios (HR) and p-values of ceramide and phosphatidylcholine combinations in subjects who developed peripheral artery disease during the follow-up. CV score (4 components) refers to the scoring system presented in Table 8 and CV score (3 components) to the scoring system presented in Table 9.

| Lipid combination | Peripheral artery disease | | |
|---|---|---|---|
| | HR | 95% CI | p-value |
| Cer(d18:1/24:1)/PC 40:8 | 1.34 | (1.18, 1.53) | 1.3E−05 |
| Cer(d18:1/18:0)/PC 38:7 | 1.32 | (1.16, 1.51) | 3.5E−05 |
| Cer(d20:1/24:1)/PC 40:8 | 1.19 | (1.09, 1.30) | 5.3E−05 |
| CV score (4 components) | 1.39 | (1.18, 1.64) | 7.9E−05 |
| Cer(d18:1/24:1)/PC 38:7 | 1.32 | (1.15, 1.52) | 8.0E−05 |
| Cer(d18:2/18:0)/PC 36:5 | 2.41 | (1.52, 3.80) | 1.7E−04 |
| Cer(d20:1/24:1)/PC 38:7 | 1.26 | (1.12, 1.43) | 1.8E−04 |
| Cer(d18:1/20:0)/Cer(d18:2/24:0) | 1.18 | (1.08, 1.29) | 2.1E−04 |
| CV score (3 components) | 1.36 | (1.15, 1.60) | 2.6E−04 |
| Cer(d18:1/22:0)/Cer(d18:2/24:0) | 1.29 | (1.13, 1.48) | 2.7E−04 |
| Cer(d18:1/18:0)/PC 36:6 | 1.24 | (1.11, 1.40) | 2.8E−04 |
| Cer(d18:1/22:0)/PC 40:8 | 1.14 | (1.06, 1.24) | 6.4E−04 |
| Cer(d18:1/24:1)/PC 36:6 | 1.25 | (1.09, 1.42) | 1.1E−03 |
| Cer(d18:1/18:0)/PC 16:0/22:5 | 1.26 | (1.09, 1.45) | 1.3E−03 |
| Cer(d18:1/16:0)/PC 36:6 | 1.24 | (1.08, 1.42) | 1.8E−03 |
| Cer(d18:1/20:0)/PC 36:6 | 1.17 | (1.06, 1.29) | 2.0E−03 |
| Cer(d20:1/24:1)/PC 36:6 | 1.22 | (1.07, 1.39) | 3.0E−03 |
| Cer(d20:1/24:1)/PC 36:0 | 1.20 | (1.06, 1.36) | 3.9E−03 |
| Cer(d20:1/24:1)/PC 40:6 | 1.20 | (1.06, 1.36) | 3.9E−03 |
| Cer(d20:1/24:1)/PC 40:5 | 1.20 | (1.06, 1.36) | 4.6E−03 |
| Cer(d18:1/16:0)/PC 16:0/22:5 | 1.23 | (1.06, 1.41) | 4.7E−03 |
| Cer(d20:1/22:0)/Cer(d18:2/24:0) | 1.07 | (1.02, 1.13) | 5.0E−03 |

TABLE 17-continued

Hazard ratios (HR) and p-values of ceramide and phosphatidylcholine combinations in subjects who developed peripheral artery disease during the follow-up. CV score (4 components) refers to the scoring system presented in Table 8 and CV score (3 components) to the scoring system presented in Table 9.

| Lipid combination | Peripheral artery disease | | |
|---|---|---|---|
| | HR | 95% CI | p-value |
| Cer(d18:1/20:0)/PC 38:7 | 1.07 | (1.02, 1.13) | 6.7E−03 |
| Cer(d18:2/16:0)/PC 38:7 | 1.12 | (1.03, 1.22) | 6.8E−03 |
| Cer(d18:1/22:0)/PC 38:7 | 1.21 | (1.05, 1.39) | 7.1E−03 |
| Cer(d16:1/18:0)/PC 38:7 | 1.11 | (1.03, 1.20) | 8.9E−03 |

95% CI = 95% confidence interval.

Table 18 presents examples of ceramide and phosphatidylcholine combinations which predict stroke in the population study cohort subjects.

TABLE 18

Hazard ratios (HR) and p-values of ceramide and phosphatidylcholine combinations in subjects who developed stroke during the follow-up. CV score (4 components) refers to the scoring system presented in Table 8 and CV score (3 components) to the scoring system presented in Table 9.

| Lipid combination | Stroke | | |
|---|---|---|---|
| | HR | 95% CI | p-value |
| Cer(d18:1/20:0)/Cer(d18:2/24:0) | 1.19 | (1.12, 1.25) | 4.5E−10 |
| Cer(d18:1/22:0)/Cer(d18:2/24:0) | 1.30 | (1.19, 1.42) | 6.2E−09 |
| CV score (4 components) | 1.32 | (1.19, 1.47) | 2.2E−07 |
| CV score (3 components) | 1.28 | (1.15, 1.42) | 3.3E−06 |
| Cer(d20:1/24:1)/PC 40:8 | 1.15 | (1.08, 1.23) | 2.8E−05 |
| Cer(d20:1/24:1)/PC 36:6 | 1.19 | (1.09, 1.30) | 1.0E−04 |
| Cer(d20:1/22:0)/Cer(d18:2/24:0) | 1.07 | (1.03, 1.11) | 1.0E−04 |
| Cer(d18:1/24:1)/PC 40:8 | 1.20 | (1.09, 1.31) | 1.4E−04 |
| Cer(d18:1/18:0)/PC 38:7 | 1.19 | (1.09, 1.30) | 2.2E−04 |
| Cer(d20:1/24:1)/PC 38:7 | 1.17 | (1.08, 1.28) | 3.3E−04 |
| Cer(d16:1/20:0)/Cer(d18:2/24:0) | 1.11 | (1.05, 1.18) | 3.8E−04 |
| Cer(d18:1/18:0)/PC 36:6 | 1.17 | (1.07, 1.28) | 4.3E−04 |
| Cer(d20:1/24:1)/PC 35:4 | 1.09 | (1.04, 1.14) | 4.3E−04 |
| Cer(d18:1/22:0)/PC 40:8 | 1.11 | (1.04, 1.19) | 1.1E−03 |
| Cer(d18:1/16:0)/PC 36:6 | 1.17 | (1.06, 1.29) | 1.2E−03 |
| Cer(d20:1/24:1)/PC 35:5 | 1.15 | (1.06, 1.25) | 1.2E−03 |
| Cer(d18:1/24:1)/PC 38:7 | 1.18 | (1.07, 1.30) | 1.4E−03 |
| Cer(d18:1/20:0)/PC 36:6 | 1.13 | (1.05, 1.22) | 1.4E−03 |
| Cer(d18:2/16:0)/Cer(d18:2/24:0) | 1.15 | (1.05, 1.26) | 1.6E−03 |
| Cer(d18:1/18:0)/PC 16:0/22:5 | 1.16 | (1.05, 1.27) | 2.4E−03 |
| Cer(d18:1/24:1)/PC 36:6 | 1.16 | (1.05, 1.28) | 2.5E−03 |
| Cer(d18:2/18:0)/Cer(d18:2/24:0) | 1.15 | (1.05, 1.25) | 2.7E−03 |
| Cer(d20:1/24:1)/PC 40:6 | 1.14 | (1.04, 1.26) | 6.0E−03 |
| Cer(d18:1/20:0)/PC 38:7 | 1.06 | (1.02, 1.11) | 7.4E−03 |
| Cer(d18:1/16:0)/PC 16:0/22:5 | 1.10 | (1.00, 1.21) | 4.7E−02 |

95% CI = 95% confidence interval.

Those skilled in the art will recognize, or be able to ascertain using no more than routine experimentation, numerous equivalents to the specific embodiments described herein both in the Examples and in the body of the entire description. Such equivalents are considered to be within the scope of the present disclosure and are intended to be encompassed by the following claims or the items listed above.

The invention claimed is:

1. A method for treating a subject being at risk to develop one or more cardiovascular (CV) events, wherein the method comprises:

(a) assaying a sample from the subject to determine a concentration of at least one ceramide (Cer) selected from Cer(d18:1/16:0), Cer(d18:1/18:0), Cer(d18:1/24:1) or Cer(d18:1/24:0);
(b) assaying the sample from the subject to determine a concentration of at least one phosphatidylcholine (PC), wherein the at least one PC comprises PC 14:0/22:6;
(c) identifying the subject at risk to develop one or more CV events based on an increased concentration of the at least one Cer selected from Cer(d18:1/16:0), Cer(d18:1/18:0), or Cer(d18:1/24:1), when compared to a control, and/or a decreased concentration of the at least one Cer, when compared to a control, wherein the at least one Cer comprises Cer(d18:1/24:0), and a decreased concentration of PC 14:0/22:6, when compared to a control; and
(d) treating the subject being at risk of developing one or more CV events, wherein the treating comprises administering an HMG-CoA reductase inhibitor.

2. The method of claim 1, wherein the method further comprises:
(i) assaying the sample to determine a concentration of at least one additional Cer; and/or
(ii) assaying the sample to determine a concentration of at least one additional PC; and
(iii) determining that the subject has a risk to develop one or more CV events, if the sample contains an increased or decreased concentration of the at least one additional Cer and/or the at least one additional PC, when compared to a control,
wherein the at least one additional Cer whose increase in concentration is compared to the control is selected from the group consisting of:
Cer(d16:1/16:0), Cer(d16:1/18:0), Cer(d16:1/24:1), Cer(d16:1/20:0), Cer(d16:1/22:0), Cer(d18:1/14:0), Cer(d18:1/20:0), Cer(d18:1/22:0), Cer(d18:1/26:1), Cer(d18:2/16:0), Cer(d18:2/18:0), Cer(d18:2/20:0), Cer(d18:2/22:0), Cer(d18:2/24:1), Cer(d18:2/26:1), Cer(d20:1/22:0), and Cer(d20:1/24:1)
wherein the at least one additional Cer whose decrease in concentration is compared to the control is selected from the group consisting of:
Cer(d16:1/23:0), Cer(d16:1/24:0), Cer(d16:1/26:0), Cer(d18:1/23:0), Cer(d18:1/26:0), Cer(d20:1/23:0), Cer(d20:1/24:0), Cer(d18:2/23:0), Cer(d18:2/24:0), and Cer(d18:2/26:0),
wherein the at least one additional PC whose increase in concentration is compared to the control is selected from the group consisting of:
PC 14:0/14:0, PC 14:0/16:0, PC 14:0/16:1, PC 14:1/16:0, PC 14:0/18:0, PC 16:0/16:0, PC 16:0/17:3, PC 16:1/17:2, PC 16:2/17:1, PC 16:3/17:0, PC 16:0/18:0, PC 14:0/20:0, PC 17:0/18:3, PC 17:1/18:2, PC 17:2/18:1, PC 17:3/18:0, PC 14:1/22:6, PC 14:2/22:5, PC 14:3/22:4, PC 16:2/20:5, PC 16:3/20:4, PC 16:4/20:3, PC 18:3/18:4, PC 14:1/23:0, PC 16:1/21:0, PC 18:1/19:0, PC 17:0/20:1, PC 17:1/20:0, PC 14:2/26:0, PC 16:1/24:1, PC 16:2/24:0, PC 18:1/22:1, PC 18:2/22:0, PC 20:0/20:2, PC 20:1/20:1, PC 16:3/24:1, PC 16:4/24:0, PC 18:0/22:4, PC 18:3/22:1, PC 18:4/22:0, PC 20:0/20:4, PC 20:1/20:3, PC 20:2/20:2, PC 28:0, PC 30:0, PC 30:1, PC 32:0, PC 33:3, PC 34:0, PC 35:3, PC 36:7, PC 37:1, PC 40:2, and PC 40:4
wherein the at least one additional PC whose decrease in concentration is compared to the control is selected from the group consisting of:
PC 14:0/14:1, PC 14:0/16:2, PC 14:1/16:1, PC 14:2/16:0, PC 14:0/17:0, PC 14:0/17:1, PC 14:1/17:0, PC 14:0/18:1, PC 16:0/16:1, PC 14:1/18:0, PC 14:0/18:2, PC 14:2/18:0, PC 14:1/18:1, PC 16:1/16:1, PC 16:0/16:2, PC 14:3/18:0, PC 14:2/18:1, PC 14:1/18:2, PC 14:0/18:3, PC 16:0/16:3, PC 16:1/16:2, PC 16:2/16:1, PC 16:0/17:1, PC 16:1/17:0, PC 16:0/17:2, PC 16:1/17:1, PC 16:2/17:0, PC 16:0/18:1, PC 16:1/18:0, PC 14:0/20:1, PC 14:1/20:0, PC 16:0/18:2, PC 16:1/18:1, PC 16:2/18:0, PC 14:0/20:2, PC 14:1/20:1, PC 14:2/20:0, PC 16:0/18:3, PC 16:1/18:2, PC 16:2/18:1, PC 16:3/18:0, PC 14:0/20:3, PC 14:1/20:2, PC 14:2/20:1, PC 14:3/20:0, PC 16:0/18:4, PC 16:1/18:3, PC 16:2/18:2, PC 16:3/18:1, PC 16:4/18:0, PC 14:0/20:4, PC 14:1/20:3, PC 14:2/20:2, PC 14:3/20:1, PC 16:1/18:4, PC 16:2/18:3, PC 16:3/18:2, PC 16:4/18:1, PC 14:0/20:5, PC 14:1/20:4, PC 14:2/20:3, PC 14:3/20:2, PC 16:0/19:0, PC 17:0/18:0, PC 17:0/18:1, PC 17:1/18:0, PC 16:1/19:0, PC 17:0/18:2, PC 17:1/18:1, PC 17:2/18:0, PC 17:0/18:4, PC 17:1/18:3, PC 17:2/18:2, PC 17:3/18:1, PC 17:4/18:0, PC 17:1/18:4, PC 17:2/18:3, PC 17:3/18:2, PC 17:4/18:1, PC 18:0/18:0, PC 16:0/20:0, PC 14:0/22:0, PC 18:0/18:1, PC 16:0/20:1, PC 16:1/20:0, PC 14:0/22:1, PC 14:1/22:0, PC 18:0/18:2, PC 18:1/18:1, PC 16:0/20:2, PC 16:1/20:1, PC 16:2/20:0, PC 14:0/22:2, PC 14:1/22:1, PC 14:2/22:0, PC 16:0/20:3, PC 18:1/18:2, PC 18:0/18:3, PC 16:1/20:2, PC 16:2/20:1, PC 16:3/20:0, PC 14:0/22:3, PC 14:1/22:2, PC 14:2/22:1, PC 14:3/22:0, PC 16:0/20:4, PC 18:2/18:2, PC 18:1/18:3, PC 18:0/18:4, PC 16:1/20:3, PC 16:2/20:2, PC 16:3/20:1, PC 16:4/20:0, PC 14:0/22:4, PC 14:1/22:3, PC 14:2/22:2, PC 14:3/22:1, PC 16:0/20:5, PC 18:1/18:4, PC 18:2/18:3, PC 16:1/20:4, PC 16:2/20:3, PC 16:3/20:2, PC 16:4/20:1, PC 14:1/22:5, PC 14:2/22:4, PC 14:3/22:3, PC 16:1/20:5, PC 16:2/20:4, PC 16:3/20:3, PC 16:4/20:2, PC 18:2/18:4, PC 18:3/18:3, PC 14:2/23:0, PC 16:2/21:0, PC 18:2/19:0, PC 17:0/20:2, PC 17:1/20:1, PC 17:2/20:0, PC 17:0/20:3, PC 14:3/23:0, PC 16:3/21:0, PC 18:3/19:0, PC 17:1/20:2, PC 17:2/20:1, PC 17:0/20:4, PC 16:4/21:0, PC 18:4/19:0, PC 17:1/20:3, PC 17:2/20:2, PC 17:3/20:1, PC 17:4/20:0, PC 17:1/20:5, PC 17:2/20:4, PC 17:3/20:3, PC 17:4/20:2, PC 14:0/24:0, PC 16:0/22:0, PC 17:0/21:0, PC 18:0/20:0, PC 19:0/19:0, PC 14:1/24:0, PC 16:0/22:1, PC 17:1/21:0, PC 18:0/20:1, PC 18:1/20:0, PC 14:2/24:0, PC 16:1/22:0, PC 18:0/20:2, PC 18:1/20:1, PC 18:2/20:0, PC 18:0/20:3, PC 14:3/24:0, PC 16:3/22:0, PC 16:2/22:1, PC 17:3/21:0, PC 18:1/20:2, PC 18:2/20:1, PC 18:3/20:0, PC 18:0/20:4, PC 16:4/22:0, PC 16:3/22:1, PC 17:4/21:0, PC 18:1/20:3, PC 18:2/20:2, PC 18:3/20:1, PC 18:4/20:0, PC 16:0/22:5, PC 18:0/20:5, PC 16:1/22:4, PC 16:4/22:1, PC 18:1/20:4, PC 18:2/20:3, PC 18:3/20:2, PC 18:4/20:1, PC 16:0/22:6, PC 16:1/22:5, PC 18:1/20:5, PC 18:2/20:4, PC 18:3/20:3, PC 18:4/20:2, PC 16:1/22:6, PC 16:2/22:5, PC 16:3/22:4, PC 18:2/20:5, PC 18:3/20:4, PC 16:0/23:0, PC 17:0/22:0, PC 18:0/21:0, PC 19:0/20:0, PC 16:2/23:0, PC 17:2/22:0, PC 18:2/21:0, PC 19:0/20:2, PC 16:4/23:0, PC 17:4/22:0, PC 18:4/21:0, PC 19:0/20:4, PC 19:0/20:6, PC 14:1/26:0, PC 16:0/24:1, PC 16:1/24:0, PC 18:0/22:1, PC 18:1/22:0, PC 20:0/20:1, PC 14:3/26:0, PC 16:2/24:1, PC 16:3/24:0, PC 18:2/22:1, PC 18:3/22:0, PC 20:0/20:3, PC 20:1/20:2, PC 16:4/24:1, PC 16:0/24:5, PC 18:0/22:5, PC 18:1/22:4, PC 18:4/22:1, PC 20:0/20:5, PC 20:1/20:4, PC 20:2/20:3, PC 16:0/24:6, PC 16:1/24:5, PC 18:0/22:6, PC 18:1/22:5, PC 18:2/22:4, PC 20:1/20:5, PC 20:2/20:4, PC 20:3/20:3, PC 16:2/24:6, PC 16:3/ 24:5, PC 18:2/22:6, PC 18:3/22:5, PC 18:4/22:4, PC 20:3/20:5, PC 20:4/20:4, PC 28:1, PC 30:2, PC 31:0, PC 31:1, PC 32:1, PC 32:2, PC 32:3, PC 33:1, PC 33:2, PC 34:1, PC 34:2, PC 34:3, PC 34:4, PC 34:5, PC 35:0, PC 35:1, PC 35:2, PC 35:4, PC 35:5, PC 36:0, PC 36:1, PC 36:2, PC 36:3, PC 36:4, PC 36:5, PC 36:6, PC 37:2, PC 37:3, PC 37:4, PC 37:6, PC 38:0, PC 38:1, PC 38:2, PC 38:3, PC 38:4, PC 38:5, PC 38:6, PC 38:7, PC 39:0, PC 39:2, PC 39:4, PC 39:6, PC 40:1, PC 40:3, PC 40:5, PC 40:6, and PC 40:8.

3. The method of claim 2, wherein the at least one additional Cer is Cer(d18:1/22:0), Cer(d18:1/20:0), Cer (d18:1/26:0), Cer(d18:1/26:1), Cer(d16:1/16:0), Cer(d16:1/ 18:0), Cer(d16:1/24:0), Cer(d16:1/24:1), Cer(d18:2/16:0), Cer(d18:2/18:0), Cer(d18:2/24:0), and/or Cer(d18:2/24:1), and/or wherein the at least one additional PC is PC 16:0/ 16:0, PC 16:0/22:5 PC 18:0/20:5, PC 16:0/20:4, PC 18:0/ 20:4, PC 18:0/20:3, PC 16:0/22:6, PC 16:1/18:2, PC 16:0/ 18:3, PC 17:0/20:3, PC 17:0/20:4, PC 32:0, PC 38:5, PC 36:6, PC 36:4, PC 38:4, PC 38:3, PC 38:6, PC 38:7, PC 34:3, PC 37:3, PC 37:4, PC 34:4 and/or PC 40:8.

4. The method of claim 1, wherein the cardiovascular (CV) event comprises stable angina pectoris, unstable angina pectoris, myocardial infarction (MI), acute myocardial infarction (AMI), acute coronary syndrome (ACS), stroke, transient ischemic attacks, deep vein thrombosis, heart failure, hospitalization for heart failure, cardiovascular death, peripheral artery disease and/or arrhythmia, and optionally wherein the CV event is induced by atherosclerosis.

5. The method of claim 1, wherein the sample is a biological sample, and optionally wherein the sample is a blood sample, a serum sample, a plasma sample, a saliva sample, a urine sample, a tissue sample, a fraction thereof or a dried blood spot, and further optionally wherein the sample is a dried plasma or serum collected on a card.

6. The method of claim 1, wherein the control is a control sample or a control value obtained from one individual or a population of individuals, optionally wherein the control is from a healthy individual, a generalized population of healthy individuals, a CVD patient that has remained free of any major CV events, or a group of CVD patients that have remained free of any major CV events, and further optionally wherein the control is obtained from the previously obtained sample from the same subject.

7. The method of claim 6, wherein the control value comprises a concentration or a score.

8. The method of claim 1, wherein the treatment further comprises providing additional therapeutic modification, and/or behavioral and/or lifestyle modification, or providing any medical and/or lifestyle management services to the subject, and optionally wherein the treatment comprises controlling of progression of CVD and/or its complications.

9. The method of claim 1, wherein the concentrations are determined by using mass spectrometry, nuclear magnetic resonance spectroscopy, fluorescence spectroscopy or dual polarization interferometry, a high performance separation method an immunoassay and/or an assay with a binding moiety capable of specifically binding the analyte.

10. The method of claim 9, wherein the high-performance separation method comprises liquid chromatography (LC), gas chromatography (GC), high performance liquid chromatography (HPLC), ultra-high performance liquid chromatography (UHPLC) or ultra performance liquid chromatography (UPLC).

11. The method of claim 1, wherein a concentration ratio is calculated from the concentrations of the at least one, at least 2, at least 3, at least 4 Cers and/or the concentration of the at least one PC, and optionally wherein the concentration ratio is Cer(d18:1/24:1)/Cer(d18:1/24:0), Cer(d18:1/16:0)/ PC 16:0/22:5 and/or Cer(d18:1/18:0)/PC 14:0/22:6.

12. The method of claim 11, wherein the concentration ratio is Cer(d18:1/24:1)/Cer(d18:1/24:0), Cer(d18:1/16:0)/ PC 16:0/22:5 and/or Cer(d18:1/18:0)/PC 14:0/22:6 and wherein the method further comprises determining the concentration of PC 16:0/16:0.

13. The method of claim 1, wherein the method further comprises determining a concentration of an additional cardiovascular risk biomarker selected from the group consisting of triglyseride (TG), C-reactive protein (CRP), troponin T (TNT or TnT), troponin I (TNI or TnI), B-type natriuretic peptide (BNP), N-terminal pro B-type natriuretic peptide (NT-proBNP), cystatin C, glycated haemoglobin A1c (HbA1c), glucose, suppression of tumorigenicity 2 (St2), galectin, trimethylamine-N-oxide (TMAO), lipoprotein-associated phospholipase A2 (Lp-PLA2), growth differentiation factor 15 (GDF15), lipoprotein (a) (Lp(a)), lipoprotein subgroup composition, lipoprotein subgroup particle number, creatine kinase (CK), and any combination thereof,
and optionally determining or obtaining personal information or health data and using the personal information or health data to determine the risk, wherein the personal information or health data is selected from the group consisting of sex, age, blood pressure, body mass index (BMI), smoking status, diabetes, lipid lowering treatment, history of cardiovascular disease (CVD), history of cardiovascular (CV) events, ethnic background, geographical location, family history of CVD, CV events, diabetes, medical imaging data, data from angiography, data from computed tomography (CT), and any combination thereof.

14. The method of claim 1, wherein the method further comprises a continuous or discrete scoring system based on the Cer, PC, Cer/PC, Cer/Cer, PC/Cer, PC/PC and/or determining a concentration of an additional cardiovascular risk biomarker selected from the group consisting of triglyseride (TG), C-reactive protein (CRP), troponin T (TNT or TnT), troponin I (TNI or TnI), B-type natriuretic peptide (BNP), N-terminal pro B-type natriuretic peptide (NT-proBNP), cystatin C, glycated haemoglobin A1c (HbA1c), glucose, suppression of tumorigenicity 2 (St2), galectin, trimethylamine-N-oxide (TMAO), lipoprotein-associated phospholipase A2 (Lp-PLA2), growth differentiation factor 15 (GDF15), lipoprotein (a) (Lp(a)), lipoprotein subgroup composition, lipoprotein subgroup particle number, creatine kinase (CK), and any combination thereof,
optionally wherein the score is based on at least 2, at least 3, at least 4, at least 5, at least 6 or at least 7 of the following lipids: Cer(d18:1/16:0), Cer(d18:1/18:0), Cer(d18:1/24:0), Cer(d18:1/24:1), PC 16:0/22:5, PC 14:0/22:6 and/or PC 16:0/16:0.

15. The method of claim 1, wherein the at least one Cer comprises Cer(d18:1/16:0), Cer(d18:1/18:0), Cer(d18:1/24: 1) and Cer(d18:1/24:0); and wherein the at least one PC comprises PC 14:0/22:6, PC 16:0/22:5 and PC 16:0/16:0, and
wherein the determining comprises:
determining that the subject has the risk to develop one or more CV events, if the sample contains increased concentrations of Cer(d18:1/16:0), Cer(d18:1/18:0), Cer(d18:1/24:1), and PC 16:0/16:0, when compared to the control, and decreased concentrations of Cer(d18:1/24:0), PC 14:0/22:6 and PC 16:0/22:5, when compared to the control.

16. The method of claim 1, wherein the method further comprises adding at least one isotope-labelled Cer and/or at least one isotope-labelled PC to the sample, and optionally wherein the isotope is deuterium, $^{13}C$ or $^{15}N$.

17. The method of claim 16, wherein the at least one isotope-labelled Cer and/or PC is selected from the following isotope-labelled lipids: Cer(d18:1/16:0), Cer(d18:1/18:0), Cer(d18:1/24:0), Cer(d18:1/24:1), PC 16:0/22:5, PC 14:0/22:6 and PC 16:0/16:0, and optionally wherein the at least one isotope-labelled Cer and/or PC is d7-Cer(d18:1/16:0), d7-Cer(d18:1/18:0), d7-Cer(d18:1/24:0), d7-Cer(d18:1/24:1), d9-PC 16:0/22:5, d9-PC 14:0/22:6 and/or d9-PC 16:0/16:0.

* * * * *